(12) United States Patent
Grant et al.

(10) Patent No.: US 12,729,676 B2
(45) Date of Patent: Sep. 8, 2026

(54) LIQUID PUMPING CASSETTES AND ASSOCIATED PRESSURE DISTRIBUTION MANIFOLD AND RELATED METHODS

(71) Applicant: DEKA Products Limited Partnership, Manchester, NH (US)

(72) Inventors: Kevin L. Grant, Litchfield, NH (US); Timothy A. Deva, Woburn, MA (US); Rachel T. Muradian, Manchester, NH (US); David J. Simoneau, High Point, NC (US); Brian D. Tracey, Litchfield, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 6 days.

(21) Appl. No.: 18/794,680

(22) Filed: Aug. 5, 2024

(65) Prior Publication Data

US 2025/0035101 A1 Jan. 30, 2025

Related U.S. Application Data

(60) Continuation-in-part of application No. 18/167,736, filed on Feb. 10, 2023, now Pat. No. 12,078,162, (Continued)

(51) Int. Cl.
*F04B 43/02* (2006.01)
*A61B 5/15* (2006.01)
(Continued)

(52) U.S. Cl.
CPC .......... *F04B 43/026* (2013.01); *A61B 5/1405* (2013.01); *A61J 1/201* (2015.05); (Continued)

(58) Field of Classification Search
CPC .. F04B 43/026; A61B 5/1405; A61M 1/1524; A61M 1/155; A61M 1/156; A61M 1/16;
(Continued)

(56) References Cited

U.S. PATENT DOCUMENTS

| | | | | |
|---|---|---|---|---|
| 2008/0208103 A1 | 8/2008 | Demers et al. | | |
| 2011/0004187 A1* | 1/2011 | Beiriger | ................ | A61M 5/162 604/500 |

(Continued)

OTHER PUBLICATIONS

International Search Report & Written Opinion mailed Nov. 6, 2024, issued in PCT Patent Application No. PCT/US2024/040957, 25 pages.

*Primary Examiner* — Audrey B. Walter
(74) *Attorney, Agent, or Firm* — Michael George Norris

(57) ABSTRACT

A blood circuit assembly with a vial holder for a blood pump cassette with a circular receiver and pads to center the vial holder. A blood circuit assembly may include a single, unitary member that defines portions of a pair of blood pumps, control valves, channels to accurately position flexible tubing for an occluder, an air trap support, and/or other portions of the assembly. The occluder door interaction with the unitary member provides added safety checks. A blood circuit assembly engagement device may assist with retaining a blood circuit assembly on the dialysis unit, and/or with removal of the assembly. A dialysate circuit assembly includes a balance pod with a stiffening elements to improve durability.

12 Claims, 54 Drawing Sheets

Related U.S. Application Data which is a continuation of application No. 17/751,342, filed on May 23, 2022, now Pat. No. 11,598,329, which is a division of application No. 16/370,039, filed on Mar. 29, 2019, now Pat. No. 11,371,498.

(60) Provisional application No. 62/745,807, filed on Oct. 15, 2018, provisional application No. 62/650,820, filed on Mar. 30, 2018.

(51) Int. Cl.

| | |
|---|---|
| ***A61J 1/20*** | (2006.01) |
| ***A61M 1/14*** | (2006.01) |
| ***A61M 1/16*** | (2006.01) |
| ***A61M 1/36*** | (2006.01) |
| ***A61M 5/14*** | (2006.01) |

(52) U.S. Cl.

CPC .......... *A61M 1/1524* (2022.05); *A61M 1/155* (2022.05); *A61M 1/156* (2022.05); *A61M 1/16* (2013.01); *A61M 1/1656* (2013.01); *A61M 1/362227* (2022.05); *A61M 1/36225* (2022.05); *A61M 1/362266* (2022.05); *A61M 1/3672* (2013.01); *A61M 5/1415* (2013.01); *A61M 5/1417* (2013.01); *A61M 1/15625* (2022.05)

(58) Field of Classification Search

CPC .......... A61M 1/1656; A61M 1/362227; A61M 1/36225; A61M 1/362266; A61M 1/3672; A61M 1/15625

See application file for complete search history.

(56) References Cited

U.S. PATENT DOCUMENTS

| | | | | |
|---|---|---|---|---|
| 2014/0112828 | A1* | 4/2014 | Grant .................. | A61M 1/3672 210/232 |
| 2016/0074578 | A1* | 3/2016 | Xu .................... | A61M 5/14586 604/132 |
| 2024/0123132 | A1 | 4/2024 | Grant et al. | |

* cited by examiner

3 WAY VALVE
2 WAY VALVE
2 WAY VALVE
PATIENT 632
642
634
646
644
630
619
636
617
638
640
515
616
630

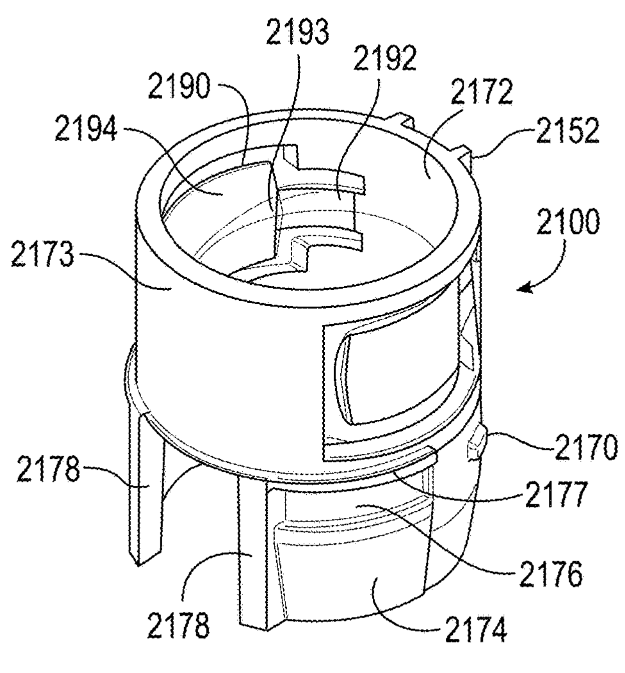
FIG. 21A
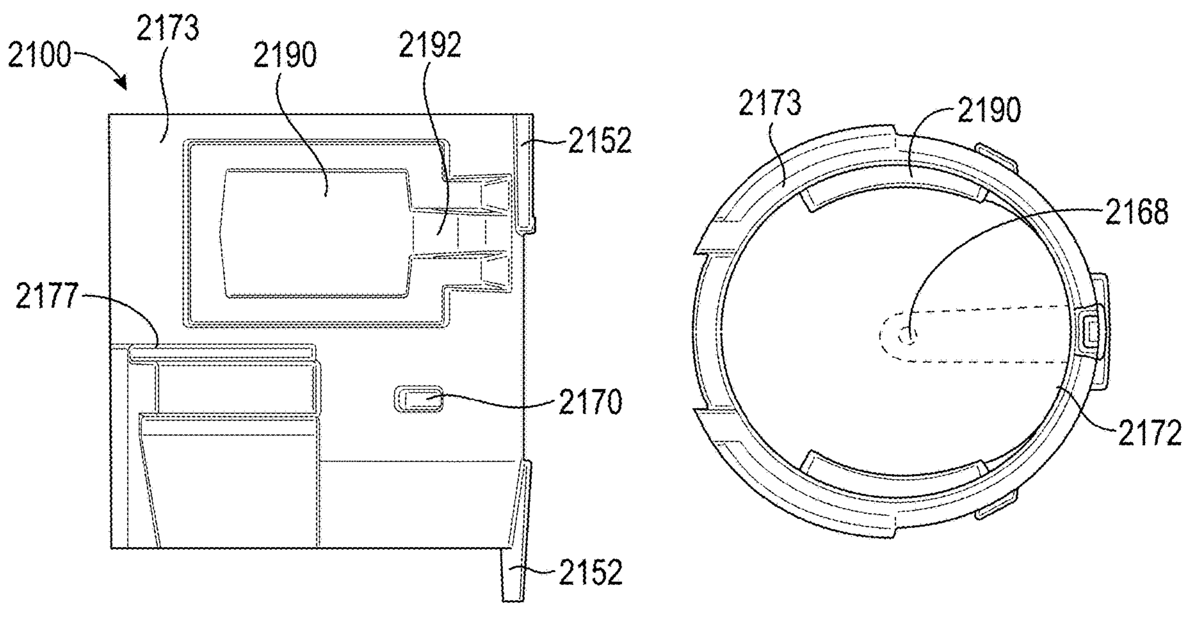
FIG. 21B
FIG. 21C

LIQUID PUMPING CASSETTES AND ASSOCIATED PRESSURE DISTRIBUTION MANIFOLD AND RELATED METHODS

CROSS-REFERENCE TO RELATED APPLICATION

The present application is a Continuation-in-Part of U.S. patent application Ser. No. 18/167,736, filed Feb. 10, 2023, which is a Continuation of U.S. patent application Ser. No. 17/751,342, filed May 23, 2022, now U.S. Pat. No. 11,598,329, issued Mar. 7, 2023, which is a Divisional of U.S. patent application Ser. No. 16/370,039, filed Mar. 29, 2019, now U.S. Pat. No. 11,371,498, issued Jun. 28, 2022, which claims the benefit of U.S. Provisional Patent Application Ser. No. 62/650,820, filed Mar. 30, 2018 and U.S. Provisional Patent Application Ser. No. 62/745,807, filed Oct. 15, 2018 all of which are hereby incorporated herein by reference in their entireties.

FIELD OF THE INVENTION

This disclosure generally relates to improvements in the design and construction of fluid pumping or mixing cassettes, cassette assemblies, their constituent parts, and associated devices.

BACKGROUND

Liquid-handling cassettes comprising diaphragm pumps and/or valves can be actuated fluidically (either hydraulically or pneumatically). In some examples, a cassette is designed to be fluidically connected to a pneumatic actuation manifold having electromechanical valves that selectively distribute positively or negatively pressurized gas or air to the cassette. A programmable electronic controller can be used to control the electromechanical valves to selectively deliver positive or negative pneumatic pressure to various pumps or valves of the cassette in a pre-determined manner.

Some fluid-handling cassettes can be substantially planar in shape, having a broad side flanked by a thin or narrow side having a relatively smaller thickness that the overall broad side dimensions of the cassettes. Liquid inlet and outlet ports can be incorporated into the edge or thin side of the cassette. But in many of these devices, actuation ports for the cassette have been located on the face or broad side of the cassette directly over the actuation chambers of the pumps or valves being controlled. This generally provides the shortest route for an actuation channel in the cassette from an external cassette actuation port to the actuation chamber and diaphragm of a pump or valve in the cassette. Furthermore, in many cases the pumping or valve stations or regions of the cassette—comprising either the actuation chamber on one side or the liquid carrying chamber on the opposing side—may be defined by spheroid or hemi-spheroid chamber walls that extend above the plane of the cassette face, which makes the overall cassette thicker than desirable in some applications. In other cases, a pump module may comprise a set of blocks sandwiched or laminated together, with the pneumatic actuation channels or fluid channels embedded within one or more of the blocks. This arrangement may also result in an overall device thickness greater than desirable for certain applications. Some applications may require a plurality of fluid handling cassettes to be mounted next to each other in tight spaces. In these cases, it may be desirable to position a number of cassettes adjacent to one another, to stack them against each other, or at least to place their broad sides face-to-face in close proximity. Reducing or minimizing the thickness of the individual cassettes constituting these assemblies may be particularly desirable.

It may be advantageous to arrange for a pump cassette to plug directly into its associated pressure distribution manifold (for example, a manifold that selectively delivers pneumatic pressure to the pump cassette under control of an electronic controller). In previously disclosed embodiments of a hemodialysis system using pneumatically actuated self-contained pump cassettes, the pump cassettes were connected to a corresponding pneumatic manifold via flexible tubes, which has led to significant challenges during assembly and in their operation. If a pump cassette can be located close to its associated manifold, a direct plug-in connection between the two would have substantial advantages. Under these circumstances, it would be particularly advantageous to have a compact manifold that allows for a direct interface to a pump cassette, arranged in such a manner as to allow the cassette or cassette assembly to be plugged into and unplugged from the actuation ports of the manifold with minimal effort.

In the design and operation of a pneumatic distribution manifold, the ability to use binary pressure control valves rather than continuously variable orifice valves would also provide significant advantages in both cost and reliability. But in this case, the control of pressure delivery to individual cassette pumps or valves by binary pressure control valves poses additional challenges that must be overcome. A sufficiently robust electronic controller can be programmed to use control algorithms to control the frequency and duration of binary valve actuation to achieve precise control of associated pneumatically actuated pumps or valves.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a back plate. The back plate also includes a front plate with an opening. The plate also includes a midplate bonded to back pate on a first face and bonded to the front plate on opposite face; and a vial holder configured to receive a vial and may include: a vial support may include: a vertically oriented spine that extends through the front plate and is fused to the mid-plate a support ring integral to the spine and with a vertically oriented center axis of the ring, a support arm that extends horizontally from the spine, and a hollow spike with a first end that extends vertically from the support arm and a second end that extends through the support arm to a first fluid channel in the blood pump cassette. The plate also includes a support cylinder aligned with the support ring and may include: two pads located on opposite sides of the support cylinder and attached to support cylinder by a living hinges that bend about a vertical axis, a first complete ring above the pads, and a second complete ring below the pads, where the support cylinder is mechanically attached to the to the support ring. The plate also includes where said vial holder is configured to receive a cylindrical vial; where the two opposed pads that are configured to center the vial over the hollow spike Other embodiments of this aspect include corresponding computer systems, apparatus, and computer programs recorded on one or more computer storage devices, each configured to perform the actions of the methods.

Implementations may include one or more of the following features. The disposable blood cassette where the spine is fused to the housing with ultrasonic welding, adhesives, or laser welding. The blood cassette may include: a blood pump; a blood inlet; a blood outlet; and one or more blood channels fluidly connecting the blood inlet to the blood pump and fluidly connecting the blood pump to the blood outlet; where the first fluid channel is fluidly connected to at least one of the blood channels. The disposable blood cassette where the first fluid channel is connected to the one of the blood channels via a valve and a metering pump. The disposable blood cassette where the first fluid channel is a port to a diaphragm valve. The disposable blood cassette where the spine is fused to the housing with ultrasonic welding, adhesives, or laser welding. The second end of the hollow spike extends through the front plate and is sealed with an O-ring held between the spine and the mid-plate. The pads contain tampered surfaces above the contact surface that that provide a ramp that makes contact with said cylindrical vial as the vial moves toward the hollow spike and facilitates the movement of the vial toward the support arm. The cylindrical wall of the vial holder is reinforced by gussets for structural integrity which connect the support spine to the cylindrical wall or ring. Implementations of the described techniques may include hardware, a method or process, or computer software on a computer-accessible medium.

One general aspect includes a disposable blood cassette with a vial holder for use in a hemodialysis unit a blood pump may include: a housing, a blood pump, a blood inlet, a blood outlet, and one or more fluid channels fluidly connecting the blood inlet to the blood pump and fluidly connecting the blood pump to the blood outlet, and a vial holder to receive a vial and may include: a vial support may include: a vertically oriented spine fused to the housing, a support ring that is integral to the spine and oriented so the center axis of the ring is vertical, a support arm that extends horizontally from the spine, and a hollow spike with a first end that extends vertically from the support arm and a second end that extends through the support arm to a fluid channel. The cassette also includes a support cylinder aligned with the support ring and may include: two pads located on opposite sides of the support cylinder and attached to support cylinder by a living hinges that bend about a vertical axis, a first complete ring above the pads, a second complete ring below the pads, and tabs that extend vertically off the second ring that mechanically attach the support cylinder to the support ring. The cassette also includes where said vial holder is configured to receive a cylindrical vial; where the two opposed pads that are configured to center the vial over the hollow spike. Other embodiments of this aspect include corresponding computer systems, apparatus, and computer programs recorded on one or more computer storage devices, each configured to perform the actions of the methods.

One general aspect includes a disposable blood with a vial holder for use in a hemodialysis unit a blood pump may include: a housing, a blood pump, a blood inlet, a blood outlet, and one or more fluid channels fluidly connecting the blood inlet to the blood pump and fluidly connecting the blood pump to the blood outlet. The blood also includes a vial holder to receive a vial and may include: a vial support may include: a vertically oriented spine fused to the housing a support ring that is integral to the spine and oriented so the center axis of the ring is vertical, a support arm that extends horizontally from the spine, and a hollow spike with a first end that extends vertically from the support arm and a second end that extends through the support arm to a fluid channel. The blood also includes a support cylinder aligned with the support ring and may include: two windows on opposite sides of the support cylinder; two pads, each located in a window and attached to the support cylinder by a living hinge that bends about a vertical axis; where the support cylinder is mechanically attached to the support ring. The blood also includes where the vial holder is configured to receive a vial; where the two opposed pads center the vial toward a plane defined by the first end of the hollow spike and the spine. Other embodiments of this aspect include corresponding computer systems, apparatus, and computer programs recorded on one or more computer storage devices, each configured to perform the actions of the methods.

Implementations may include one or more of the following features. The disposable blood cassette where the two opposed pads center the cylindrical vial with first end of the hollow spike. Implementations of the described techniques may include hardware, a method or process, or computer software on a computer-accessible medium.

One general aspect includes. The disposable blood pumping cassette also includes an inlet blood tube, may include a pliable tube with at least a first lumen; an outlet blood tube may include a pliable tube with at least a first lumen; a blood pump to pump blood from the inlet line to the outlet line; a tube organizer that may include a portion of the blood pump and is configured to mount to a medical device, the medical device includes an air-in-line sensor with a slot to receive a blood tube is configured to detect air bubbles in the blood tube, the organizing tray further may include: a first guide that holds the first blood tube of the two blood tubes, the first guide located above the sensor when the blood pump is mounted to the medical device; an extension that begins at the location of the first guide and extends over the sensor; and a flange with a first notch, the flange connected to the extension and the first notch configured to receive the first blood tube at a location below the air-in-line sensor when the tube organizer is mounted to the medical device; where the first guide and the first notch are aligned with the sensor slot. Other embodiments of this aspect include corresponding computer systems, apparatus, and computer programs recorded on one or more computer storage devices, each configured to perform the actions of the methods.

Implementations may include one or more of the following features. The disposable blood pumping cassette where the blood pump may include a pair of pneumatic pumps for receiving blood from the inlet blood tube, circulating blood through a circuit including a dialyzer unit and returning the blood to the outlet blood tube; The flow path from the blood pump to the outlet blood tube may include a dialyzer inlet tube, a dialyzer, an outlet dialyzer tube and an air trap. The tube organizer includes a mount for the air trap, the air trap configured to receive blood from the dialyzer via the dialyzer outlet tube and to send blood to the outlet blood tube. The tube organizer includes a second guide to hold the dialyzer inlet tube and a third guide to hold the outlet blood tube. The air-in-line sensor may include a second slot and the third guide holds the second blood tube of the two blood tubes above the second sensor slot and the flange may include a second notch that is configured to receive the second blood tube at a location below the air-in-line sensor where the third guide and the second notch are aligned with the second air-in-line sensor slot. Blood pump may include a pair of the pneumatic diaphragm pumps, each diaphragm pump having a pneumatic control port arranged for alignment and mating with corresponding ports located on an exposed front panel of the medical device. The flowpaths connect the fluid inlet to the primary pump chamber and connect the primary pump chamber to the fluid outlet. The back plate is an integral part of the tube organizer. The secondary pump diaphragm is configured to pump fluid between the first side and the second side of the mid-plate. The valve diaphragm is configured to occlude or permit fluid flow between the two valve fluid ports. A first one of said one or more diaphragm valves is interposed between the fluid inlet of the mid-plate and an inlet channel of the primary pump fluid chamber, and where a second one of said one or more diaphragm valves is interposed between the fluid outlet of the mid-plate and an outlet channel of the primary pump fluid chamber. The medical device is a hemodialysis unit. Implementations of the described techniques may include hardware, a method or process, or computer software on a computer-accessible medium.

One general aspect includes. The disposable blood pumping cassette also includes an inlet blood tube with a first lumen for fluid and a second lumen; an outlet blood tube with a first lumen for fluid and a second lumen; a blood pump to pump blood from the inlet blood tube to the outlet blood tube; an organizing tray that may include a portion of the blood pump and is configured to mount to a medical device, where the medical device includes a sensor with a slot to receive a blood tube and is configured to detect air bubbles in the blood tube, the organizing tray further may include: a first guide that holds the first blood tube of the two blood tubes, the first guide located above the sensor and aligned with the sensor slot when the blood pump is mounted to the medical device; and an extension that begins at the location of the first guide and extends over the sensor and may include a vertical groove that is aligned over sensor slot when the blood pump is mounted in the medical device. The cassette also includes where the vertical groove in the extension receives the second lumen to position the second lumen to improve the sensor signal. Other embodiments of this aspect include corresponding computer systems, apparatus, and computer programs recorded on one or more computer storage devices, each configured to perform the actions of the methods.

Implementations may include one or more of the following features. The disposable blood pumping cassette where vertical groove in the extension positions the second lumen so that only the first lumen enters the sensor slot. The blood pump may include a pair of pneumatic pumps for receiving blood from the inlet blood tube, circulating blood through a circuit including a dialyzer unit and returning the blood to the outlet blood tube; The flow path from the blood pump to the outlet blood tube may include a dialyzer inlet tube, a dialyzer, an outlet dialyzer tube and an air trap. The tube organizer includes a mount for the air trap configured to receive blood from the dialyzer via the dialyzer outlet tube and to send blood to the outlet blood tube. The tube organizer includes a second guide to hold the dialyzer inlet tube and a third guide to hold the outlet blood tube. Blood pump may include a pair of the pneumatic diaphragm pumps, each diaphragm pump having a pneumatic control port arranged for alignment and mating with corresponding ports located on an exposed front panel of the medical device. The flowpaths connect the fluid inlet to the primary pump chamber and connect the primary pump chamber to the fluid outlet. The back plate is an integral part of the tube organizer. The secondary pump diaphragm is configured to pump fluid between the first side and the second side of the mid-plate. The secondary pump pumps fluid from a vial mounted on the blood cassette to the flowpaths. The valve diaphragm is configured to occlude or permit fluid flow between the two valve fluid ports. A first one of said one or more diaphragm valves is interposed between the fluid inlet of the mid-plate and an inlet channel of the primary pump fluid chamber, and where a second one of said one or more diaphragm valves is interposed between the fluid outlet of the mid-plate and an outlet channel of the primary pump fluid chamber. Implementations of the described techniques may include hardware, a method or process, or computer software on a computer-accessible medium.

One general aspect includes. The disposable blood pumping cassette also includes an inlet blood tube; an outlet blood tube; a blood pump to pump blood from the inlet line to the outlet line; an organizing tray that may include a portion of the blood pump and is configured to mount to a medical device, the medical device includes a sensor with a slot to receive a blood tube configured to detect air bubbles in the blood tube, the organizing tray further may include a first guide that holds the first blood tube of the two blood tubes, the first guide located above the sensor when the blood pump is mounted to the medical device. The cassette also includes a cover that is attached to the organizing tray and includes an section that extends below the first guide to a flange that is perpendicular to the section and includes at least one notch to grip the blood tube at a location below the sensor when the organizing tray is mounted to the medical device. The cassette also includes where the first guide and the at least one notch are aligned with the sensor slot. Other embodiments of this aspect include corresponding computer systems, apparatus, and computer programs recorded on one or more computer storage devices, each configured to perform the actions of the methods.

One general aspect includes a system in a medical device to pump blood a blood pump cassette may include: an inlet blood tube, an outlet blood tube, a blood pump to pump blood from the inlet line to the outlet line, an organizing tray with a first guide to hold at least one blood tube of the inlet blood tube and the outlet blood tube, and an extension with a flange with a notch to grip the at least one blood tube, an occluder configured to occlude the at least one blood tube and may include: a first pathway configured to receive at least one blood tube, a occluding element configured to occlude the at least one blood tube in the pathway, a cover door configured to retain the at least one blood tube in the pathway when the cover door is closed and includes tab that overlaps the blood pump extension, and a door sensor that detects when the door is closed, and an air-in-line sensor including a slot to receive at least one blood tube and configured detect an air bubble in the at least one blood tube located in the slot, where the first guide and the first notch are located on opposite sides of the air-in-line sensor and the first guide and first notch are aligned with the sensor slot and the first pathway in the occluder when the blood pump is mounted on the medical device and where the occluder door can only close when notch in the flange has pushed the at least one blood tube into the air-in-line sensor slot and where a controller of the medical device will not allow the blood pump to operate if the occluder door is open. Other embodiments of this aspect include corresponding computer systems, apparatus, and computer programs recorded on one or more computer storage devices, each configured to perform the actions of the methods.

Implementations may include one or more of the following features. The disposable blood pumping cassette where the blood pump may include a pair of pneumatic pumps for receiving blood from the inlet blood tube, circulating blood through a circuit including a dialyzer unit and returning the blood to the outlet blood tube; The flow path from the blood pump to the outlet blood tube may include a dialyzer inlet tube, a dialyzer, an outlet dialyzer tube and an air trap. The tube organizer includes a mount for the air trap configured to receive blood from the dialyzer via the dialyzer outlet tube and to send blood to the outlet blood tube. The tube organizer includes a second guide to hold the dialyzer inlet tube and a third guide to hold the outlet blood tube. Blood pump may include a pair of the pneumatic diaphragm pumps, each diaphragm pump having a pneumatic control port arranged for alignment and mating with corresponding ports located on an exposed front panel of the medical device. The flowpaths connect the fluid inlet to the primary pump chamber and connect the primary pump chamber to the fluid outlet. The back plate is an integral part of the tube organizer. The secondary pump diaphragm is configured to pump fluid between the first side and the second side of the mid-plate. The secondary pump pumps fluid from a vial mounted on the blood cassette to the flowpaths. The valve diaphragm is configured to occlude or permit fluid flow between the two valve fluid ports. A first one of said one or more diaphragm valves is interposed between the fluid inlet of the mid-plate and an inlet channel of the primary pump fluid chamber, and where a second one of said one or more diaphragm valves is interposed between the fluid outlet of the mid-plate and an outlet channel of the primary pump fluid chamber. The medical device is a hemodialysis unit. Implementations of the described techniques may include hardware, a method or process, or computer software on a computer-accessible medium.

One general aspect includes a system in a medical device to pump blood a blood pump cassette may include: an inlet blood tube, an outlet blood tube, a blood pump to pump blood from the inlet line to the outlet line, an organizing tray with a first guide to hold at least one blood tube of the inlet blood tube and the outlet blood tube, and an extension with a flange with a notch to grip the at least one blood tube, an occluder configured to occlude the at least one blood tube and may include: a first pathway configured to receive at least one blood tube, a occluding element configured to occlude the at least one blood tube in the pathway, a cover door configured to retain the at least one blood tube in the pathway when the cover door is closed and includes tab that overlaps the blood pump extension, and a door sensor that detects when the door is closed, and an air-in-line sensor including a slot to receive at least one blood tube and configured detect an air bubble in the at least one blood tube located in the slot, where the first guide and the first notch are located on opposite sides of the air-in-line sensor and the first guide and first notch are aligned with the sensor slot and the first pathway in the occluder when the blood pump is mounted on the medical device and where the occluder door can only close when notch in the flange has pushed the at least one blood tube into the air-in-line sensor slot and where a controller of the medical device will not allow the medical device a therapy to start or continue if the occluder door is open. Other embodiments of this aspect include corresponding computer systems, apparatus, and computer programs recorded on one or more computer storage devices, each configured to perform the actions of the methods.

One general aspect includes a system in a medical device to pump blood. The system also includes a blood tube; an occluder configured to occlude the at least one blood tube and may include: a first pathway configured to receive at least one blood tube, a occluding element configured to occlude the at least one blood tube in the pathway, a cover door configured to retain the at least one blood tube in the pathway when the cover door is closed and includes tab that overlaps the blood pump extension, and a door sensor that detects when the door is closed, an air-in-line sensor including a slot to receive at least one blood tube and configured detect an air bubble in the at least one blood tube located in the slot, and a blood tube cover that is aligned with the air-in-line sensor slot and configured to push the blood tube into the slot when pressed toward the air-in-line sensor where the occluder door can only close when blood tube cover has pushed the blood tube into the air-in-line sensor slot and where a controller of the medical device will not allow the blood pump to operate if the occluder door is open. Other embodiments of this aspect include corresponding computer systems, apparatus, and computer programs recorded on one or more computer storage devices, each configured to perform the actions of the methods.

One general aspect includes a balance pod in a balance circuit. The balance pod also includes a first rigid chamber with a circular dome, a first fluid port, and a first rim, the circular dome having an axis of rotation, the axial height of the circular dome being less than half the outer diameter of the circular dome, the first rim extending from the outer diameter of the circular dome in a direction perpendicular to the axis of rotation, the first fluid port extending from the dome in a direction parallel to the axis of rotation. The pod also includes a second rigid chamber with a circular dome, a second fluid port, and a second rim, the circular dome having an axis of rotation, the axial height of the circular dome being less than half the outer diameter of the circular dome, the second rim extending from the outer diameter of the circular dome in a direction perpendicular to the axis of rotation, the second fluid port extending from the dome in a. The pod also includes a flexible diaphragm with thickened rim. The pod also includes where the thickened rim of the flexible diaphragm is captured between the first rim and the second rim and the first rim is fused to the second rim. The pod also includes where at least the first rigid chamber further may include a cylinder that is aligned with the axis of rotation and extends from the outer surface of the dome and a plurality of gussets that extend radially from the inside surface of the cylinder to the outer surface of the dome. Other embodiments of this aspect include corresponding computer systems, apparatus, and computer programs recorded on one or more computer storage devices, each configured to perform the actions of the methods.

One general aspect includes a balance pod in a balance circuit. The balance pod also includes a first rigid chamber and a second rigid chamber, each chamber may include: a fluid port; a rim characterized by an outer diameter about a first axis and a concentric inner diameter; a circular dome centered on the first axis and integral to the inner diameter of the rim, the dome having a height that is less than half the inner diameter; a cylinder centered on the first axis and extending off the outside of the dome; and a plurality of gussets that extend radially from the inside surface of the cylinder to the outer surface of the dome. The pod also includes a flexible diaphragm including a membrane with a thickened rim. The pod also includes where the thickened rim of the flexible diaphragm is captured between the rim of the first rigid chamber and the rim of the second rigid chamber. The pod also includes where the rim of the first rigid chamber is fused to the rim of the second rigid chamber. Other embodiments of this aspect include corresponding computer systems, apparatus, and computer programs recorded on one or more computer storage devices, each configured to perform the actions of the methods.

Implementations may include one or more of the following features. The balance pod where the cylinder extends off the dome adjacent to inner diameter of the rim. The thickness of the cylinder is less than half the thickness of the dome. The thickness of the gussets is less than half the thickness of the dome. The rim of the first chamber may include a first groove on a flat surface facing away from the dome, and the rim of the second chamber may include a first ridge on a flat surface facing away from the dome and sized to be inserted into the groove and where the fusion joint of the first chamber to second chamber is located between a first groove and the first ridge. The rim of the first chamber may include a second groove and the rim of the second chamber may include a third groove, the second and third grooves are adjacent to the inner diameter of the rim, and the second and third grooves are sized so that a combined open volume between the second and third grooves receives the thickened rim of the diaphragm. The second and third grooves are aligned with each other when first and second chambers are fused. The second and third grooves are sized so that the combined open volume between the second and third grooves axially compressed the thickened rim of the diaphragm. The rim of the first chamber may include a second groove adjacent to an outer diameter of the circular dome, where an inner wall of the second groove is shorter than an outer wall of the groove and sized to accommodate the thickness of the diaphragm membrane. A edge of the inner wall is rounded to prove a smooth curve from the flat surface of the rim to the inner surface of the dome in the first chamber. Implementations of the described techniques may include hardware, a method or process, or computer software on a computer-accessible medium.

One general aspect includes a balance pod in a balance circuit. The balance pod also includes a first rigid chamber and a second rigid chamber, each chamber may include: a fluid port; a rim characterized by an outer diameter about a first axis and a concentric inner diameter, the rim includes a first groove adjacent and concentric to inner diameter; and a circular dome centered on the first axis and integral to the inner diameter of the rim, the dome having a height that is less than half the inner diameter. The pod also includes a flexible diaphragm including a membrane with a thickened rim. The pod also includes where the thickened rim of the flexible diaphragm is captured between the rim of the first rigid chamber and the rim of the second rigid chamber. The pod also includes where an inner wall of the first groove is shorter than an outer wall of the groove and sized to accommodate the thickness of the diaphragm membrane, and where the top edge of the inner wall is rounded to create a smooth curve from a first surface perpendicular to first axis rim to the inner surface of the dome in the chamber. Other embodiments of this aspect include corresponding computer systems, apparatus, and computer programs recorded on one or more computer storage devices, each configured to perform the actions of the methods.

One general aspect includes a balance pod in a balance circuit. The balance pod also includes a first rigid chamber and a second rigid chamber, each chamber may include: a fluid port; a rim characterized by an outer diameter about a first axis and a concentric inner diameter, the rim includes a first groove adjacent and concentric to inner diameter, where an inner wall of the first groove is shorter than an outer wall of the groove; and a circular dome centered on the first axis and integral to the inner diameter of the rim, the dome having a height that is less than half the inner diameter. The pod also includes a flexible diaphragm including a membrane with a thickened rim. The pod also includes where the thickened rim of the flexible diaphragm is captured between the rim of the first rigid chamber and the rim of the second rigid chamber. The pod also includes where at the end of a stroke the membrane bends to match an inner surface of the circular dome, and the bending of membrane occurs a distance inboard of the thickened rim. Other embodiments of this aspect include corresponding computer systems, apparatus, and computer programs recorded on one or more computer storage devices, each configured to perform the actions of the methods.

One general aspect includes the balance pod where the cylinder extends off the dome adjacent to inner diameter of the rim. Other embodiments of this aspect include corresponding computer systems, apparatus, and computer programs recorded on one or more computer storage devices, each configured to perform the actions of the methods.

Implementations may include one or more of the following features. A balance pod in a balance circuit. The balance pod includes a first rigid chamber and a second rigid chamber, each chamber may include: a fluid port; a rim characterized by an outer diameter about a first axis and a concentric inner diameter, the rim includes a first groove adjacent and concentric to inner diameter; and a circular dome centered on the first axis and integral to the inner diameter of the rim, the dome characterized by a height of the dome above the surface of the rim and an outer diameter. The pod includes a flexible diaphragm including a membrane with a thickened rim. The pod includes where the circular dome is the thickened rim of the flexible diaphragm is captured between the rim of the first rigid chamber and the rim of the second rigid chamber. The pod includes where the movement of the diaphragm membrane is characterized by a swept angle of the membrane surface near at the outer diameter of the circular dome and the height of the dome with respect to the outer diameter of the dome results in a swept angle of approximately 90 degrees. The pod includes 86: an integrated cassette assembly of a dialysis system a sensing system for sensing subject media may include: The pod includes a first cassette, a second cassette, and a third cassette, where the second cassette is interposed between the first cassette and the third cassette, the first cassette being connected to the second cassette by a first set of rigid conduits, and the third cassette is connected to the second cassette by a second set of rigid conduits and each cassette may include; a middle plate may include walls that extend from a center plate on a first side to form a first set of fluid channels, the channels fluidly connecting holes through the center plate walls that extend from the center plate on the second side to form a second set of fluid channels at least one circular wall that extends on the second side of the center plate to form at least one external port that is configured allow fluid to flow into or out of the cassette. The pod includes a first outer plate that is fused to the top of the extended walls to close the first set of fluid channels to create fluid conduits; a second outer plate that is fused to the top of the extended walls to close the second set of fluid channels and at least one opening to accommodate the external port that extends through the second outer plate; a sensor cassette may include: a manifold with a plurality of fluid channels, a sensor fluid port in the bottom of at least one of the fluid channels; a top plate fused to the plurality of fluid channels to form a separate fluid channel with each of the plurality of fluid channels; and a plurality of sensors probes that extend through the top plate and into the formed fluid conduits. The pod includes where the sensor cassette fluid port is fluidly connected via rigid tubes to the least one external port in the first cassette. The pod includes 87: the integrated cassette assembly where. The pod includes the sensor cassette may include a plurality of legs that extend below the manifold and toward the first cassette. The pod includes the second plate may include a plurality of openings configured to receive the plurality of legs. The pod includes where the plurality of legs are configured to latch into the plurality of openings. The pod includes 88: the integrated cassette assembly where plurality of legs are flexible and may include a step configured to hook onto the back side of the openings in the second plate. The pod includes 89: the integrated cassette assembly where the rigid tubes sets the minimum distance between the sensor cassette and the first cassette, and the plurality of legs sets the maximum distance between the sensor cassette and rigid tubes and plurality of legs are sized to rigidly attach the sensor cassette to the first cassette. The pod includes 90: the integrated cassette assembly where at least one of the fluid channels with a sensor fluid port at a first end of the channel includes a port to configured to connect to a flexible tube at the opposite end of the fluid channel. The pod includes 91: the integrated cassette assembly where at least one of the fluid channels with a sensor fluid port at a first end of the channel includes a second sensor fluid port at the opposite end of the fluid channel. The pod includes 92: the integrated cassette assembly where the rigid tubes are sealed to the sensor fluid port with an O-ring and to the external port with an O-ring. The pod includes 93: the integrated cassette assembly the manifold and top plate enclosing at least a first fluid flow path and a second fluid flow path which are fluidically isolated from each other during use of the sensing system, each of said first and second fluid flow paths having a fluid inlet port and a fluid outlet port. The pod includes 94: the integrated cassette assembly where the sensor probes are part of an apparatus for sensing conductivity of subject media in each of said first and second fluid flow paths, where the sensor apparatus may include a separate group of conductivity sensors associated with each of said first and second fluid flow paths, each group of conductivity sensors may include at least two conductivity sensing probes spaced apart from one another. The pod includes 95: the integrated cassette assembly where the sensor manifold is free of valves and pumping mechanisms. The pod includes 96: the integrated cassette assembly where the subject media may include a liquid. The pod includes 97: the integrated cassette assembly where the liquid may include dialysate solution. The pod includes 98: the integrated cassette assembly where at least one of the sensing probes may include a thermistor. The sensor cassette may include a printed circuit board located the side of the top plate not facing the manifold, and where the sensing probes are connected to the printed circuit board. The sensor cassette may include a cover that covers the printed circuit board and is fastened to the manifold. Implementations of the described techniques may include hardware, a method or process, or computer software on a computer-accessible medium.

BRIEF DESCRIPTION OF THE DRAWINGS

Non-limiting embodiments of the present invention will be described by way of example with reference to the accompanying figures, some of which are schematic, and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIGS. 21A to 21C are perspective, side and top views of the vial holder of the blood pump cassette in an illustrative embodiment;

DETAILED DESCRIPTION

Figure 1:
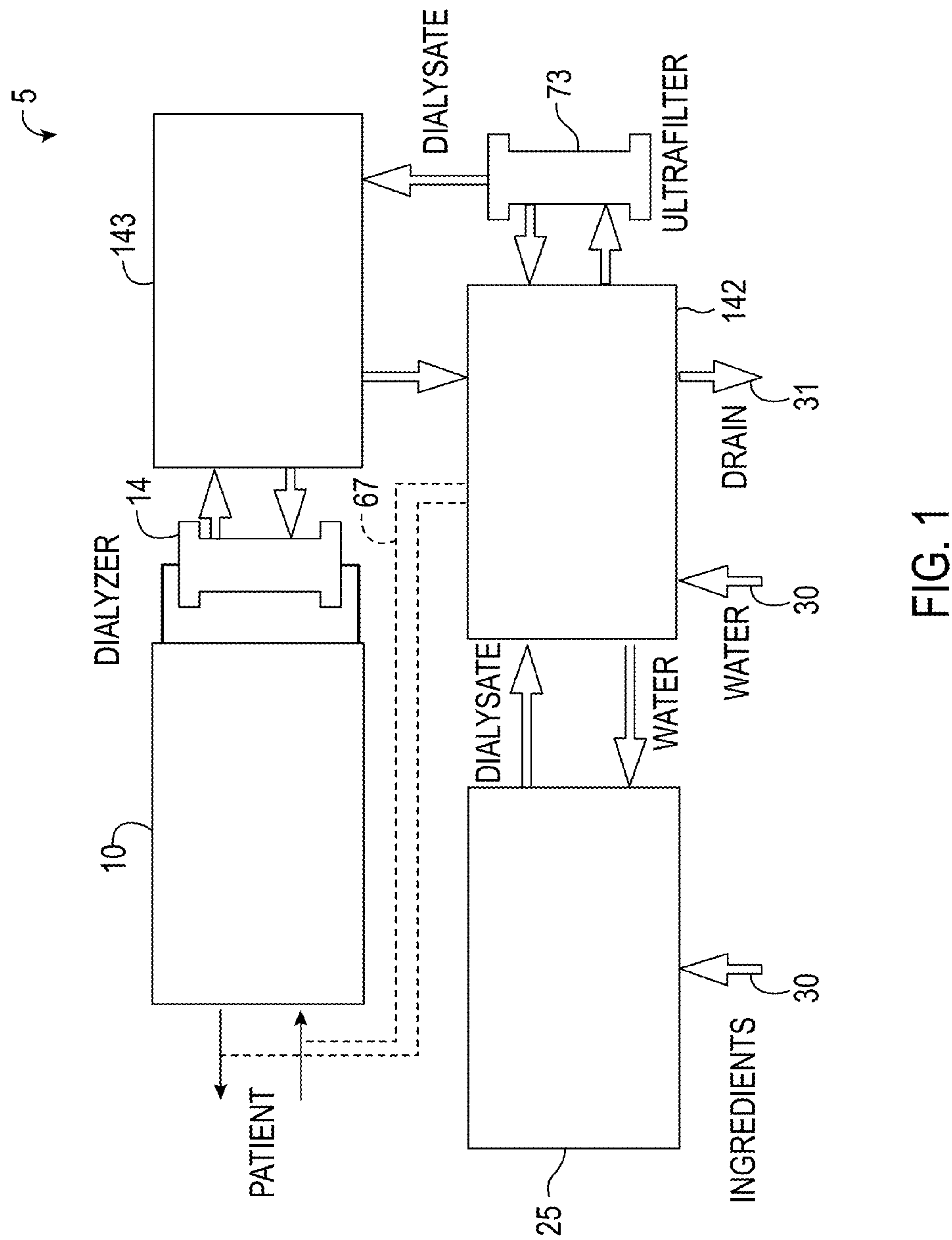
FIG. 1 is a high-level schematic of various embodiments of a dialysis system.

The present invention generally relates to therapeutic medical devices, such as hemodialysis and similar extracorporeal blood treatment systems, including a variety of systems and methods that would make hemodialysis more efficient, easier, and/or more affordable. Some aspects of the invention may be applied to other types of therapeutic medical devices, such as peritoneal dialysis devices, or intravenous infusion devices, as well as other devices that are configured to communicate with a remote server. One aspect of the invention is generally directed to new fluid circuits for fluid flow. In one set of embodiments, a hemodialysis system may include a blood flow path and a dialysate flow path, where the dialysate flow path includes one or more of a balancing circuit, a mixing circuit, and/or a directing circuit. Preparation of dialysate by the mixing circuit, in some instances, may be decoupled from patient dialysis. In some cases, the circuits are defined, at least partially, within one or more cassettes, optionally interconnected with conduits, pumps, or the like. The hemodialysis system may also include, in another aspect of the invention, one or more fluid handling devices, such as pumps, valves, mixers, or the like, which can be actuated using a control fluid, such as air.

Various aspects of the present invention are generally directed to new systems for hemodialysis and the like, such as hemofiltration systems, hemodiafiltration systems, plasmapheresis systems, etc. Accordingly, although the various systems and methods described herein are described in relation to hemodialysis, it should be understood that the various systems and method described herein are applicable to other dialysis systems and/or in any extracorporeal system able to treat blood or other bodily fluids, such as plasma.

As discussed above, a hemodialysis system typically includes a blood flow path and a dialysate flow path. It should be noted that within such flow paths, the flow of fluid is not necessarily linear, and there may be any number of "branches" within the flow path that a fluid can flow from an inlet of the flow path to an outlet of the flow path. Examples of such branching are discussed in detail below. In the blood flow path, blood is drawn from a patient, and is passed through a dialyzer, before being returned to the patient. The blood is treated by the dialyzer, and waste molecules (e.g., urea, creatinine, etc.) and water are passed from the blood, through a semi-permeable membrane in the dialyzer, into a dialysate solution that passes through the dialyzer by the dialysate flow path. In various embodiments, blood may be drawn from the patient from two lines (e.g., an arterial line and a venous line, i.e., "dual needle" flow), or in some cases, blood may be drawn from the patient and returned through the same needle (e.g., the two lines may both be present within the same needle, i.e., "single needle" flow). In still other embodiments, a "Y" site or "T" site is used, where blood is drawn from the patient and returned to the patient through one patient connection having two branches (one being the fluid path for the drawn blood, the second the fluid path for the return blood). In an embodiment, a "Y" or "T" connection can be made with a single-lumen needle or catheter. In another embodiment, a "dual needle" flow effect can be obtained with the use of a single catheter or needle having dual lumens. The patient may be any subject in need of hemodialysis or similar treatments, although typically the patient is a human. However, hemodialysis may be performed on non-human subjects, such as dogs, cats, monkeys, and the like.

In the dialysate flow path, fresh dialysate is prepared and is passed through the dialyzer to treat the blood from the blood flow path. The dialysate may also be equalized for blood treatment within the dialyzer (i.e., the pressure between the dialysate and the blood are equalized), i.e., the pressure of dialysate through the dialyzer is closely matched to the pressure of blood through the dialyzer, often exactly, or in some embodiments, at least within about 1% or about 2% of the pressure of the blood. In some cases, it may be desirable to maintain a greater pressure difference (either positive or negative) between the blood flow path and dialysate flow path. After passing through the dialyzer, the used dialysate, containing waste molecules (as discussed below), is discarded in some fashion. In some cases, the dialysate is heated prior to treatment of the blood within the dialyzer using an appropriate heater, such as an electrical resistive heater. The dialysate may also be filtered to remove contaminants, infectious organisms, debris, and the like, for instance, using an ultrafilter. The ultrafilter may have a mesh or pore size chosen to prevent species such as these from passing therethrough. For instance, the mesh or pore size may be less than about 0.3 micrometers, less than about 0.2 micrometers, less than about 0.1 micrometers, or less than about 0.05 micrometers, etc. The dialysate is used to draw waste molecules (e.g., urea, creatinine, ions such as potassium, phosphate, etc.) and water from the blood into the dialysate through osmosis or convective transport, and dialysate solutions are well-known to those of ordinary skill in the art.

The dialysate typically contains various ions such as sodium chloride, bicarbonate, potassium and calcium that are similar in concentration to that of normal blood. In some cases, the bicarbonate, may be at a concentration somewhat higher than found in normal blood. Typically, the dialysate is prepared by mixing water from a water supply with one or more ingredients: an "acid" (which may contain various species such as acetic acid, dextrose, NaCl, CaCl, KCl, MgCl, etc.), sodium bicarbonate ($NaHCO_3$), and/or sodium chloride (NaCl). The preparation of dialysate, including using the appropriate concentrations of salts, osmolarity, pH, and the like, is well-known to those of ordinary skill in the art. As discussed in detail below, the dialysate need not be prepared at the same rate that the dialysate is used to treat the blood. For instance, the dialysate can be made concurrently or prior to dialysis, and stored within a dialysate storage vessel or the like.

Within the dialyzer, the dialysate and the blood typically do not come into physical contact with each other, and are separated by a semi-permeable membrane. Typically, the semipermeable membrane is formed from a polymer such as cellulose, polyarylethersulfone, polyamide, polyvinylpyrrolidone, polycarbonate, polyacrylonitrile, or the like, which allows the transport of ions or small molecules (e.g., urea, water, etc.), but does not allow bulk transport or convection during treatment of the blood. In some cases, even larger molecules, such as beta-2-microglobulin, may pass through the membrane. In other cases, convective transfer of fluid, ions and small molecules can occur, for example, when there is a hydrostatic pressure difference across the semi-permeable membrane.

The dialysate and the blood do not come into contact with each other in the dialyzer, and are usually separated by the membrane. Often, the dialyzer is constructed according to a "shell-and-tube" design comprising a plurality of individual tubes or fibers (through which blood flows), formed from the semipermeable membrane, surrounded by a larger "shell" through which the dialysate flows (or vice versa in some cases). Flow of the dialysate and the blood through the dialyzer can be countercurrent, or concurrent in some instances. Dialyzers are well-known to those of ordinary skill in the art, and are obtainable from a number of different commercial sources.

In one aspect, the dialysate flow path can be divided into one or more circuits, such as a balancing circuit, a mixing circuit, and/or a directing circuit. It should be noted that a circuit, in reference to fluid flow, is not necessarily fluidically isolated, i.e., fluid may flow into a fluid circuit and out of a fluid circuit. Similarly, a fluid may pass from one fluid circuit to another fluid circuit when the fluid circuits are in fluid communication or are fluidly connected to each other. It should be noted that, as used herein, "Fluid" means anything having fluidic properties, including but not limited to, gases such as air, and liquids such as water, aqueous solution, blood, dialysate, etc.

Hemodialysis Circuits

An example of a hemodialysis system having such fluid circuits is illustrated schematically in FIG. 1 as a high-level overview. FIG. 1 illustrates a dialysis system 5 that includes a blood flow circuit 10, through which blood passes from a patient to a dialyzer 14, and through which treated blood returns to the patient. The hemodialysis system in this example also includes a balancing circuit 143 (part of an internal or inner dialysate circuit), which takes dialysate after it passes through an ultrafilter 73 and passes the dialysate through dialyzer 14, with used dialysate returning to balancing circuit 143 from dialyzer 14. A directing circuit 142 (part of an external or outer dialysate circuit) handles fresh dialysate before it passes through ultrafilter 73. A mixing circuit 25 prepares dialysate, for instance, on an as-needed basis, during and/or in advance of dialysis, etc., using various ingredients 49 and water. The directing circuit 142 can also receive water from a water supply 30 and pass it to mixing circuit 25 for preparation of the dialysate, and the directing circuit 142 can also receive used dialysate from balancing circuit 143 and pass it out of system 5 as waste via drain 31. Also shown, in dotted lines, the blood lines connected to the patient during therapy may be connected to the directing circuit 142, e.g., for disinfection of the hemodialysis system as indicated by the dashed lines 67. In one set of embodiments, one or more of these circuits (e.g., the blood flow circuit, the balancing circuit, the directing circuit, and/or the mixing circuit) may include a cassette incorporating the valves and pumps needed for controlling flow through that portion. Examples of such systems are discussed in detail below.

Figure 2:
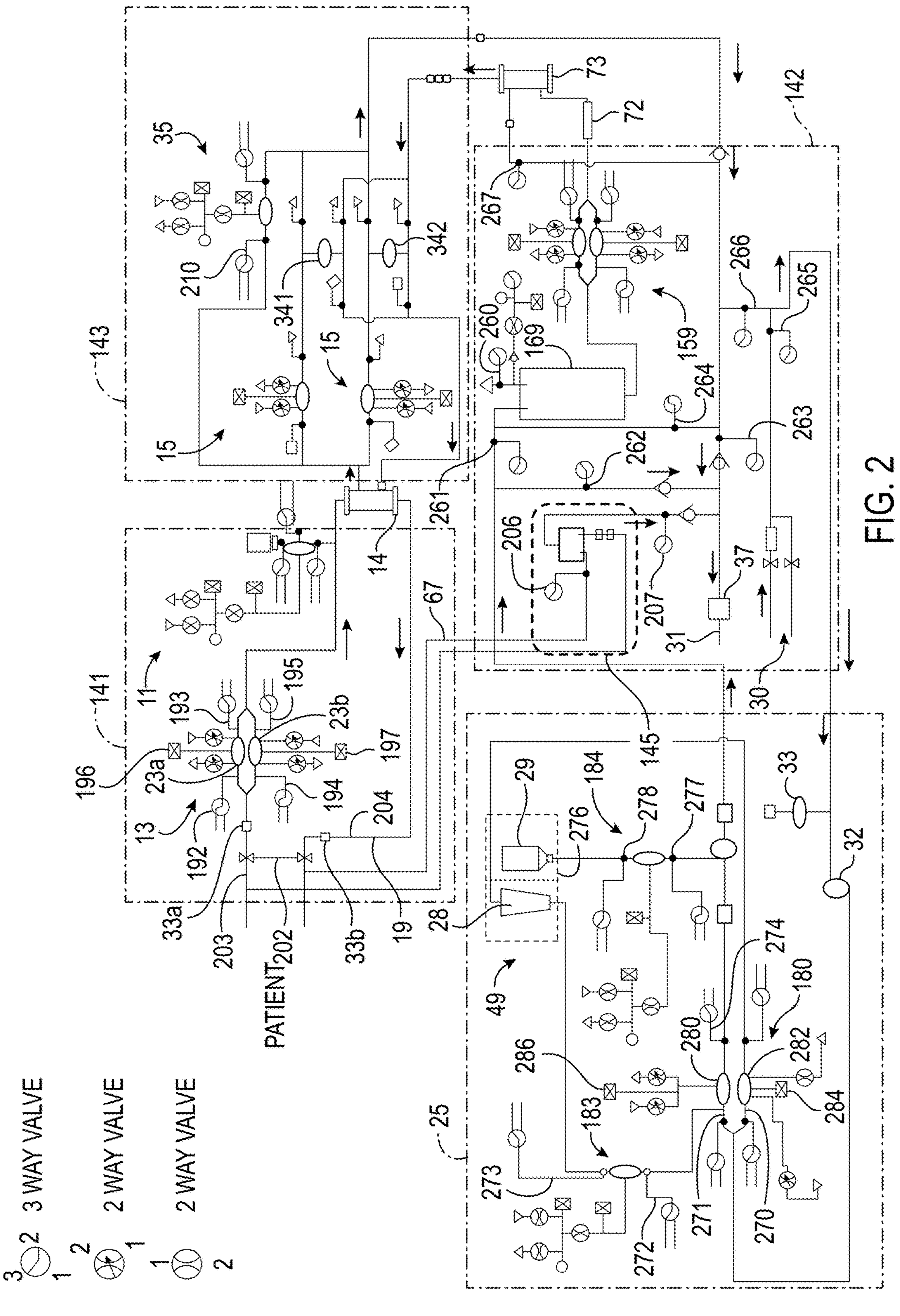
FIG. 2 is a schematic showing an example of a fluid schematic for a dialysis system.

FIG. 2 is a schematic diagram showing a specific embodiment of the general overview shown in FIG. 1. FIG. 2 shows, in detail, how a blood flow circuit 141, a balancing circuit 143, a directing circuit 142, and a mixing circuit 25 can be implemented on cassettes and made to interrelate with each other and to a dialyzer 14, an ultrafilter 73, and/or a heater 72, in accordance with one embodiment of the invention. It should be understood, of course, that FIG. 2 is only one possible embodiment of the general hemodialysis system of FIG. 1, and in other embodiments, other fluid circuits, modules, flow paths, layouts, etc. are possible. Examples of such systems are discussed in more detail below, and also can be found in the following, each of which is incorporated herein by reference: U.S. Provisional Patent Application Ser. No. 60/903,582, filed Feb. 27, 2007, entitled "Hemodialysis System and Methods"; U.S. Provisional Patent Application Ser. No. 60/904,024, filed Feb. 27, 2007, entitled "Hemodialysis System and Methods"; U.S. patent application Ser. No. 11/871,680, filed Oct. 12, 2007, entitled "Pumping Cassette"; U.S. patent application Ser. No. 11/871,712, filed Oct. 12, 2007, entitled "Pumping Cassette"; U.S. patent application Ser. No. 11/871,787, filed Oct. 12, 2007, entitled "Pumping Cassette"; U.S. patent application Ser. No. 11/871,793, filed Oct. 12, 2007, entitled "Pumping Cassette"; or U.S. patent application Ser. No. 11/871,803, filed Oct. 12, 2007, entitled "Cassette System Integrated Apparatus."

The components in FIG. 2 will be discussed in detail below. Briefly, blood flow circuit 141 includes an anticoagulant supply 11 and a blood flow pump 13 which pumps blood from a patient to a dialyzer 14. The anticoagulant supply 11, although shown in the path of blood flowing towards the dialyzer, in other embodiments, may be instead located in the path of blood flowing towards the patient, or in another suitable location, such as upstream or downstream of blood flow pump 13. The anticoagulant supply 11 may be placed in any location downstream from blood flow pump 13. Balancing circuit 143 includes two dialysate pumps 15, which also pump dialysate into dialyzer 14, and a bypass or ultrafiltration pump 35. Directing circuit 142 includes a dialysate pump 159, which pumps dialysate from dialysate tank 169 through heater 72 and/or ultrafilter 73 to the balancing circuit. Directing circuit 142 also takes waste fluid from balancing circuit 143 and directs it to a drain 31. In some cases, the blood flow circuit 141 can be connected to the directing circuit 142 via by connecting the blood lines 203, 204 to ports in the drain circuit 145 which is part of the directing circuit 142. The directing circuit 145 includes recirculation valve 206 that allows liquid to circulate through the blood circuit 141. The connecting flow paths are indicated by lines 67. The blood flow circuit 141 is connected to the directing circuit 142 for disinfection and other functions, as discussed below. Dialysate flows into dialysate tank 169 from a dialysate supply.

In certain embodiments, the invention provides methods for making dialysate from water contained within or supplied to the system and at least one supply of solutes contained within or supplied to the system. For example, as is shown in FIGS. 2, and 7A the dialysate is produced in mixing circuit 25. Water from water supply 30 flows through directing circuit 142 into mixing circuit 25. Dialysate ingredients 49 (e.g., bicarbonate and acid) are also added into mixing circuit 25, and a series of mixing pumps 180, 183, 184 are used to produce the dialysate, which is then sent to directing circuit 142. This method, and the control thereof, to ensure acceptable dialysate quality is produced and maintained during treatment is described in more detail below.

In this example system, one of the fluid circuits is a blood flow circuit, e.g., blood flow circuit 141 in FIG. 2. In the blood flow circuit, blood from a patient is pumped through a dialyzer and then is returned to the patient. In some cases, blood flow circuit is implemented on a cassette, as discussed below, although it need not be. The flow of blood through the blood flow circuit, in some cases, is balanced with the flow of dialysate flowing through the dialysate flow path, especially through the dialyzer and the balancing circuit.

Blood Circuit

Figure 3:
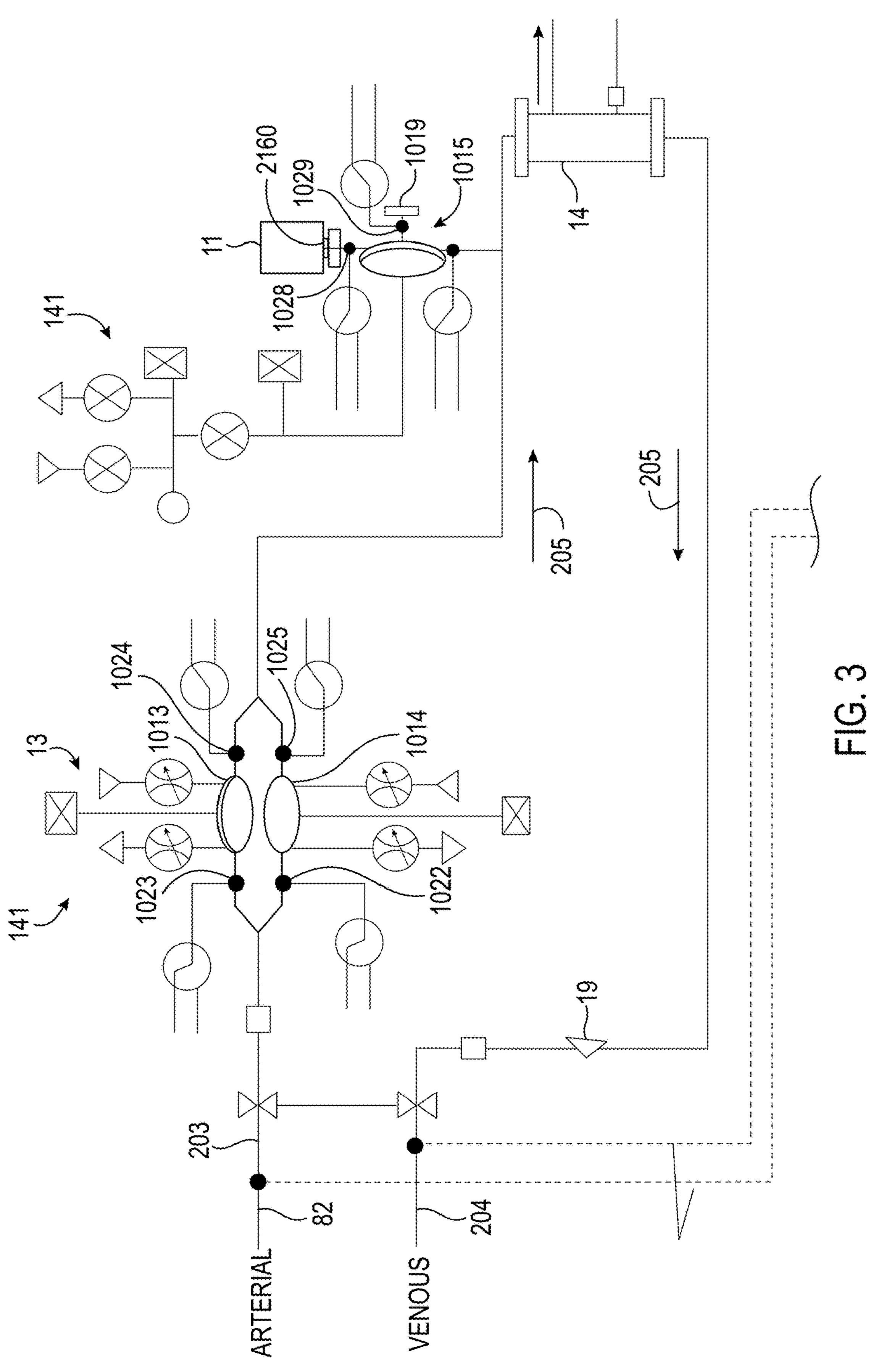
FIG. 3 is a schematic representations of an embodiments of a blood flow circuit that may be used in a hemodialysis system.

One example of a blood flow circuit is shown in FIG. 3. Generally, blood flows from a patient through arterial line 203 via blood flow pump 13 to dialyzer 14 (the direction of flow during normal dialysis is indicated by arrows 205; in some modes of operation, however, the flow may be in different directions, as discussed below). Optionally, an anticoagulant may be introduced into the blood via anticoagulant pump 80 from an anticoagulant supply. As shown in FIG. 3, the anticoagulant can enter the blood flow path after the blood has passed through blood flow pump 13; however, the anticoagulant may be added in any suitable location along the blood flow path in other embodiments. The blood pump chambers can thus additionally serve to trap air that may be present in the blood before it is pumped to the dialyzer. In other embodiments, anticoagulant supply 11 may be located anywhere downstream from the blood flow pump. After passing through dialyzer 14 and undergoing dialysis, the blood returns to the patient through venous line 204, optionally passing through air trap and/or a blood sample port 19.

As is shown in FIG. 3, blood flow cassette 141 also includes one or more blood flow pumps 13 for moving blood through the blood flow cassette. The pumps may be, for instance, pumps that are actuated by a control fluid, such as is discussed below. For instance, in one embodiment, pump 13 may comprise two (or more) pod pumps, e.g., pod pumps 23 in FIG. 3. Each pod pump, in this particular example, may include a rigid chamber with a flexible diaphragm or membrane dividing each chamber into a fluid compartment and control compartment. There are four entry/exit valves on these compartments, two on the fluid compartment and two on the control compartment. The valves on the control compartment of the chambers may be two-way proportional valves, one connected to a first control fluid source (e.g., a high pressure air source), and the other connected to a second control fluid source (e.g., a low pressure air source) or a vacuum sink. The fluid valves on the compartments can be opened and closed to direct fluid flow when the pod pumps are pumping. Non-limiting examples of pod pumps are described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," each incorporated herein by reference. Further details of the pod pumps are discussed below. If more than one pod pump is present, the pod pumps may be operated in any suitable fashion, e.g., synchronously, asynchronously, in-phase, out-of-phase, etc.

For instance, in some embodiments, the two-pump pumps can be cycled out of phase to affect the pumping cycle, e.g., one pump chamber fills while the second pump chamber empties. A phase relationship anywhere between 0° (the pod pumps act in the same direction, filling and emptying in unison) and 180° (the pod pumps act in opposite directions, in which one pod pump fills as the other empties) can be selected in order to impart any desired pumping cycle.

A phase relationship of 180° may yield continuous flow into and out of the pod pump cassette. This is useful, for instance, when continuous flow is desired, e.g., for use with dual needle flow or a "Y" or "T" connection. Setting a phase relationship of 0°, however, may be useful in some cases for single needle flow, in situations in which a "Y" or "T" connection is made with a single needle or single lumen catheter, or in other cases. In a 0° relationship, the pod pumps will first fill from the needle, then deliver blood through the blood flow path and back to the patient using the same needle. In addition, running at phases between 0° and 180° can be used in some cases, to achieve a push/pull relationship (hemodiafiltration or continuous back flush) across the dialyzer.

Blood flow circuit 141 may also include an air trap 19 incorporated into blood flow circuit 141 in some cases. Air trap 19 may be used to remove air bubbles that may be present within the blood flow path. In some cases, air trap 19 is able to separate any air that may be present from the blood due to gravity. In some cases, air trap 19 may also include a port for sampling blood. Air traps are known to those of ordinary skill in the art.

Figure 4A:
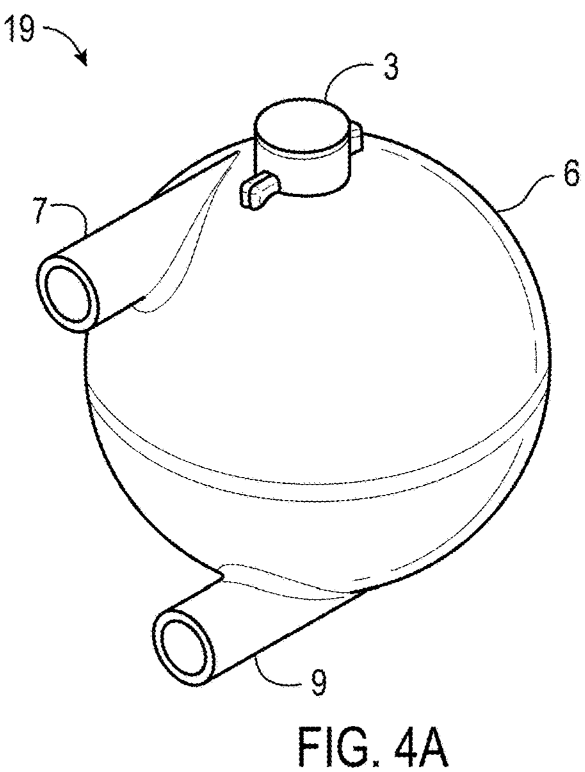
FIGS. 4A and 4B are perspective and side views, respectively, of the air trap in FIG. 3.
Figure 4B:
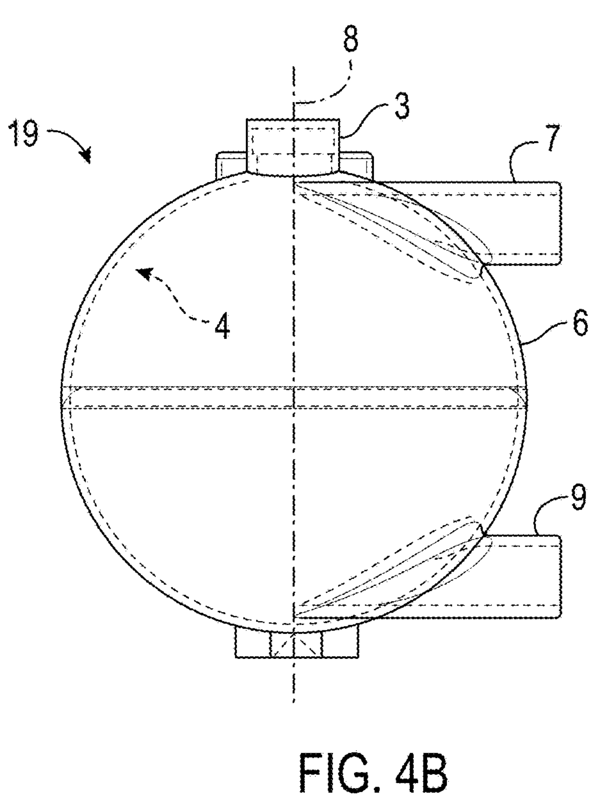

In accordance with another aspect of the invention, the air trap 19 is placed in the blood flow path after the blood exits the dialyzer and before it is returned to the patient. As shown in FIGS. 4A and 4B, air trap 19 may have a spherical or spheroid-shape container 6, and have its inlet port 7 located near the top and offset from the vertical axis of the container, and an outlet 9 at a bottom of the container. The curved shape of the inside wall 4 of the trap can thus direct the blood to circulate along the inside wall as the blood gravitates to the bottom of the container, facilitating the removal of air bubbles from the blood. Referring now to FIG. 3, air present in the blood exiting the outlet 9 of the dialyzer 14 will enter at the top of the air trap 19 and remain at the top of the container as blood flows out the outlet at the bottom and to the venous blood line 204. Referring again to FIGS. 4A, 4B, by locating the inlet port 7 near the top of trap 19, it is also possible to circulate blood through the trap with minimal or no air present within the container (as a "run-full" air trap). The ability to avoid an air-blood interface for routine circulation of blood in the trap can be advantageous. Placing the inlet port 7 at or near the top of the container also allows most or all of the air present in the trap to be removed from the trap by reversing the flow of fluid through the blood tubing (i.e. from the bottom to the top of the trap 19, exiting through the inlet port of the trap 19). In an embodiment, a self-sealing port 3, such as a self-sealing stopper with a split septum or membrane, or another arrangement, is located at the top of the trap, allowing the withdrawal of air from the container (e.g., by syringe). The blood-side surface of the self-sealing membrane can be situated nearly flush with the top of the interior of the trap, in order to facilitate cleaning of the self-sealing port during disinfection. The self-sealing port 3 can also serve as a blood sampling site, and/or to allow the introduction of liquids, drugs or other compounds into the blood circuit. A sealed rubber-type stopper can be used if access with a needle is contemplated. Using a self-sealing stopper with split septum permits sampling and fluid delivery using a needleless system.

Additional fluid connections 82 may allow the blood flow circuit 141 to also be connected to the patient. Generally, during disinfection, arterial line 203 and venous line 204 are connected directly to directing circuit 142 as indicated by lines 67, such that a disinfecting fluid (e.g., heated water and in some embodiments, a combination heated water and one or more chemical agent) may be flowed through dialyzer 14 and blood flow circuit 141 back to directing circuit 142 for recirculation, this disinfection is similar to those shown in U.S. Pat. No. 5,651,898 to Kenley, et al., which is incorporated herein by reference. This is also discussed in more detail below.

The pressure within arterial line 203, to draw blood from the patient, may be kept to a pressure below atmospheric pressure in some cases. If a pod pump is used, the pressure within blood flow pump 13 may be inherently limited to the pressures available from the positive and negative pressure reservoirs used to operate the pump. In the event that a pressure reservoir or valve fails, the pump chamber pressure will approach the reservoir pressure. This will increase the fluid pressure to match the reservoir pressure until the diaphragm within the pod pump "bottoms" (i.e., is no longer is able to move, due to contact with a surface), and the fluid pressure will not exceed a safe limit and will equilibrate with a natural body fluid pressure. This failure naturally stops operation of the pod pump without any special intervention.

A system of the present invention may also include a balancing circuit, e.g., balancing circuit 143 as shown in FIG. 2. In some cases, blood flow circuit is implemented on a cassette, although it need not be. Within the balancing circuit, the flow of dialysate that passes in and out of the dialyzer may be balanced in some cases such that essentially the same amount of dialysate comes out of the dialyzer as goes into it (however, this balance can be altered in certain cases, due to the use of a ultrafiltration pump, as discussed below). In addition, in some cases, the flow of dialysate may also be balanced through the dialyzer such that the pressure of dialysate within the dialyzer generally equals the pressure of blood through the blood flow circuit.

Balance Circuit

Figure 5:
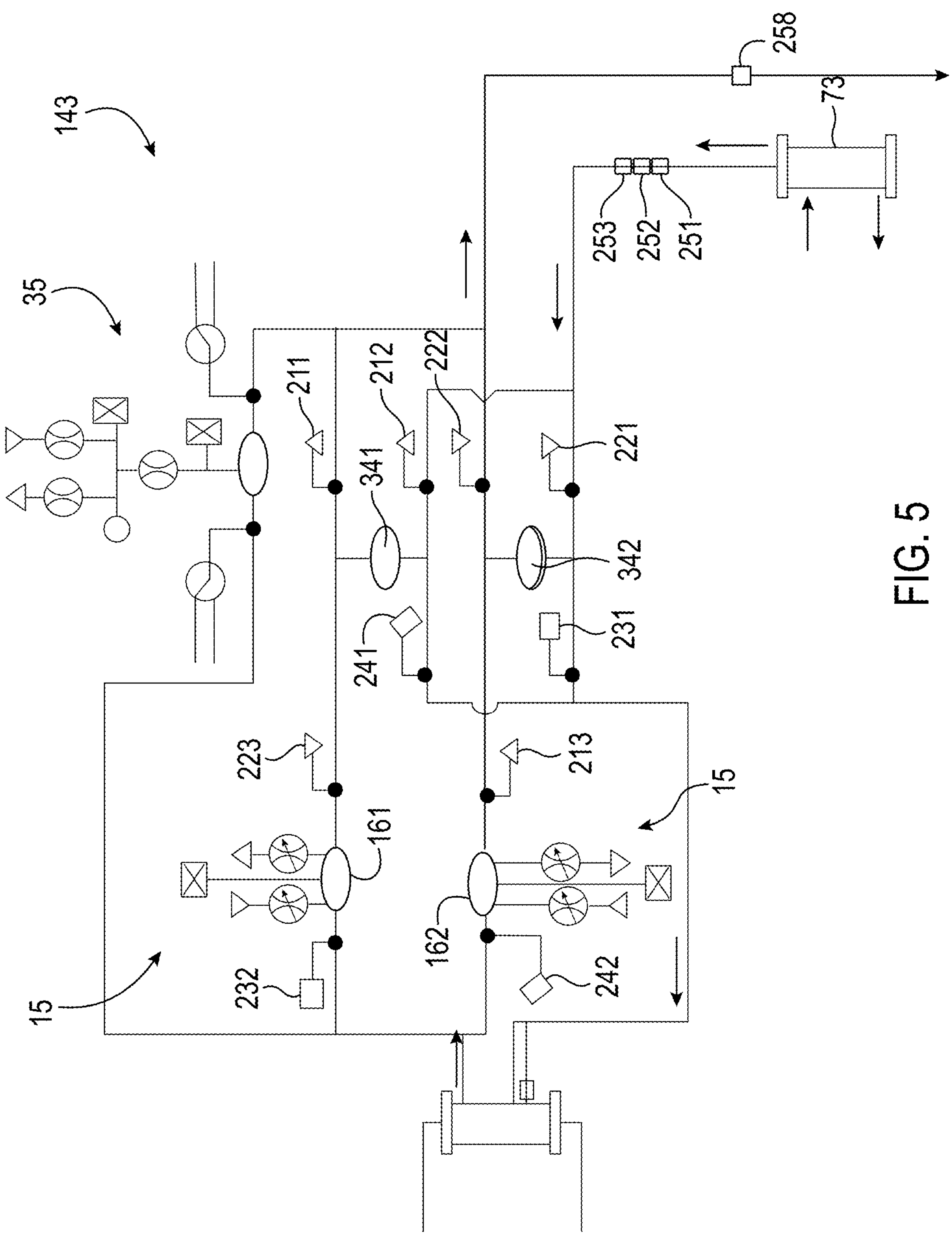
FIG. 5 is a schematic representation of one embodiment of a balancing circuit that may be used in a hemodialysis system.

A non-limiting example of a balancing circuit is shown in FIG. 5. In balancing circuit 143, dialysate flows from optional ultrafilter 73 into one or more dialysate pumps 15 (e.g., two as shown in FIG. 5). The dialysate pumps 15 in this figure include two pod pumps 161, 162, two balancing chambers 341, 342, and an ultrafiltration pump 35 for bypassing the balancing chambers. The balancing chambers may be constructed such that they are formed from a rigid chamber with a flexible diaphragm dividing the chamber into two separate fluid compartments, so that entry of fluid into one compartment can be used to force fluid out of the other compartment and vice versa. Non-limiting examples of pumps that can be used as pod pumps and/or balancing chambers are described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," each incorporated herein by reference. Additional examples of pod pumps are discussed in detail below. As can be seen in the schematic of FIG. 5, many of the valves can be "ganged" or synchronized together in sets, so that all the valves in a set can be opened or closed at the same time.

Ganged Valves in Balance Circuit

More specifically, in one embodiment, balancing of flow works as follows. FIG. 5 includes a first synchronized, controlled together set of valves 211, 212, 213, 241, 242, where valves 211, 212, 213 are ganged and valves 241 and 242 are ganged, as well as a second synchronized, controlled together set of valves 221, 222, 223, 231, 232, where valves 221, 222, 223 are ganged, and valves 231 and 232 are ganged. At a first point of time, the first ganged set of valves 211, 212, 213, 241, 242 is opened while the second ganged set of valves 221, 222, 223, 231, 232 is closed. Fresh dialysate flows into balancing chamber 341 while used dialysate flows from dialyzer 14 into pod pump 161. Fresh dialysate does not flow into balancing chamber 342 since valve 221 is closed. As fresh dialysate flows into balancing chamber 341, used dialysate within balancing chamber 341 is forced out and exits balancing circuit 143 (the used dialysate cannot enter pod pump 161 since valve 223 is closed). Simultaneously, pod pump 162 forces used dialysate present within the pod pump into balancing chamber 342 (through valve 213, which is open; valves 242 and 222 are closed, ensuring that the used dialysate flows into balancing chamber 342). This causes fresh dialysate contained within balancing chamber 342 to exit the balancing circuit 143 into dialyzer 14. Also, pod pump 161 draws in used dialysate from dialyzer 14 into pod pump 161.

Once pod pump 161 and balancing chamber 341 have filled with dialysate, the first set of valves 211, 212, 213, 241, 242 is closed and the second set of valves 221, 222, 223, 231, 232 is opened. Fresh dialysate flows into balancing chamber 342 instead of balancing chamber 341, as valve 212 is closed while valve 221 is now open. As fresh dialysate flows into balancing chamber 342, used dialysate within the chamber is forced out and exits balancing circuit, since valve 213 is now closed. Also, pod pump 162 now draws used dialysate from the dialyzer into the pod pump, while used dialysate is prevented from flowing into pod pump 161 as valve 232 is now closed and valve 222 is now open. Pod pump 161 forces used dialysate contained within the pod pump (from the previous step) into balancing chamber 341, since valves 232 and 211 are closed and valve 223 is open. This causes fresh dialysate contained within balancing chamber 341 to be directed into the dialyzer (since valve 241 is now open while valve 212 is now closed). At the end of this step, pod pump 162 and balancing chamber 342 have filled with dialysate. This puts the state of the system back into the configuration at the beginning of this description, and the cycle is thus able to repeat, ensuring a constant flow of dialysate to and from the dialyzer. In an embodiment, the fluid (e.g. pneumatic) pressures on the control side of the balancing chamber valves are monitored to ensure they are functioning properly.

As a specific example, the first ganged set of valves are exposed to atmospheric pressure, causing those valves to open, while positive pressure (e.g., 20 p.s.i. of air pressure, 1 psi is 6.89475 kilopascals) is applied to the second ganged set of valves, causing those valves to close (or vice versa). The pod pumps each urge dialysate into one of the volumes in one of the balancing chambers 341, 342. By forcing dialysate into a volume of a balancing chamber, an equal amount of dialysate is squeezed by the diaphragm out of the other volume in the balancing chamber. In each balancing chamber, one volume is occupied by fresh dialysate heading towards the dialyzer and the other volume is occupied by used dialysate heading from the dialyzer. Thus, the volumes of dialysate entering and leaving the dialyzer are kept substantially equal.

As the diaphragms approach a wall in the balancing chambers (so that one volume in a balancing chamber approaches a minimum and the other volume approaches a maximum), positive pressure is applied to the port for the first ganged set of valves, causing those valves to close, while a vacuum is applied to the second ganged set of valves, causing those valves to open. The pod pumps then each urge dialysate into one of the volumes in the other of the balancing chambers 341, 342. Again, by forcing dialysate into a volume of a balancing chamber, an equal amount of dialysate is squeezed by the diaphragm out of the other volume in the balancing chamber. Since, in each balancing chamber, one volume is occupied by fresh dialysate heading towards the dialyzer and the other volume is occupied by used dialysate heading from the dialyzer, the volumes of dialysate entering and leaving the dialyzer are kept equal.

Ultrafiltration Pump in Balance Circuit

Also shown within FIG. 5 is bypass or ultrafiltration pump 35, which can direct the flow of dialysate from dialyzer 14 through balancing circuit 143 without passing through either of pod pumps 161 or 162. In this figure, ultrafiltration pump 35 is a pod pump, similar to those described above, with a rigid chamber and a flexible diaphragm dividing each chamber into a fluid compartment and a control compartment. This pump may be the same or different from the other pod pumps, metering pumps and/or balancing chambers described above. For example, this pump may be a pump as was described in U.S. Provisional Patent Application Ser. No. 60/792,073, filed Apr. 14, 2006, entitled “Extracorporeal Thermal Therapy Systems and Methods”; or in U.S. patent application Ser. No. 11/787,212, filed Apr. 13, 2007, entitled “Fluid Pumping Systems, Devices and Methods,” each incorporated herein by reference. Pod pumps are also discussed in detail below.

When control fluid is used to actuate the ultrafilter this pump, dialysate may be drawn through the dialyzer in a way that is not balanced with respect to the flow of blood through the dialyzer. The independent action of the ultrafiltration pump 35 on the dialysate outlet side of the dialyzer causes an additional net ultrafiltration of fluid from the blood in the dialyzer. This may cause the net flow of liquid away from the patient, through the dialyzer, towards the drain. Such a ultrafiltration may be useful, for example, in reducing the amount of fluid a patient has, which is often increased due to the patient’s inability to lose fluid (primarily water) through the kidneys. As shown in FIG. 5, ultrafiltration pump 35 may be controlled by a control fluid (e.g., air), irrespective of the operation of pod pumps 161 and 162. This configuration may allow for easier control of net fluid removal from a patient, without the need to operate the balancing pumps (inside and outside dialysate pumps) in a way that would allow for such fluid to be withdrawn from the patient. Using this configuration, it is not necessary to operate the inside dialysate pumps either out of balance or out of phase with the blood pumps in order to achieve a net withdrawal of fluid from the patient.

To achieve balanced flow across the dialyzer, the blood flow pump, the pumps of the balancing circuit, and the pumps of the directing circuit (discussed below) may be operated to work together to ensure that flow into the dialyzer is generally equal to flow out of the dialyzer. If ultrafiltration is required, the ultrafiltration pump (if one is present) may be run independently of some or all of the other blood and/or dialysate pumps to achieve the desired ultrafiltration rate.

To prevent outgassing of the dialysate, the pumps of the balancing circuit may be always kept at pressures at or above atmospheric pressure. In contrast, however, the blood flow pump and the directing circuit pumps use pressures below atmosphere to pull the diaphragm towards the chamber wall for a fill stroke. Because of the potential of fluid transfer across the dialyzer and because the pumps of the balancing circuit run at positive pressures, the balancing circuit pumps may be able to use information from the blood flow pump(s) in order to run in a balanced flow mode. The delivery strokes of the balancing circuit chambers to the dialyzer may be synchronized with the delivery strokes of the blood pumps.

In one set of embodiments, when running in such a balanced mode, if there is no delivery pressure from the blood flow pump, the balancing circuit pump diaphragm will push fluid across the dialyzer into the blood and the alternate pod of the balancing circuit will not completely fill. For this reason, the blood flow pump reports when it is actively delivering a stroke. When the blood flow pump is delivering a stroke the balancing pump operates. When the blood flow pump is not delivering blood, the valves that control the flow from the dialyzer to the balancing pumps (and other balancing valves ganged together with these valves, as previously discussed) may be closed to prevent any fluid transfer from the blood side to the dialysate side from occurring. During the time the blood flow pump is not delivering, the balancing pumps are effectively frozen, and the stroke continues once the blood flow pump starts delivering again. The balancing pump fill pressure can be set to a minimal positive value to ensure that the pump operates above atmosphere at minimal impedance. Also, the balancing pump delivery pressure can be set to the blood flow pump pressure to generally match pressures on either side of the dialyzer, minimizing flow across the dialyzer during delivery strokes of the inside pump.

Directing Circuit

Figure 6:
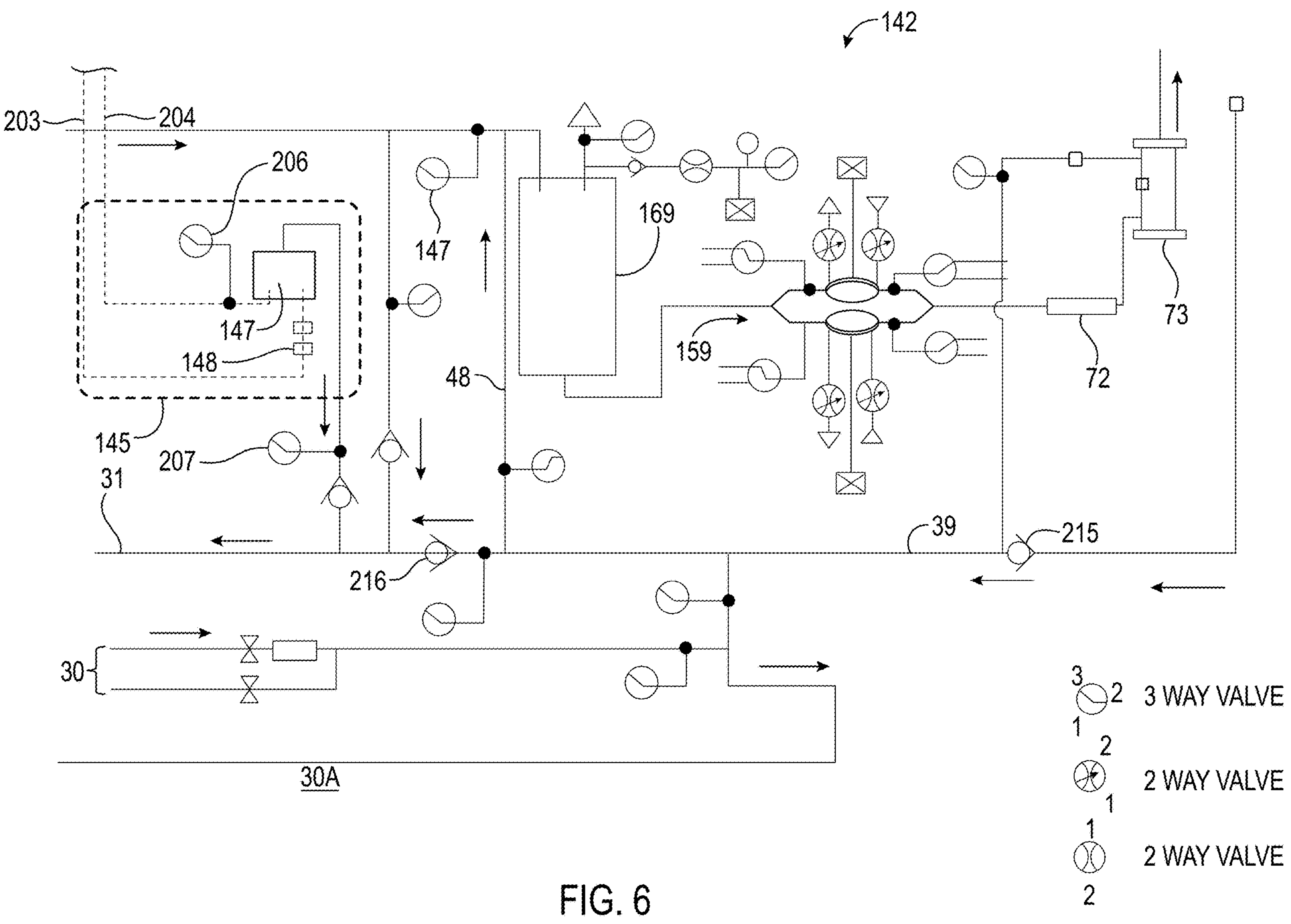
FIG. 6 is a schematic representation of a directing circuit that may be used in a hemodialysis system.

One non-limiting example of a directing circuit is shown in FIG. 6. In this figure, directing circuit 142 fluidically connects dialysate from a dialysate supply to a dialysate tank 169, then through dialysate pump 159, heater 72, and ultrafilter 73, before entering a balancing circuit, as previously discussed. Additionally, the directing circuit 142 connects the water inlet 30 to the mixing circuit via line 30A. The directing circuit 142 also fluidly connects the drain lines 39 to the inlet line 30A of the mixing circuit. The connection of the drain line 39 to the inlet line 30A allows liquid to be circulated through the dialysate circuits 25, 142, 143, of FIG. 2.

It should be understood that although this figure shows that dialysate in the dialysate flow path flows from the dialysate supply to the dialysate tank, the pump, the heater, and the ultrafilter (in that order), other orderings are also possible in other embodiments. Heater 72 may be used to warm the dialysate to body temperature, and/or a temperature such that the blood in the blood flow circuit is heated by the dialysate, and the blood returning to the patient is at body temperature or higher. Ultrafilter 73 may be used to remove any pathogens, pyrogens, etc. which may be in the dialysate solution, as discussed below. The dialysate solution then flows into the balancing circuit to be directed to the dialyzer.

Dialysate tank 169 may comprise any suitable material and be of any suitable dimension for storing dialysate prior to use. For instance, dialysate tank 169 may comprise plastic, metal, etc. In some cases, dialysate tank may comprise materials similar to those used to form the pod pumps as discussed herein.

The drain circuit 145 is sub-part of the directing circuit 142. The drain circuit 145 receives the arterial line 203 and venous blood line 204 from the blood circuit 141 during non-therapy operations such as priming, cleaning and disinfecting, when it is desired to circulate flow through the blood circuit or drain the blood circuit or prime the blood circuit. In FIG. 6 and others, the connection of the arterial and venous lines is indicated by lines 67. The Drain circuit 145 includes a recirculation valve 206 that may be opened during various the non-therapy operations including priming, cleaning and disinfection. The drain circuit 145 includes a chamber/air trap that is fluidly connected to both blood lines 203 204 and to the drain 31 via the BTS drain valve 207. In some embodiments, the drain circuit 145 includes sensors 148. The sensors may conductivity sensor probes and a temperature sensor probe. One of the conductivity probes may include the temperature sensor probe. In one example, the temperature probe may be a thermistor thermally connected to one of the conductivity probes.

The flow of dialysate through directing circuit 142 may be controlled (at least in part) by operation of dialysate pump 159. In addition, dialysate pump 159 may control flow through the balancing circuit. For instance, as discussed above with reference to FIG. 5, fresh dialysate from the directing circuit flows into balancing chambers 341 and 342 on balancing circuit 143; pump 159 may be used as a driving force to cause the fresh dialysate to flow into these balancing chambers. In one set of embodiments, dialysate pump 159 includes a pod pump, similar to those described above. The pod pump may include a rigid chamber with a flexible diaphragm dividing each chamber into a fluid compartment and control compartment. The control compartment may be connected to a control fluid source, such as an air source. Non-limiting examples of pumps that may be used as pod pumps and/or balancing chambers are described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," each incorporated herein by reference. Pod pumps are also discussed in detail below.

After passing through pump 159, the dialysate may flow to a heater, e.g., heater 72 in FIG. 6. The heater may be any heating device suitable for heating dialysate, for example, an electrically resistive heater as is known to those of ordinary skill in the art. The heater may be kept separated from the directing circuit (e.g., as is shown in FIG. 3A), or the heater may be incorporated into the directing circuit, or other circuits as well (e.g., the balancing circuit).

Mixing Circuit

Figure 7:
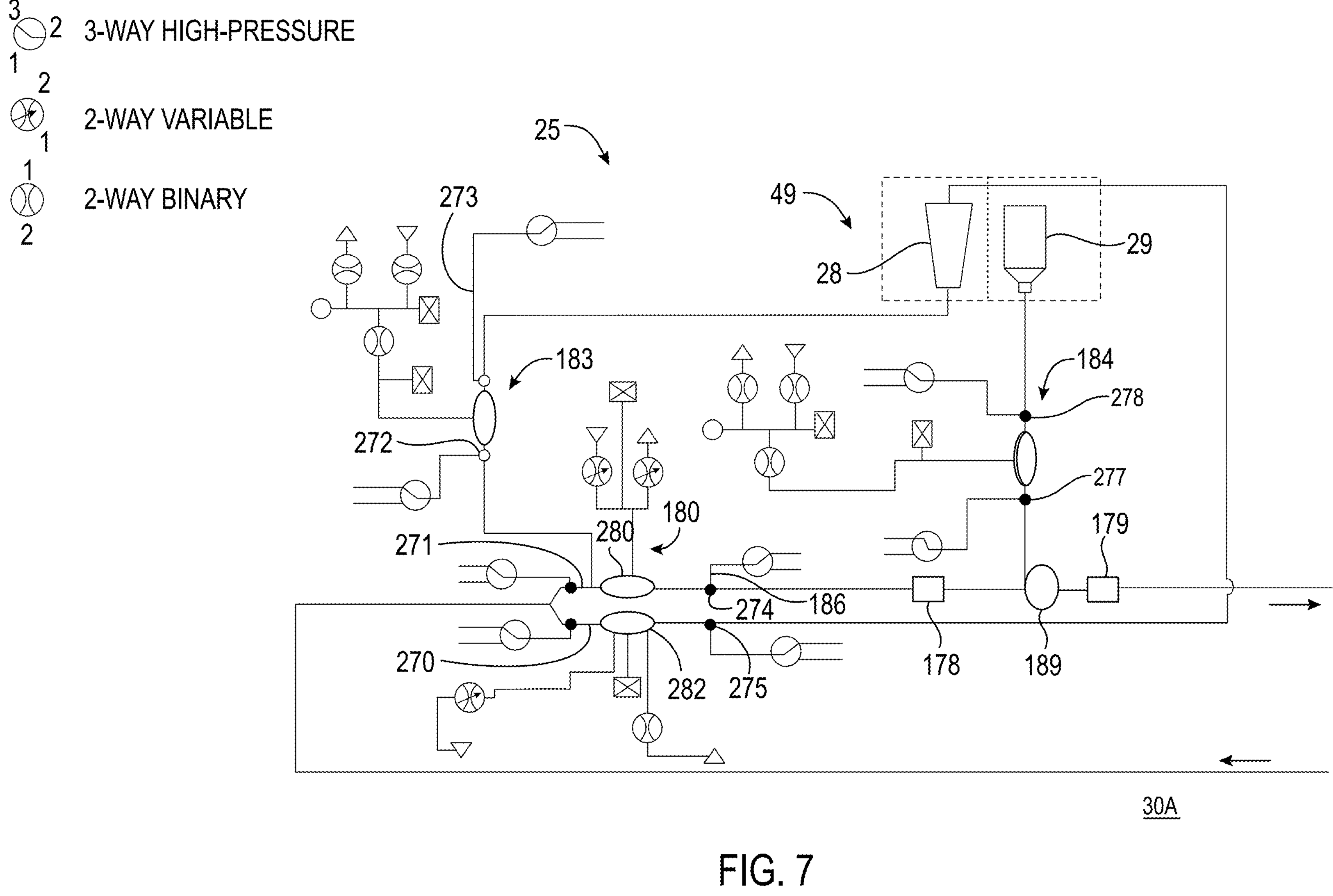
FIG. 7 is a schematic representation of a mixing circuit that may be used in a hemodialysis system.

FIG. 7 illustrates a non-limiting example of a mixing circuit, which may be implemented on a cassette in some cases. In FIG. 7, water from a directing circuit flows into mixing circuit 25 via inlet line 30A. The flow of water through the inlet line is due to action of pump 180. In some cases, a portion of the water is directed to ingredients 49, e.g., for use in transporting the ingredients through the mixing circuit. As shown in FIG. 7, water is delivered to bicarbonate source 28 (which may also contain sodium chloride in some cases). The sodium chloride and/or the sodium bicarbonate may be provided, in some cases, in a powdered or granular form, which is moved through the action of water. Bicarbonate from bicarbonate source 28 is delivered via bicarbonate pump 183 to a mixing line 186, to which water from the directing circuit also flows. Acid from acid source 29 (which may be in a liquid form) is also pumped via acid pump 184 to mixing line 186. The ingredients (water, bicarbonate, acid, NaCl, etc.) are mixed in mixing chamber 189 to produce dialysate, which then flows out of mixing circuit 25. Conductivity sensors 178 and 179 are positioned along mixing line 186 to ensure that as each ingredient is added to the mixing line, it is added at proper concentrations. This method, and the control thereof, to ensure acceptable dialysate quality is produced and maintained during treatment is described in more detail below.

In one set of embodiments, pump 180 comprises one or more pod pumps, similar to those described above. The pod pumps may include a rigid chamber with a flexible diaphragm dividing each chamber into a fluid compartment and control compartment. The control compartment may be connected to a control fluid source, such as an air source. Non-limiting examples of pumps that can be used as pod pumps are described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," each incorporated herein by reference. Similarly, in some cases, pumps 183 and/or 184 may each be pod pumps. Additional details of pod pumps are discussed below.

In some cases, one or more of the pumps may have pressure sensors to monitor the pressure in the pump. This pressure sensor may be used to ensure that a pump compartment is filling and delivering completely. For example, ensuring that the pump delivers a full stroke of fluid may be accomplished by (i) filling the compartment, (ii) closing both fluid valves, (iii) applying pressure to the compartment by opening the valve between the positive pneumatic reservoir and the compartment, (iv) closing this positive pressure valve, leaving pressurized air in the path between the valve and the compartment, (v) opening the fluid valve so the fluid can leave the pump compartment, and (vi) monitoring the pressure drop in the compartment as the fluid leaves. The pressure drop corresponding to a full stroke may be consistent, and may depend on the initial pressure, the hold-up volume between the valve and the compartment, and/or the stroke volume. However, in other embodiments of any of the pod pumps described herein, a reference volume compartment may be used, where the volume is determined through pressure and volume data.

The volumes delivered by the water pump and/or the other pumps may be directly related to the conductivity measurements, so the volumetric measurements may be used as a cross-check on the composition of the dialysate that is produced. This may ensure that the dialysate composition remains safe even if a conductivity measurement becomes inaccurate during a therapy.

Pneumatic Diaphragm Valves and Pumps

Figure 8A:
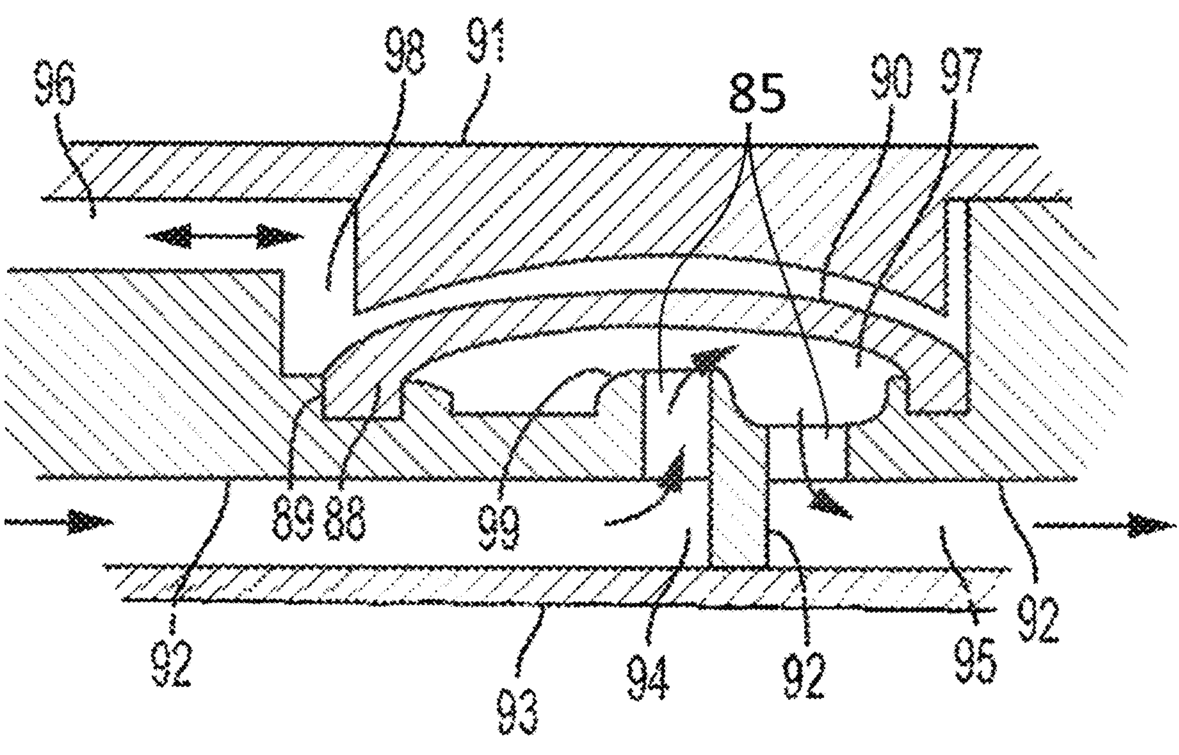
FIG. 8A is a sectional view of a diaphragm volcano valve that may be incorporated into embodiments of the fluid-control cassettes.
Figure 8B:
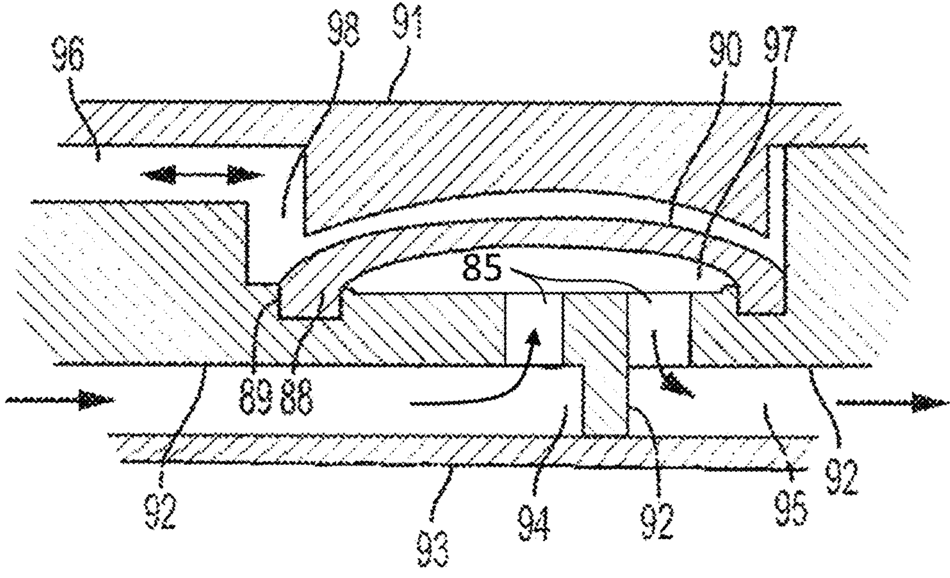
FIG. 8B is a sectional view of a diaphragm smooth valve that may be incorporated into embodiments of the fluid-control cassettes.

Non-limiting examples of pneumatic diaphragm valves are shown in FIGS. 8A, 8B. This figure is a sectional view of a pneumatically controlled valve that may be used in embodiments of the cassettes. "Pneumatic," as used herein, means using air or other gas to move a flexible diaphragm or other member. Three rigid pieces are used, a "top" plate 91, a mid-plate 92, and a "bottom" plate. (The terms "top" and "bottom" only refer to the orientation shown in FIGS. 8A, 8B. The valve may be oriented in any direction in actual use.) The top and bottom plates 91, 93 may be flat on both sides, while the mid-plate 92 is provided with channels, indentations and holes to define the various fluid paths, chamber and ports. A diaphragm 90, along with the mid-plate 92, defines a valving chamber 97. The diaphragm 90 closes the valve by sealing against at least one of the ports 85 in the mid-plate to stop flow between channel 94 and channel 95. Pneumatic pressure is provided through a pneumatic port 96 to either force, with positive gas pressure, the diaphragm 90 against the mid-plate 92 to close the valve, or to draw, with negative gas pressure, the diaphragm away from the valve seat to open the valve. The mid-plate 92 in FIG. 8A includes a port with a raised lip also called a volcano port 99 which makes the diaphragm valve a diaphragm volcano valve. In the diaphragm volcano valve of FIG. 8A, the diaphragm 90 seals against the raised lip 99 to close the valve. The mid-plate 92 in FIG. 8B has a smooth surface that the diaphragm seals against and closes the valve. In some examples, the raised lip 99 may result in turbulence in the liquid flow and create zones of recirculating liquid. Recirculating zones in blood fluid circuits 141 are sometimes associated with thrombosis and can lead to leaking valves and or obstructions in the fluid circuit.

A control gas chamber 98 is defined by the diaphragm 90, the top plate 91, and the mid-plate 92. The mid-plate 92 has an indentation formed on it, into which the diaphragm 90 is placed so as to form the control gas chamber 98 on one side of the diaphragm and the valving chamber 97 on the other side.

The pneumatic port 96 is defined by a channel formed on the "top" surface of the mid-plate 92, along with the top plate 91. By providing fluid communication between several valving chambers in a cassette, valves may be ganged together so that all the valves ganged together may be opened or closed at the same time by a single source of pneumatic pressure. Channels formed on the "bottom" surface of the mid-plate 92, along with the bottom plate, define the valve inlet channel 94 and the valve outlet channel 95. Holes 85 formed through the mid-plate 92 provide communication between the inlet channel 94 and the valving chamber 97 (through the valve seat 99) and between the valving chamber and the outlet channel 95.

The diaphragm 90 is provided with a thickened rim 88, which fits tightly in a groove 89 in the mid-plate 92. Thus, the diaphragm 90 may be placed in and held by the groove 88 before the top plate 91 is laser welded to the mid-plate 92, so the diaphragm will not interfere with the ultrasonic welding of the two plates together, and so that the diaphragm does not depend on the two plates being laser welded together in just the right way to be held in place. Thus, this valve may be manufactured easily without relying on ultrasonic welding to be done to very tight tolerances. As shown in FIGS. 8, 9, the top plate 91 may include additional material extending into control gas chamber 98 so as to prevent the diaphragm 90 from being urged too much in a direction away from the groove 89, so as to prevent the diaphragm's thickened rim 88 from popping out of the groove 89. In another example, the bottom plate 93 and or the top plate may be ultrasonically welded to the mid-plate 92.

Pressure sensors may be used to monitor pressure in the pods. For instance by alternating applied air pressure to the pneumatic side of the chamber, the diaphragm is cycled back and forth across the total chamber volume. With each cycle, fluid is drawn through the upstream valve of the inlet fluid port when the pneumatics pull a vacuum on the pods. The fluid is then subsequently expelled through the outlet port and the downstream valve when the pneumatics deliver positive pressure to the pods.

Figures 9A, 9B, 9C, 9D, 9E, 9F, 9G:
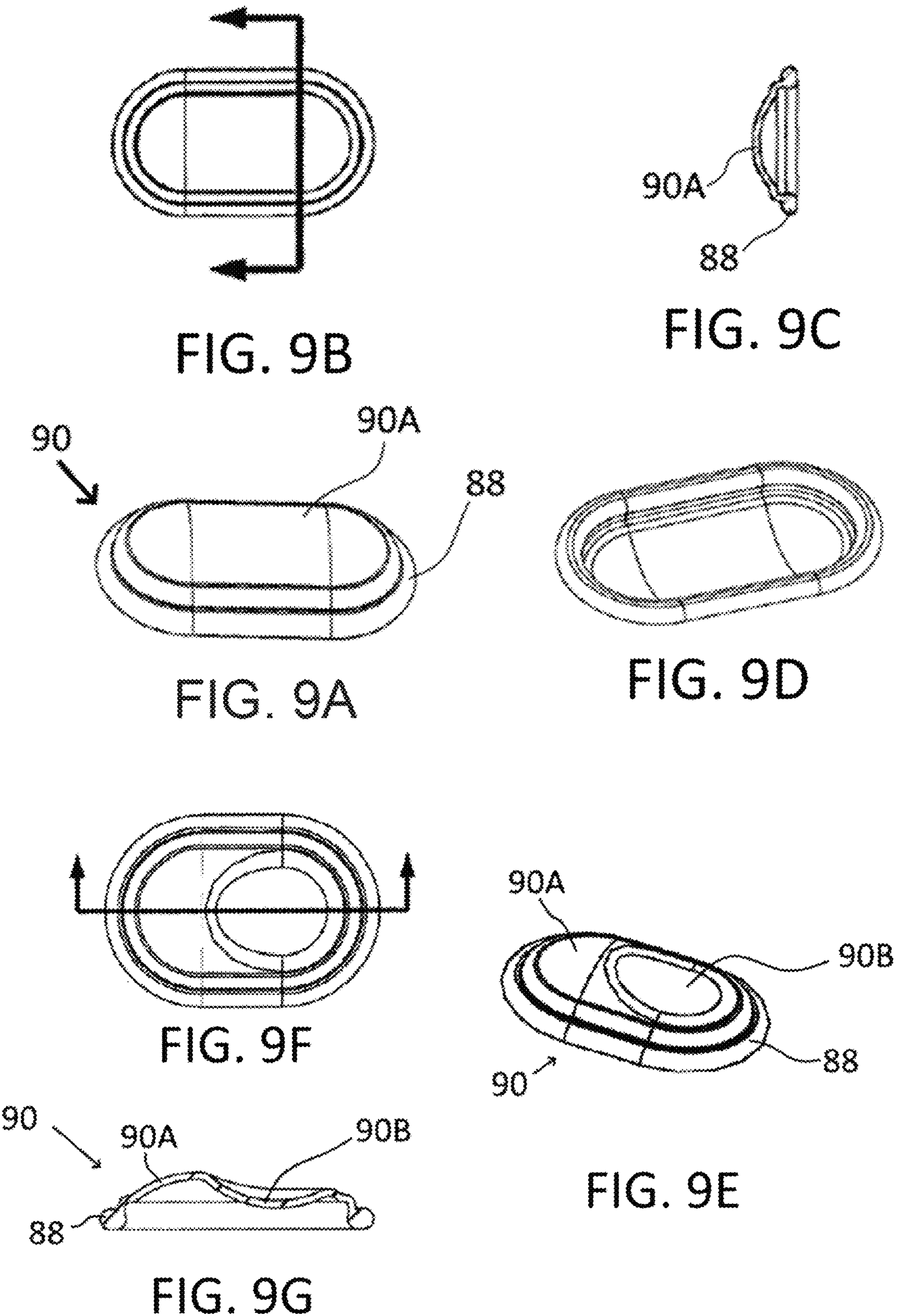
FIG. 9A shows isometric, top side and cross sectional views of one embodiment of a valving diaphragm for a smooth valve.
FIG. 9B shows isometric, top and cross sectional views of one embodiment of the valving diaphragm for a volcano valve.

The valve diaphragms 90 may be different for the smooth valve of FIG. 8B and the volcano valve of FIG. 8A. Referring now to FIGS. 9A, the valve diaphragm 90 for a smooth valve may have the form of an elongated dome 90A with a thickened edge or bead 88 at the outer edge. The elongated dome 90A is formed to create a space above the ports 85 in the assembled valve. In an embodiment, the raised dome shape of the smooth valve in FIG. 9A hold the valve open when the pressure in the control chamber 98 is atmospheric or less. Referring now to FIG. 9B, the valve diaphragm 90 for a volcano valve may have a concave region 90B within the convex dome 90A. In one example, the concave region 90B is oriented over the raised lip 99 of the volcano valve to improve the sealing of the valve. In one example, the concave region may only open when the applied pressure in the control chamber 98 is less than a predetermined negative pressure. At higher pressures, the concave region seals against the raised lip 99.

Figure 10A:
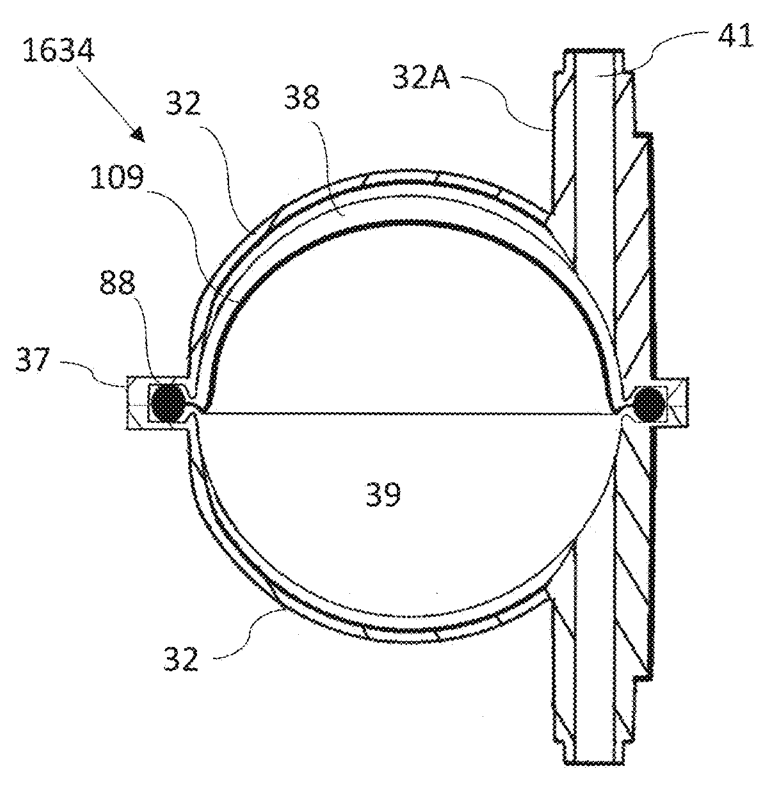
FIG. 10A is a cross-sectional view of a pneumatic diaphragm pod pump.
Figure 40:
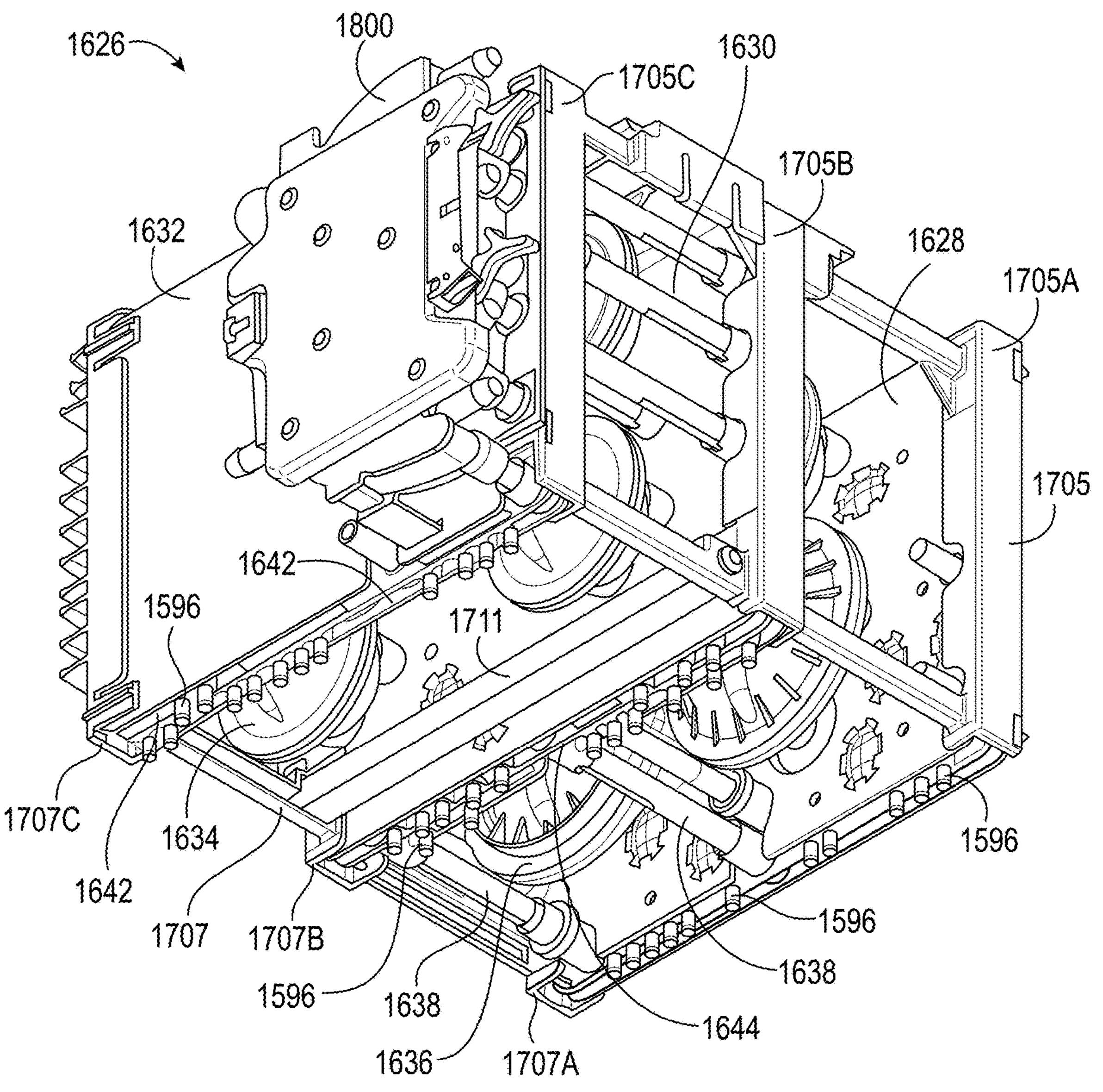
FIG. 40 is a perspective view of an exemplary cassette assembly secured in a frame assembly.
Figure 41:
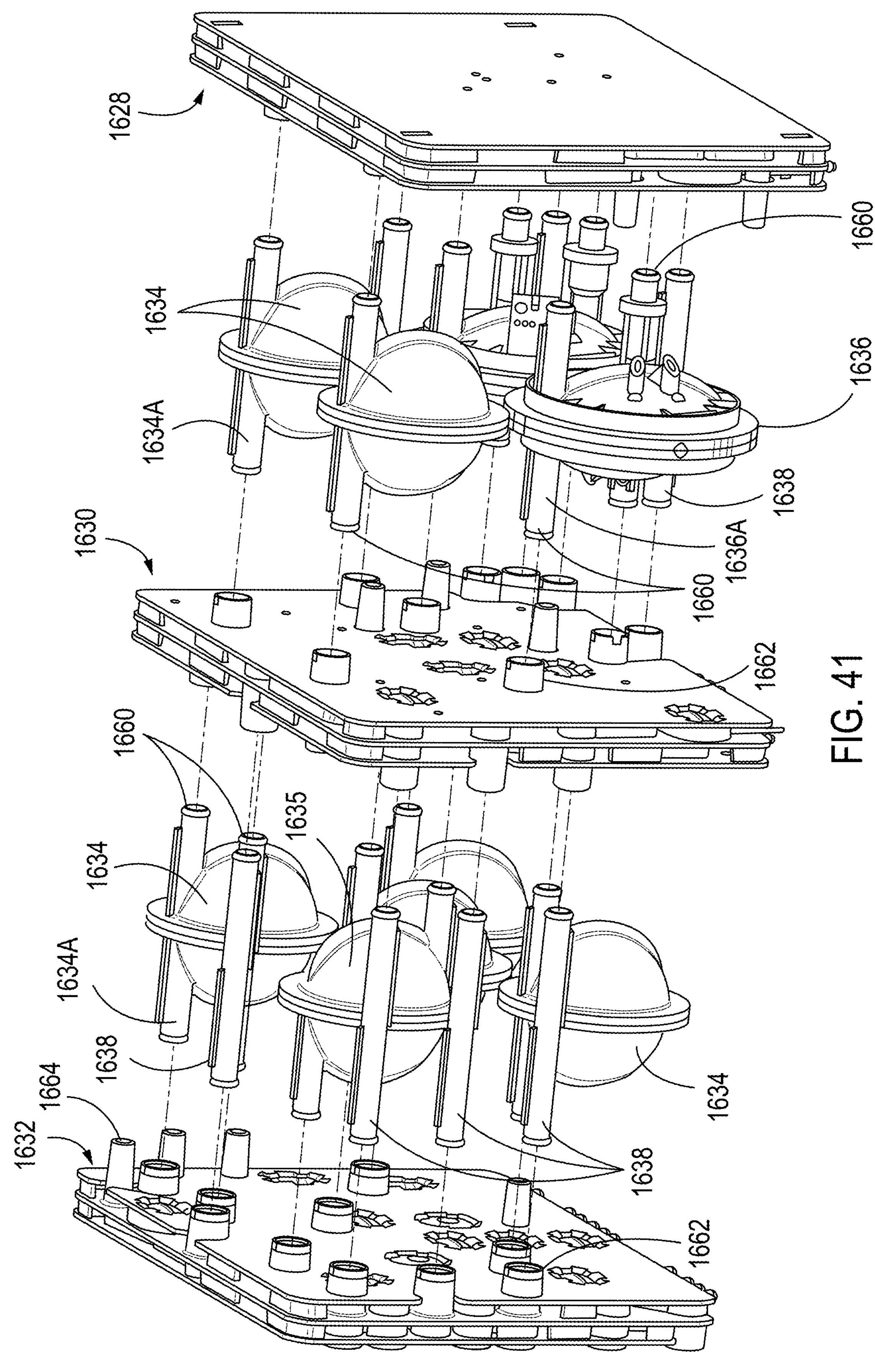
FIG. 41 is an exploded view of the dialysis cassette assembly shown in FIG. 40 without the sensor cassette or the frame assembly.

FIG. 10A presents a cross-sectional view of a pod pump 1864 that is one implementation of the pod pumps 161, 162 in FIG. 5, 159 in FIGS. 6 and 280, 282 in FIG. 7. The pod pumps are mounted between cassettes as shown in FIGS. 40-41, where the port ends 41 are plugged into ports on the face of the cassettes. The pod pump 1634 in one embodiment includes similar two chambers 32 that are bonded or fused together at flange 37. The two chambers may be welded ultrasonically, joined with adhesive or laser welded. A flexible diaphragm 109 is captured between the two chambers 32, where the thickened rim 88 is mechanically captured in a groove in the rim 37. The diaphragm 109 separates an actuation chamber 39 from a pumping chamber. The pumping chamber 38 is fluidly connected to a fluid pathway in a cassette. The actuation chamber 39 is fluid connected to an actuation channel in the cassette. In some embodiments of the chamber 32 may include a surface groove fluid connected to the port line 41. Amongst other benefits, the groove can prevent the diaphragm 109 from blocking the inlet or outlet (or both) flow path for fluid or air (or both).

Figure 10B:
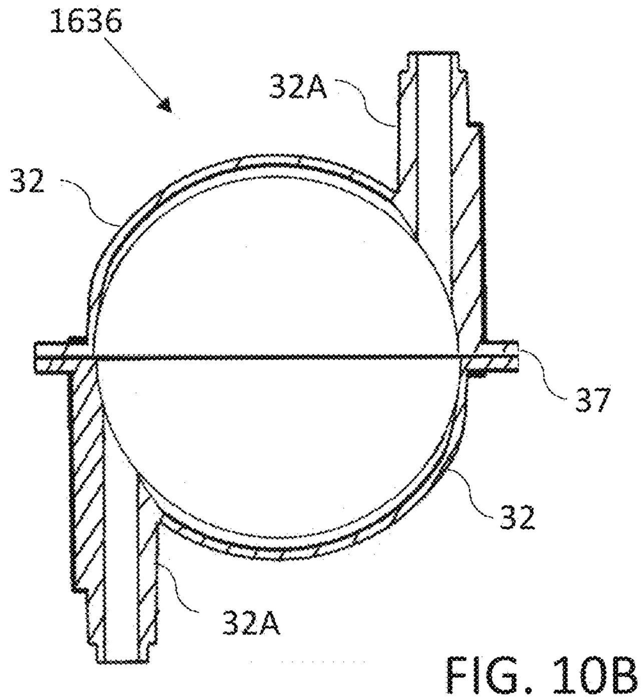
FIG. 10B is a cross-sectional view of a mixing chamber.

FIG. 10B presents a fluid mixing chamber or mixing pod 1636. The mixing pod 1636 in one embodiment includes similar two chambers 32 that are bonded or fused together at flange 37. The two chambers may be welded ultrasonically, joined with adhesive or laser welded. In one example, the chambers are bonded so the port lines 32A are not aligned to increase turbulence and mixing in the mixing pod.

Pneumatic Pumping System

Figure 11:
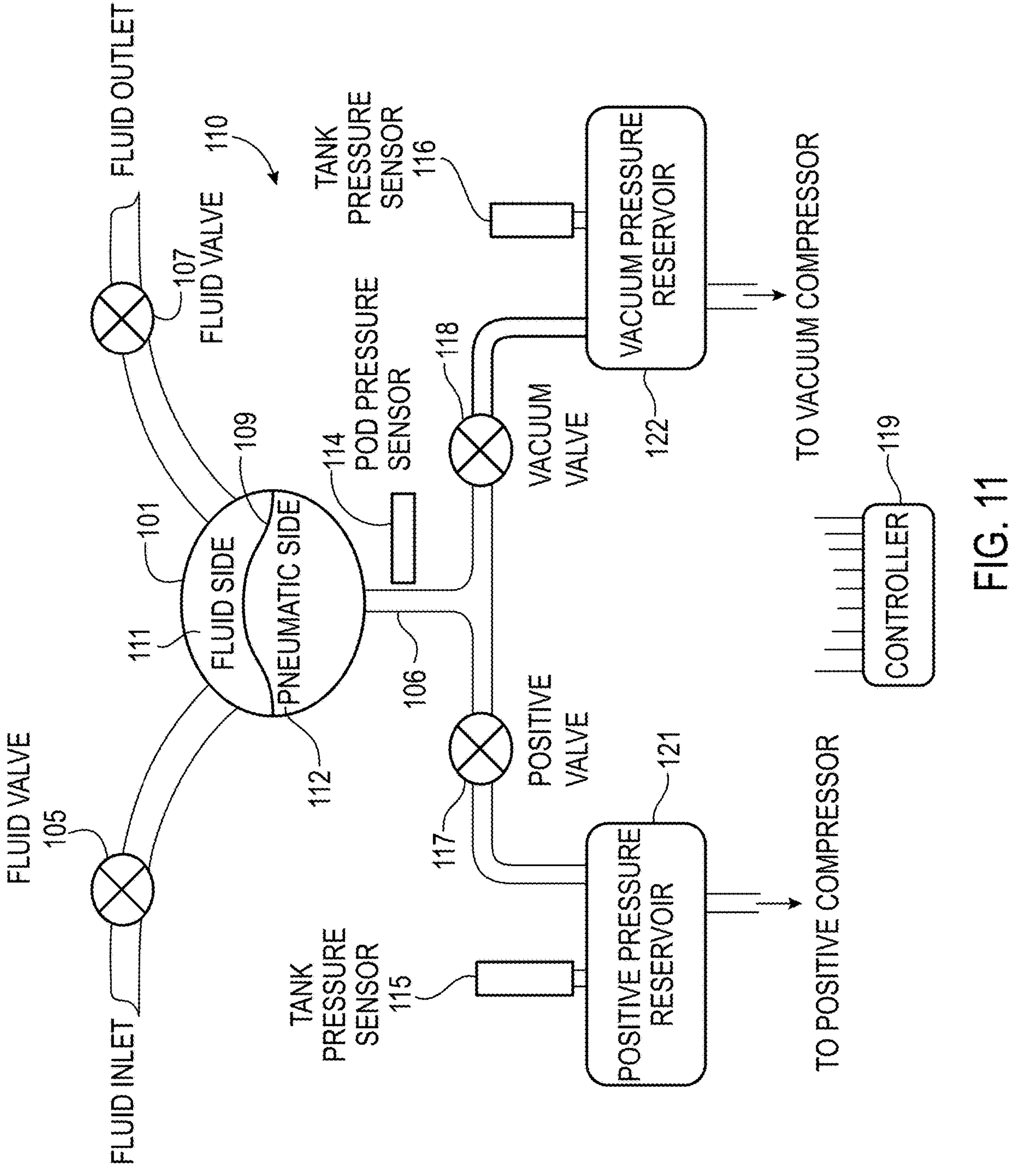
FIG. 11 is a schematic view of a pneumatic control system for a pod pump.

FIG. 11 is a schematic view showing an embodiment of a pressure actuation system 110 for a pod pump, such as that shown in FIG. 10. The fluid inlet line and fluid outlet line are controllably isolated from the pumping chamber 111 by fluid valve 105 and fluid valve 107. The inlet line and outlet fluid line may each connect to the pumping chamber via independent ports as shown in FIG. 11. In another example, the inlet fluid line is joined to the outlet fluid line between the fluid valves 105 and 107. The joined fluid line is then fluidly connected to the pumping chamber 111 via a single port. The pumping chamber 111 is separated from the control chamber 112 by a diaphragm 109.

In this example, air is used as a control fluid (e.g., such that the pump is pneumatically driven). As mentioned, other fluids (e.g., water) may also be used as control fluids in other embodiments.

In FIG. 11, pressure actuation system 110 alternately provides positive and negative pressurizations to the gas in the actuation chamber 112 of the pod pump 101. The pneumatic actuation system 110 includes an actuation-chamber pressure transducer 114, a positive-supply valve 117, a negative-supply valve 118, a positive-pressure gas reservoir 121, a negative-pressure gas reservoir 122, a positive-pressure-reservoir pressure transducer 115, a negative-pressure-reservoir pressure transducer 116, as well as an electronic controller 119.

The positive-pressure reservoir 121 provides to the actuation chamber 112 the positive pressurization of a control gas to urge the diaphragm 109 towards a position where the pumping chamber 111 is at its minimum volume (i.e., the position where the diaphragm is against the rigid pumping-chamber wall). The negative-pressure reservoir 122 provides to the actuation chamber 112 the negative pressurization of the control gas to urge the diaphragm 109 in the opposite direction, towards a position where the pumping chamber 111 is at its maximum volume (i.e., the position where the diaphragm is against the rigid actuation-chamber wall).

Figure 22:
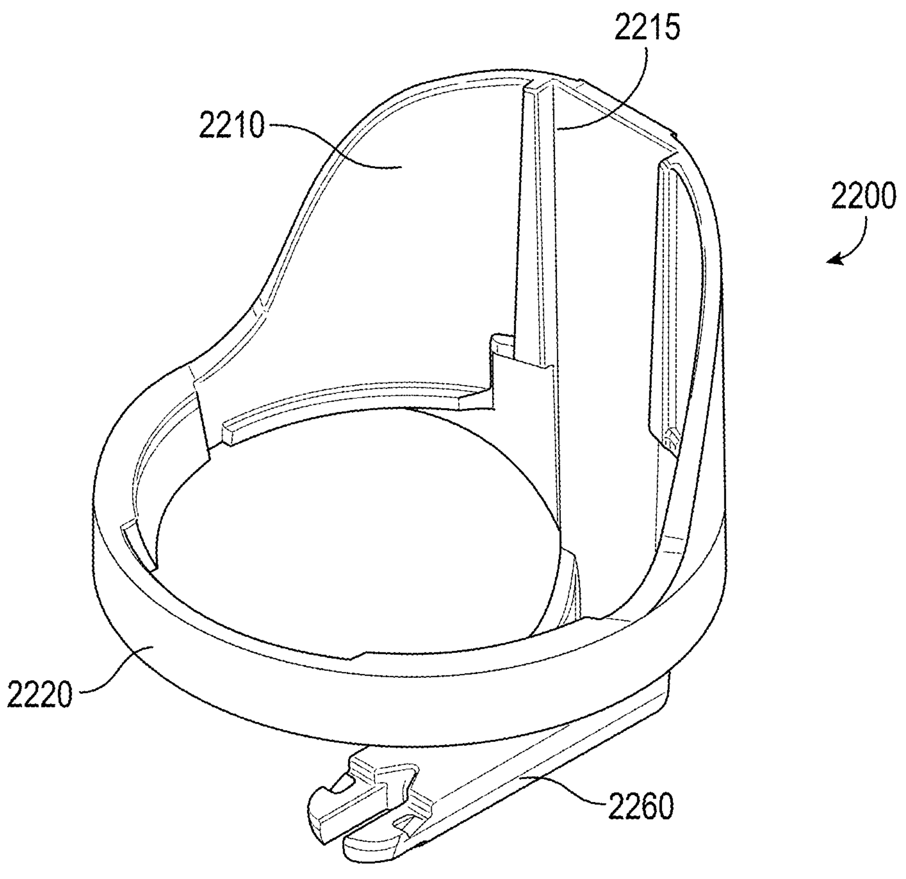
FIGS. 22-23 are perspective views of the vial support of the blood pump cassette in an illustrative embodiment including a medication vial.

A valving mechanism is used in this example to control fluid communication between each of these reservoirs 121, 122 and the actuation chamber 112. In FIG. 22 11A, a separate valve between the positive-pressure reservoir 121 and the actuation chamber 112, and a negative-supply valve 118 controls fluid communication between the negative-pressure reservoir 122 and the actuation chamber 112. These two valves are controlled by an electronic controller 119. (Alternatively, a single three-way valve may be used in lieu of the two separate valves 117, 118.) In some cases, the positive-supply valve 117 and the negative-supply valve 118 are binary on-off valves The controller 119 also receives pressure information from the three pressure transducers shown in FIG. 11: an actuation-chamber pressure transducer 114, a positive-pressure-reservoir pressure transducer 115, and a negative-pressure-reservoir pressure transducer 116. As their names suggest, these transducers respectively measure the pressure in the actuation chamber 112, the positive-pressure reservoir 121, and the negative-pressure reservoir 122. The controller 119 monitors the pressure in the two reservoirs 121, 122 to ensure they are properly pressurized (either positively or negatively). A compressor-type pump or pumps may be used to attain the desired pressures in these reservoirs 121, 122.

In one embodiment, the pressure provided by the positive-pressure reservoir 121 is strong enough, under normal conditions, to urge the diaphragm 109 all the way against the rigid pumping-chamber wall. Similarly, the negative pressure (i.e., the vacuum) provided by the negative-pressure reservoir 122 is preferably strong enough, under normal conditions, to urge the diaphragm all the way against the rigid actuation-chamber wall. In some embodiments, however, these positive and negative pressures provided by the reservoirs 121, 122 are within safe enough limits that even with either the positive-supply valve 117 or the negative-supply valve 118 open all the way the positive or negative pressure applied against the diaphragm 109 is not so strong as to harm the patient.

In one embodiment, the controller 119 monitors the pressure information from the actuation-chamber-pressure transducer 114 and, based on this information, controls the valving mechanism (valves 117, 118) to urge the diaphragm 109 all the way to its minimum-pumping-chamber-volume position and then after this position is reached to pull the diaphragm 109 all the way back to its maximum-pumping-chamber-volume position.

The pressure actuation system (including the actuation-chamber pressure transducer 114, the positive-pressure-reservoir pressure transducer 115, the negative-pressure-reservoir pressure transducer 116, the variable positive-supply valve 117, the variable negative-supply valve 118, the controller 119, the positive-pressure gas reservoir 121, and the negative-pressure gas reservoir 122) is located entirely or mostly outside the insulated volume (item 61 of FIG. 6). The components that come into contact with blood or dialysate (namely, pod pump 101, the inlet valve 105 and the outlet valve 107) may be located, in some cases, in the insulated volume so that they can be more easily disinfected.

It will be appreciated that other types of actuation systems may be used to move the diaphragm back and forth instead of the two-reservoir pneumatic actuation system shown in FIG. 11.

As noted above, the positive-supply valve 117 and the negative-supply valve 118 in the pneumatic actuation system 110 of FIG. 11 are preferably binary on-off valves. The binary valves 117, 118 can be controlled to achieve a desired pressure in the actuation chamber 112 instead of applying the full reservoir pressure to the diaphragm. Thus, the same reservoir or set of reservoirs may be used for different pod pumps, even though the pressures for operating the pod pumps may differ from pod pump to pod pump. Of course, the reservoir pressure needs to be greater than the desired pressures to be applied to various pod pump's diaphragms, but one pod pump may be operated at, say, half of the reservoir pressure, and another pod pump may be actuated with the same reservoir but at, say, a quarter of the reservoir pressure. Thus, even though different pod pumps in the dialysis system are designed to operate at different pressures, these pod pumps may all share the same reservoir or set of reservoirs but still be actuated at different pressures, through the use of variable valves. The pressures used in a pod pump may be changed to address conditions that may arise or change during a dialysis procedure. For example, if flow through the system's tubing becomes constricted because the tubes get twisted, one or both of the positive or negative pressures used in the pod pump may be increased in order to over compensate for the increased restriction.

Hemodialysis Chassis and System Components

Figure 12A:
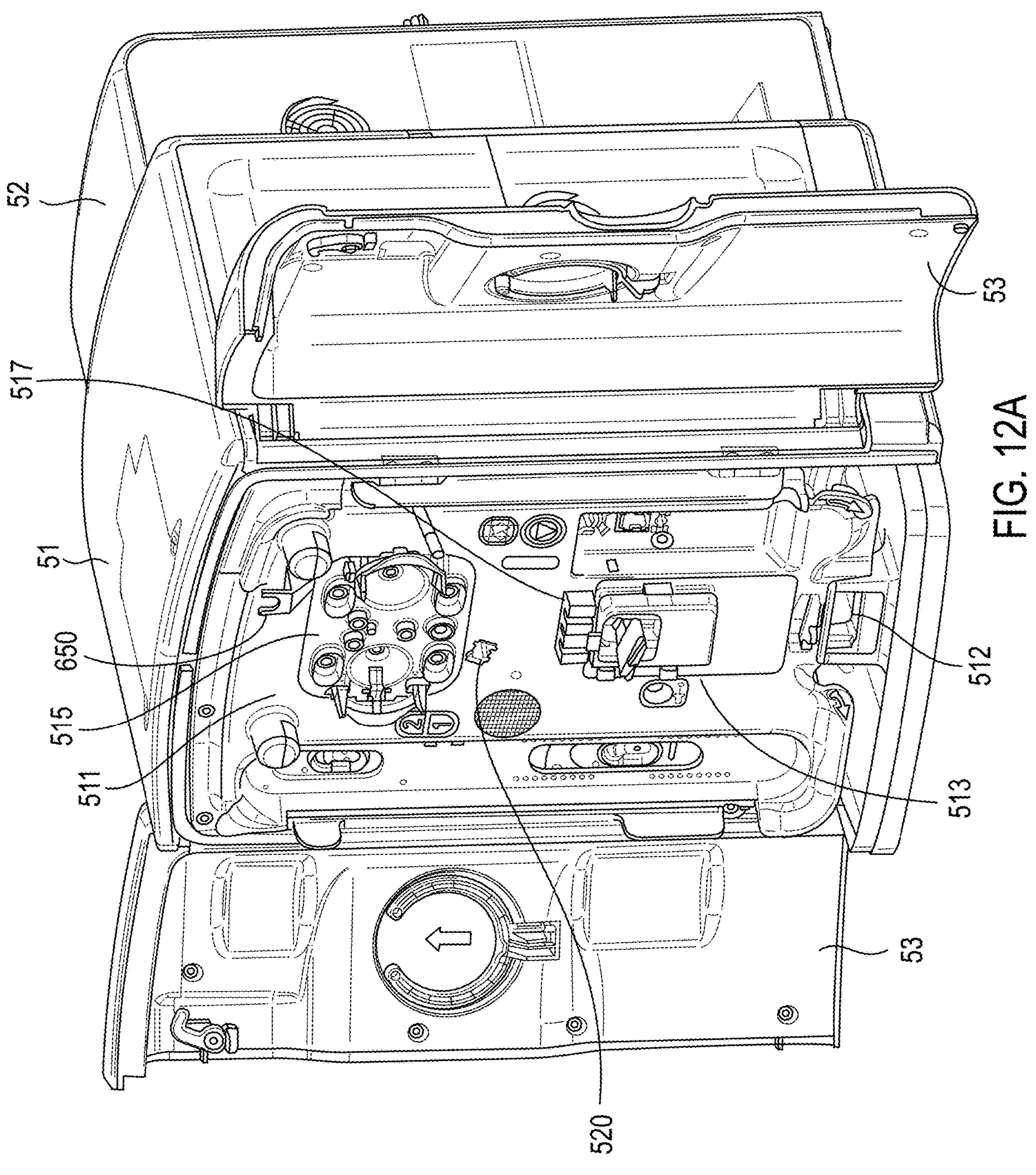
FIG. 12A is a right front perspective view of a hemodialysis system without disposable elements in an illustrative embodiment.

FIG. 12A shows a perspective view of a hemodialysis system 5 that incorporates various aspects of the invention. In accordance with one aspect of the invention, the system 5 includes a hemodialysis unit 51 and a power unit module 52 that are shown joined together. In this embodiment, the hemodialysis unit 51 has a housing that contains suitable components for performing hemodialysis, such as a dialyzer, one or more pumps to circulate blood through the dialyzer, a source of dialysate, and one or more pumps to circulate the dialysate through the dialyzer. For example, the hemodialysis unit 51 may include the mixing circuit 25, blood flow circuit 141, the balancing circuit 143 and the directing circuit 142 as described above. The hemodialysis unit 51 may also include all blood circuit connections and dialysate fluidic connections needed for operation of the system Patient access and other connections on a front panel 511 may be revealed by opening side-by-side vertical doors 53 via a handle at a front side of the hemodialysis unit 51 housing. The front panel includes a blood pump receptacle 515 that receives the blood pump cassette of the blood pump assembly and provides pneumatic power to the pumps and valves of the blood pump cassette. The control ports in the blood pump receptacle 515 provide controlled levels of air pressure and/or vacuum to control the open/closed state of valves and to power the blood pump cassette. A dialyzer hanger 650 that supports the dialyzer by one port, which facilitates making the other fluid connections to the dialyzer. An electrical receptacle 520 receives an ADS electrical plug located on the blood pump assembly. The front panel 511 further includes two air-in-line sensors 517 and an occluder assembly 513 that both receive blood lines from the blood pump assembly as will be explained below. A chemical receptacle 512 is configured to receive the bicarbonate, water and acid connections of the chem set plug.

Figure 12B:
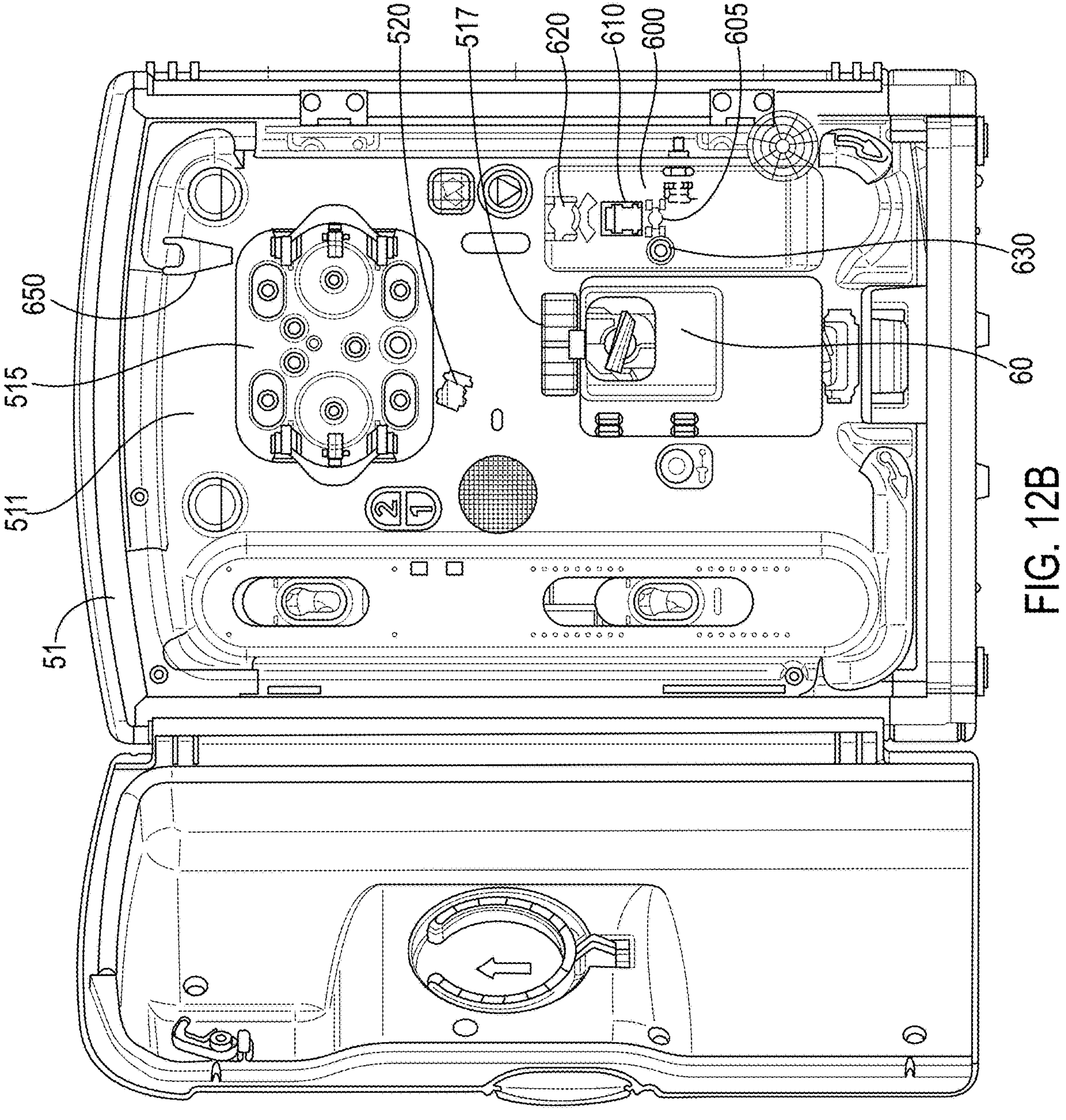
FIG. 12B is a front view of the of a hemodialysis system without disposable elements in an illustrative embodiment.

Referring now to FIG. 12B, the front panel 511 also includes a drain recess 600 that receives the drain cassette. The drain recess 600 comprises a pneumatic port 620, an electrical receptacle 610 and a liquid port 630. The drain cassette described below includes ports for optionally connecting the arterial and venous blood lines 203, 204 of the blood flow circuit 141 with the directing circuit 142 (as explained above with reference to FIGS. 2 and 3.) This connection is normally made at the end of treatment to allow the system to clean and disinfect the blood flow circuit 141.

User Interface

Figure 12C:
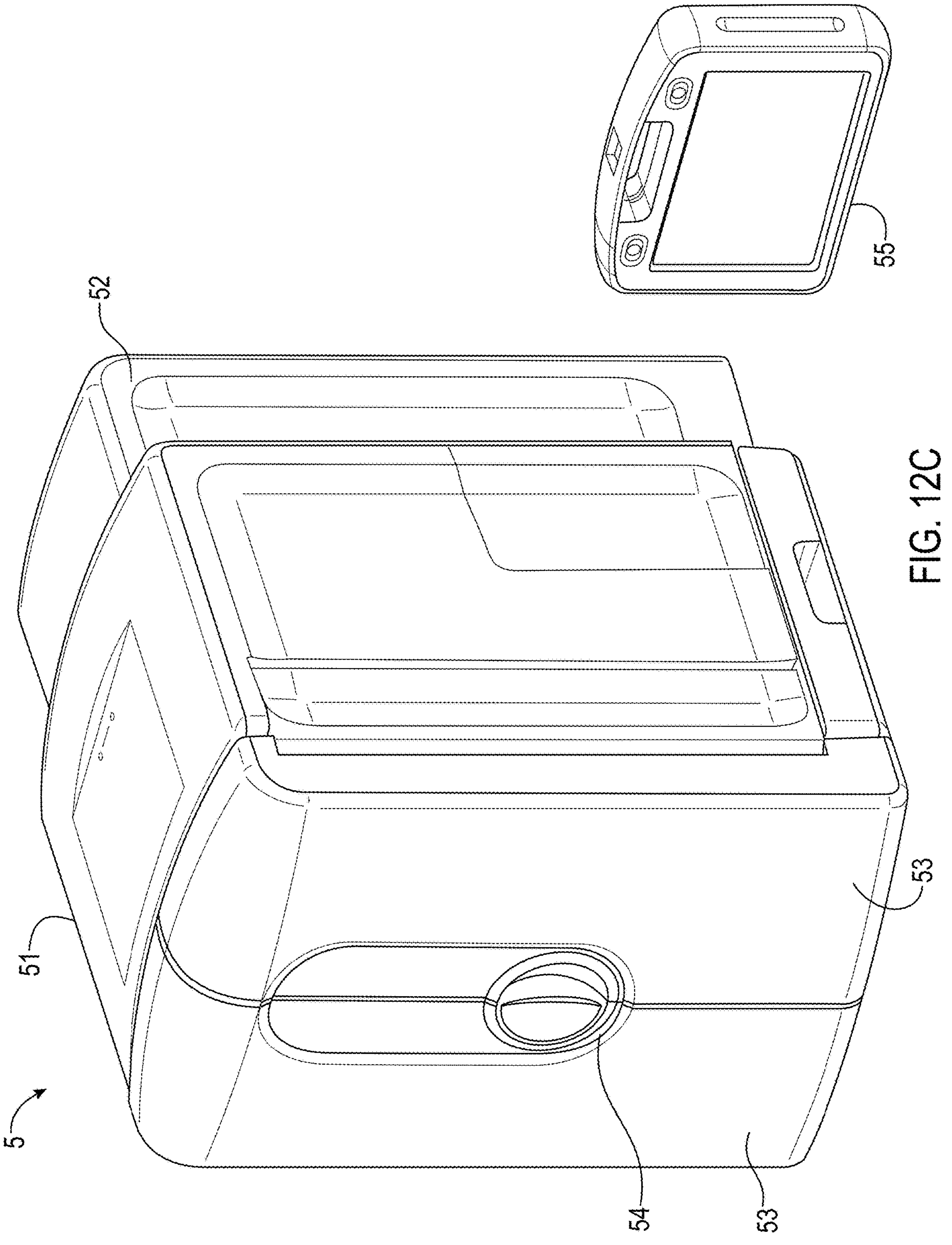
FIG. 12C is a perspective view of a hemodialysis system with a user interface.
Figure 12D:
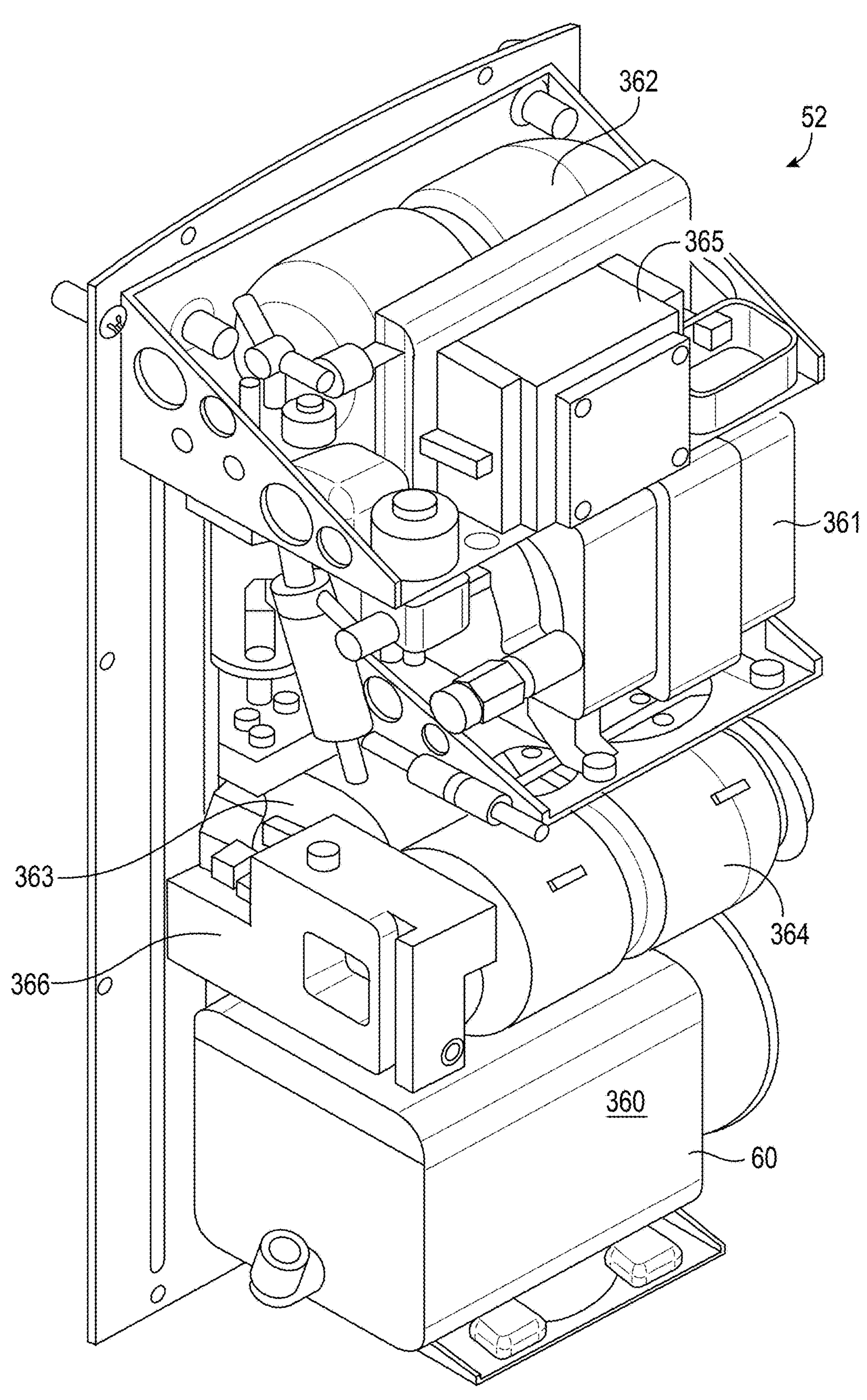
FIG. 12D is a perspective view of the power unit module without the cover.

Referring now to FIG. 12C, the hemodialysis unit 51 includes a control interface ( ). The control interface is wirelessly connected to hemodialysis unit 51 and configured to allow a user to control operation of the dialysis unit 51. The control interface may include a display screen with a touch sensitive overlay to allow touch control and interaction with a graphical user interface presented on the screen. The control interface may also include other features, such as push buttons, a speaker, a microphone for receiving voice commands, a digital camera, and so on. The top of the hemodialysis unit 51 may include a retractable "kick-stand" (not shown) that supports the control interface 55 when positioned on top of the hemodialysis unit 51 housing. In other embodiments, control interface 55 may comprise a tablet-style computer or hand-held electronic communications device, either of which may communicate wirelessly with a controller housed within dialysis unit 51. In one embodiment, the control interface is a smart phone that communicates wirelessly with the hemodialysis unit 51 and the hemodialysis unit is controlled by an app on the phone. Examples of wireless communications means may include Bluetooth® technology or wireless local area network technology such as Wi-Fi®.

Power Unit Module

The power unit 52 housing may contain suitable components for providing operating power to the dialysis unit 51, e.g., pneumatic pressure/vacuum to power the pumps, valves and other components of the dialysis unit 51. "Pneumatic," as used herein, means using air or other gas to move a flexible diaphragm or other member. (It should be noted that air is used by way of example only, and in other embodiments, other control gases, such as nitrogen ($N_2$), $CO_2$, etc., may be used). As discussed above, the pumps and valves of the hemodialysis unit 51 may operate on pneumatic power, and thus the power unit 52 may provide one or more pneumatic sources for use by the dialysis unit 51. In this way, the hemodialysis unit 51 need not necessarily be arranged to generate and/or store the necessary pneumatic power needed, but instead may rely on the power unit module 52. The power unit 52 may include one or more pneumatic pumps to generate desired air pressure and/or vacuum, one or more accumulators or other devices to store pneumatic power, valves, conduits and/or other devices to control flow of pneumatic power in the power unit 52, as well as a controller having suitable components, such as a programmed general purpose data processor, memory, sensors (e.g., to detect pressure, temperature, etc.), relays, actuators, and so on.

In one embodiment, the pneumatic power (e.g., air under suitable pressure/vacuum) may be supplied by the power unit 52 to the hemodialysis unit 51 from one or more supply tanks or other pressure sources. The supply tanks are fluidly connected to the hemodialysis unit 51 via a plurality of tubes, where each tube supplies a given pressure. For instance, if two tanks are used in the power unit 52, one supply tank may be a positive pressure reservoir, and in one embodiment, has a set point of 750 mmHg (gauge pressure) (1 mmHg is about 133.3 pascals). The other supply tank can be a vacuum or negative pressure reservoir, and in one embodiment, has a set point of −450 mmHg (gauge pressure). This pressure difference may be used, for instance, between the supply tanks and the required pod pump pressure to allow for accurate control of the variable valves to the pod pumps. The supply pressure limits can be set based on maximum pressures that can be set for the patient blood flow pump plus some margin to provide enough of a pressure difference for control of the variable valves. Thus, in some cases, the two tanks may be used to supply pressures and control fluids for all of the hemodialysis unit 51 functions.

In one embodiment, the power unit 52 may include two independent compressors to service the supply tanks. A Pressure in the tanks can be controlled using any suitable technique, for instance, with a simple "bang-bang" controller (a controller that exists in two states, i.e., in an on or open state, and an off or closed state), or with more sophisticated control mechanisms, depending on the embodiment. As an example of a bang-bang controller, for the positive tank, if the actual pressure is less than a set point, the compressor servicing the positive tank is turned on. If the actual pressure is greater than a set point, the compressor servicing the positive tank is turned off. The same logic may be applied to the vacuum tank and control of the vacuum compressor with the exception that the sign of the set point term is reversed. If the pressure tanks are not being regulated, the compressor is turned off and the valves are closed.

Tighter control of the pressure tanks can be achieved by reducing the size of the hysteresis band, however this may result in higher cycling frequencies of the compressor. If very tight control of these reservoirs is required, the bang-bang controller could be replaced with a proportional-integral-derivative ("PID") controller and using pulse width modulation ("PWM") signals on the compressors. Other methods of control are also possible.

In an embodiment, power unit 52 comprises a housing that may contain components as shown in FIG. 12C. In this example, a pump and pneumatic storage assembly is arranged to fit within power unit 52, and comprises a positive pressure pump 360, a negative pressure or vacuum pump 361, a high-positive pressure reservoir 362, a lower-positive pressure reservoir 363, a negative pressure reservoir 364, and a dehumidification or ' chiller' unit 365. The high-positive pressure reservoir 362, for example, may store air at pressures of about 1000-1100 or more mmHg, and the lower-positive pressure reservoir 363, for example, may store air at pressures of about 700-850 mmHg. The pressurized air generated by positive pressure pump 360 may be used to fill reservoir 363 by interposing a pressure regulator 366 between the outlet of pump 360 and the inlet of reservoir 363.

Chiller 365, or another suitable dehumidifier, may be interposed between the outlet of positive pressure pump 360 and the inlet of the one or more positive pressure reservoirs 362 and/or 363. De-humidification of the pressurized air may prevent water condensation inside pneumatic lines or manifold passages and valves driven by the positive pressure reservoirs 362 and/or 363.

Other pressure sources may be used in other embodiments, and in some cases, more than one positive pressure source and/or more than one negative pressure source may be used. For instance, more than one positive pressure source may be used that provides different positive pressures (e.g., 1000 mmHg and 700 mmHg), which may be used to minimize leakage. For example, high positive pressure can be used to control valves, whereas lower positive pressures can be used to control pumps. This limits the amount of pressure that can potentially be sent to the dialyzer or to the patient, and helps to keep actuation of the pumps from overcoming the pressures applied to adjacent valves. Lower pressures may be used in pumps to minimize damage to the blood or applied pressure to the fluid lines connected to the patient. A non-limiting example of a negative pressure is −400 mmHg. In some cases, the negative pressure source may be a vacuum pump, while the positive pressure pump may be an air compressor.

Front Panel Components

Figure 13:
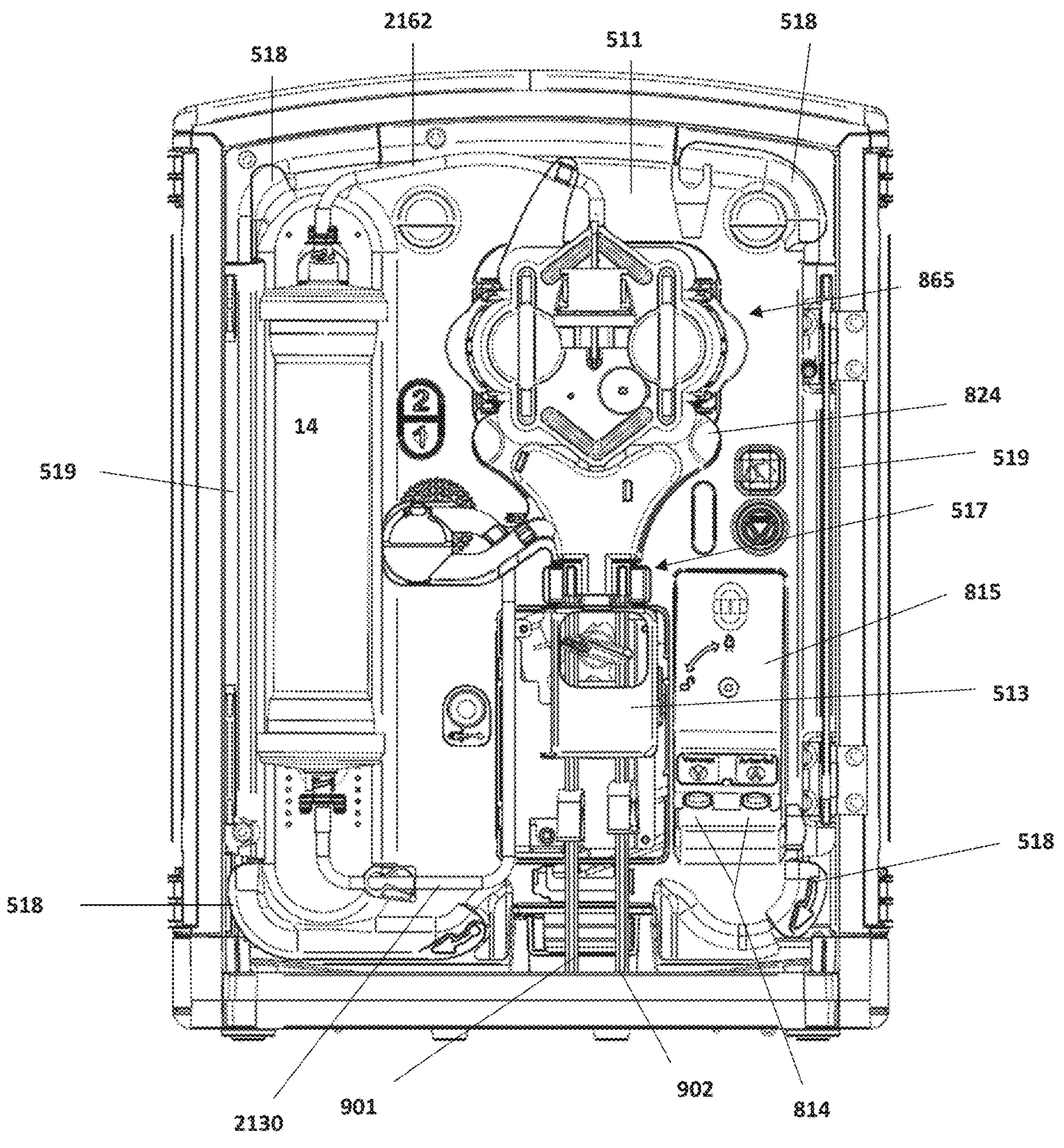
FIG. 13 is a front view of a hemodialysis system with disposable elements in an illustrative embodiment

In accordance with another aspect of the invention, opening of the doors to the dialysis unit housing may reveal the disposables and the user-made connections for blood circuit connections and dialysate fluidic connections needed for operation of the system 5. For example, as shown in FIG. 13, with the doors 53 in an open position, the disposable blood pump assembly 865, dialyzer 14 and drain cassette 815 are visible and mounted on the front panel 511 of the hemodialysis unit 51. The blood pump assembly 865 comprising the blood pump cassette 824 and air trap The front panel 511 receives and carries several items or connection points that are accessed by a user including the dialyzer 14, which must be periodically replaced. The dialyzer 14 is connected to the blood circuit 141 as implemented by the blood pump assembly 865 via lines 2130 at the bottom and 2162 at the top of the dialyzer. The dialyzer 14 is also connected via two ports extending through the front panel 511 to the balancing circuit (not shown) that is implemented as part of the dialysate cassette assembly and located behind the front panel 511. A chemical receptacle 512 that receives the chem-set plug for acid and bicarbonate is located at a lower end of the front panel 511

The air-in-line sensor 517 and occluder assembly 513 receive the patient blood lines 901, 902 blood pump assembly 865. The blood pump assembly 865 implements the blood flow circuit minus the dialyzer of the blood flow circuit 141 in FIG. 3. The patient blood lines are separately referred to as the venous blood line 901 and the arterial blood line 902. The air-in-line sensor 517 detects the presence of air or gas bubbles in either the arterial line 902 or the venous line 901.

The occluder assembly 513 controls the open/closed state of the tubes based on system operation. The occluder assembly 513 block flow through the arterial line 902 and venous line 901 of the blood flow circuit unless the controller determines hemodialysis system is in a safe state to flow liquid through the blood lines. If the controller detects a problem, such as a leak, pump failure, overpressure situation, etc, the occluder assembly 513 automatically closes the blood lines to prevent all flow through the blood lines. If the blood lines are connected to the patient, then closing the occluder assembly prevents blood flow to or from the patient.

In some cases, the occluding member may be automatically or externally controlled. For example, as is discussed below, the occluding member may be moved from a closed position to an open position with an actuator as commanded by a controller in the hemodialysis unit. The occluding member is biased to remain in a closed position. The biasing is such that it can be manually overridden (e.g., allowing movement of the occluding member to an open position), for instance by use of grip member 28, as previously discussed. In some cases, the occluder may be constructed and arranged to fail (e.g., due to loss of power) in a first or "closed" position, i.e., a position that at least partially prevents fluid flow.

The front panel 511 has blood pump receptacle that receives the blood pump cassette 824 of the blood pump assembly 865 and provides positive and negative pressure to operate the pumps and valves of the blood pump cassette 824. In FIG. 13, the drain cassette 815 is installed in the drain recess on the front panel 511. The drain cassette 815 includes ports 814 to receive the connectors at the end of the venous blood line 901 and the arterial blood line 902.

Blood Line Wrap on Front Panel

Referring now to FIG. 13, in accordance with another aspect of the invention, the front panel 511 includes a blood line wrap feature around the periphery of the front panel 511. In this illustrative embodiment, the front panel 511 includes tubing storage guides 518 along the top edge and at lower corners of the front panel 511. This allows a user to wrap the patient blood lines 901, 902 around the periphery of the front panel 511 by placing the lines 901, 902 in a channel defined by the tubing storage guides 518. Vertical fences 519 may also be provided along the left and right sides of the front panel 511 to help keep the blood lines 901, 902 in a desired position and away from the hinge plates 533 and other possible pinch points. The lines 901, 902 may be wrapped in a clockwise direction, starting from a point near the bottom of the dialyzer 14, and ending at a point near the lower right corner of the front panel 511. The patient blood lines 901, 902 may then be connected at the blood line connection points 514, e.g., to allow disinfecting fluid to be circulated through the patient blood lines 901, 902. The lines 901, 902 and the tubing storage guides are sized to that patient blood lines are not loose and remain within the vertical fences 519 and do not have loose sections of tubing that could interfere with closing the doors. As a result, the patient blood lines 901, 902 are neatly retained on the front panel 511, allowing easy access to other components on the front panel 511 and allowing the user to close the doors 53 without pinching the patient blood lines 901, 902 between the doors 53 and the dialyzer unit housing 51. Successful disinfection of the blood tubing and the blood circuit is facilitated by the blood lines not being pinched so that disinfection fluid can flow through the blood circuit and by allowing the doors 53 to close to insulate fluid paths on the front panel 511.

Alternatively, the patient blood lines 901, 902 may be first connected at the blood line connection points 514, and then wrapped around the periphery of the front panel 511 defined by the tubing storage guides 518 and vertical fences 519. The tubing storage guides 518 hold the blood lines 901, 902 in place and allow the doors 53 to close, while the blood lines are connected to the drain cassette 815. In this position, the blood lines can heat sterilized with the door closed and hot water being pumped through the blood lines.

Dialyzer Hanger

Figure 14A:
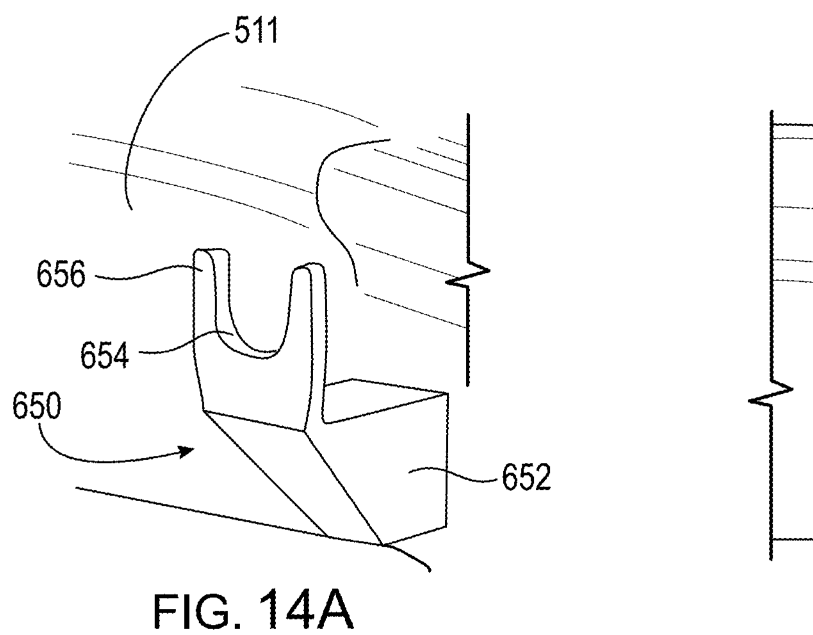
FIG. 14A is a right front view of the dialyzer hanger.
Figure 14B:
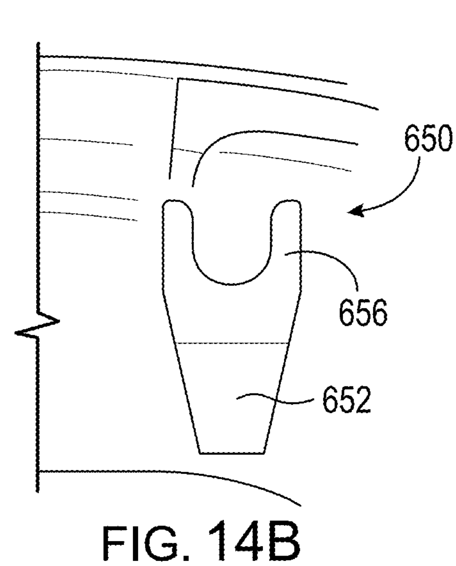
FIG. 14B is a front view of the dialyzer hanger.

Referring to FIG. 14A, 14B, the front panel 511 further comprises a dialyzer hanger 650 that is located near the top of the front panel 511. The dialyzer hanger 650 is configured to receive the one of the dialysis ports (not shown) of the dialyzer 14. The dialyzer hanger 12 holds and secures the dialyzer 14 on the front panel 511 while connections are made to the blood ports on the dialyzer 14 by blood lines 2130, 2162. The hanger 620 includes a hanger brace 652 attached to the front panel 511. The hanger further includes a hanger fork 656 where the diameter of the hanger notch 654 accommodates the neck of the dialyzer blood port. The hanger brace 652 is sized so that the hanger fork 656 is spaced back from the front panel and above the brace. The dialyzer hanger fork 656 is configured so that the dialyzer port can seat in the hangar fork 656 without touching the hanger braze 652 nor the font panel 511.

Air-in-Line (AIL) Sensors

Figure 15:
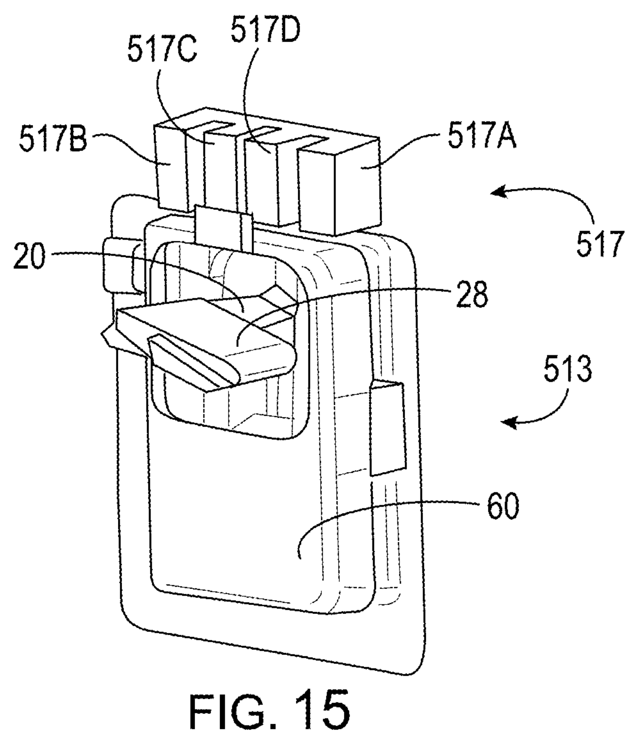
FIG. 15 is a right front view of the occluder assembly and air-in-line sensors.

Referring now to FIG. 15, the front panel 511 includes two Air-In-Line (AIL) sensors 517 as that receive the patient blood lines 901, 902. Air-in-line sensors 517 are also referred to as AIL sensors. As shown in FIG. 2, the blood line 203 passes by AIL, sensor 33*a* and blood line 204 pass by AIL sensor 33*b* in the blood circuit 141. Referring again to FIG. 15, the AIL sensors 517 are mounted on the front panel just above the occluder assembly 513. The AIL sensor 517 includes an AIL module 517B for that receives the venous line in AIL slot 517D and a module 517A that receives the arterial line in AIL slot 517C. The slots 517C, 517D are oriented vertically and are aligned with the receiving pathways of the occluder assembly 513. The sensitivity of the AIL sensor modules 517B, 517A is improved by having good contact between the blood lines and the AIL sensors by assuring no air gaps between the slots 517C, 517D and the outer walls of the blood tubing. Good contact may be achieved by sizing the slots 517 C, 517D smaller than the OD of the patient blood lines 901, 902. Good contact may also be improved by pushing the blood lines into the AIL slots 517C, 517D. As will be discussed in more detail below, the blood lines are located into the AIL sensor 517 and the occluder assembly 513 as a single process.

The occlusion assembly 513 receives the blood line tubes 902 in pathways 18, 19 and is configured to occlude the tubes 901, 902 (FIG. 13) by rotating the occluding member 20 into pathways 18, 19. The rotated occluding member 20 compresses the patient blood lines against the outer walls of the pathways 18, 19. The compressing action reduces the size of an inner fluid pathway of each blood line to restrict the flow of fluid there through. In one example, the occluding member 20 compresses the tubes sufficiently to complete stop flow through the patient blood lines 901, 902.

BTS Receiving Latch and Control Ports

Figure 16:
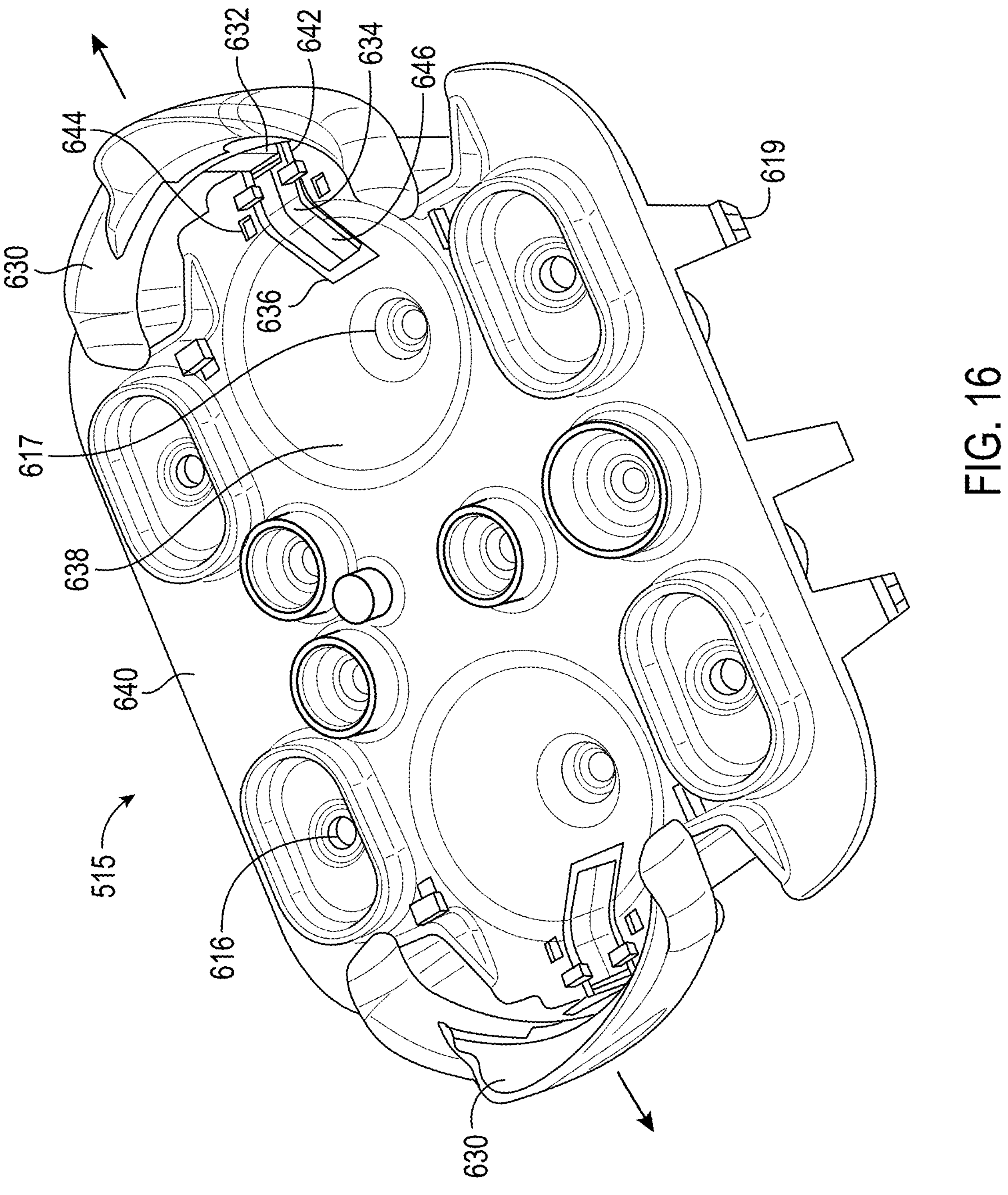
FIG. 16 shows a perspective view of a control port assembly with blood pump cassette latching and ejection assemblies in an illustrative embodiment.

In another aspect of the invention, FIG. 16 shows a perspective view of a control blood pump receptacle 515 onto which a blood pump cassette 824 may be mounted, and with which the fluidic control ports of the blood pump assembly 13 can connect. Shown, for example, are control ports 616 for receiving actuation ports of valves on a blood pump cassette 13, and control ports 617 for receiving the actuation ports of the blood pumps on the blood pump cassette. The hemodialysis unit provides positive, atmospheric or negative pressure to the control ports 616, 617 to control actuate the valves and pumps of the blood pump cassette 13. In order to secure a blood pump assembly 13 onto control port assembly 515, a latch member or other engagement device may be provided at one or more sides of, or within, control port assembly 615, or at a portion of front panel assembly 511 adjacent to, or within, the location of the control port assembly 515. (In the example shown, control port assembly 515 may be reversibly mounted onto front panel assembly 511 via retaining tabs 619). Alternately, or in addition, a disengagement or other ejection feature 630 for a blood circuit assembly may be provided to help with removal of a blood pump assembly or other parts of a blood circuit assembly from the front panel 511. For example, a pair of cassette latching and ejection assemblies 630 may be mounted on opposite sides of the control port assembly 515

Continuing to refer to FIG. 16 the blood circuit assembly engagement device includes a pair of blood pump cassette retainer and ejector elements 630. In this embodiment, cassette retainer element 630 includes a contacting member 632 that makes contact with an ejector (or separation assist) element 634. In a retracted state, ejector element 634 is positioned in a recessed area 636 of the blood pump pod recess 638 in the control port assembly 640. As retainer elements 630 are pivoted outward (direction of arrows in FIG. 15), contacting member 632 presses against a proximal end 642 of the ejector element 634, whereupon ejector element 634 rotates about pivot axis 644, causing a distal end 646 of ejector element 634 to lift out of recess 636 to engage the rigid back wall of the actuation chamber of a mounted blood pump cassette, which is positioned within the blood pump pod recess 638.

Blood Pump Assembly

Figure 17:
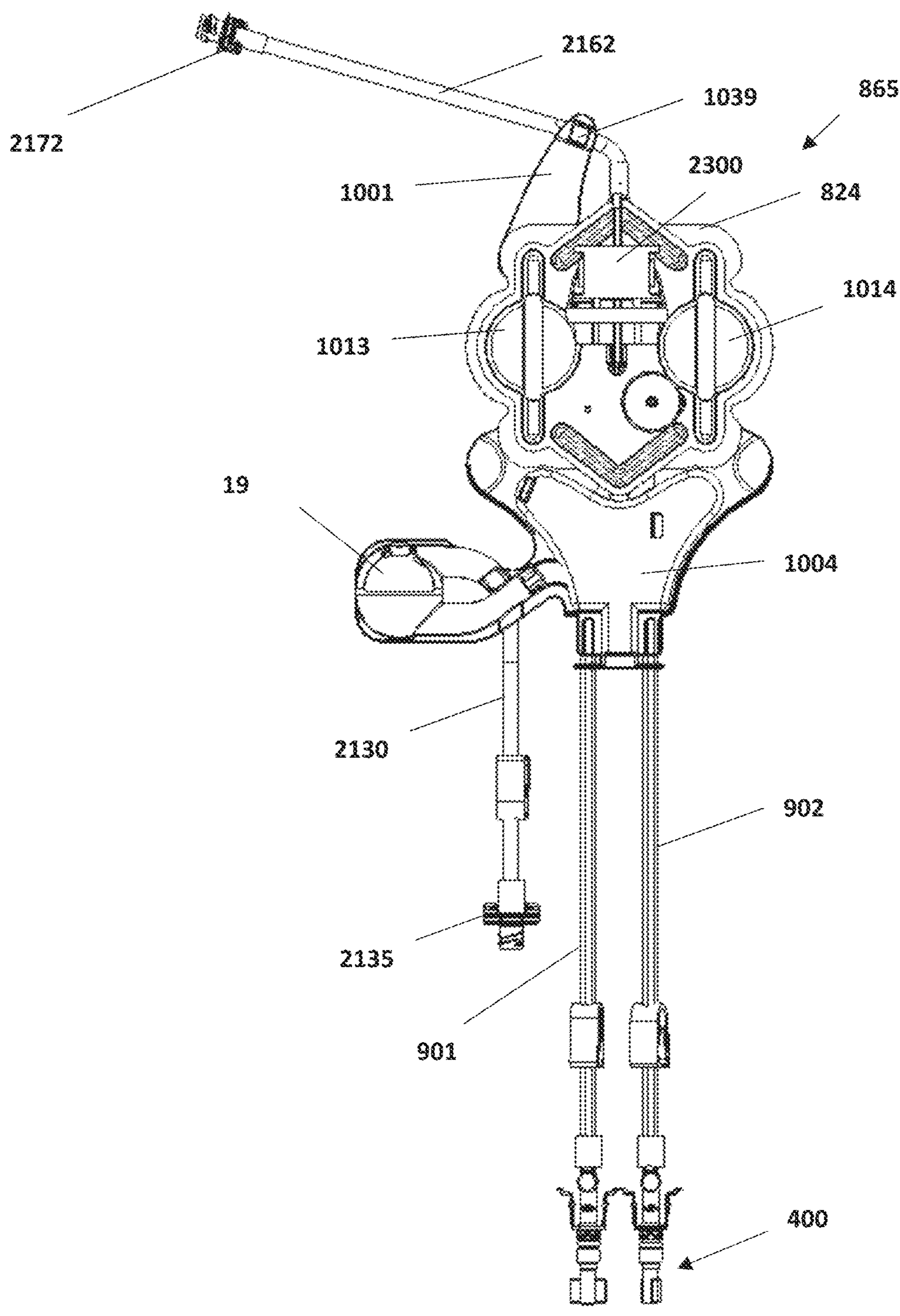
FIG. 17 is a front view of the blood pump assembly in an illustrative embodiment.

Referring now to FIG. 17, the blood pump assembly 865 comprises the blood pump cassette 824, the air trap 19 and the various blood lines 901, 902, 2130 and 2162. The pump cassette 824 comprise a back plate 1001 that serves as a tube organizer. The tube organizer holds the inlet dialyzer line 2162 that connects to the top of the dialyzer. The tube organizer protects the dialyzer line 2162 from repeated and excessive bending near the connection to the top of the blood cassette 824. The tube organizer holds the air trap 19, holds and protects the dialyzer outlet line 2130 from the bottom of the dialyzer and holds and protects the venous line 901. The tube organizer protects the dialyzer outlet line 2130 and venous line 901 from excessive bending near the connections to the air trap 19. The tube organizer also holds the tubes in position to facilitate attaching the blood pump assembly 865 on the front panel 511 of hemodialysis unit 51. The blood pump assembly 865 further includes the blood connectors 400 at the ends of the venous tube 901 and the arterial tube 902.

In hemodialysis applications, in some cases, an anticoagulant (e.g., heparin, or any other anticoagulant known to those of ordinary skill in the art) may be mixed with the blood within blood flow cassette 824. For example, the anticoagulant may be contained within a vial (or other anticoagulant supply, such as a tube or a bag), and blood flow cassette 824 may be able to receive the anticoagulant vial with a vial receiver 2300 (which, in one embodiment, includes a needle or hollow spike) that can pierce the seal of the vial. The spike may be formed from plastic, stainless steel, or another suitable material, and may be a sterilizable material in some cases, e.g., the material may be able to withstand sufficiently high temperatures and/or chemical exposure so as to sterilize the material. As an example, the spike may be used to pierce the seal of the vial, such that anticoagulant can flow into blood flow cassette 824 to be mixed with the blood in the blood flow path. In other cases, the vial may be filled or partially filled with water or dialysate during cleaning, disinfecting or priming operations.

Anti-Coagulant Vial Receiver

Figure 18:
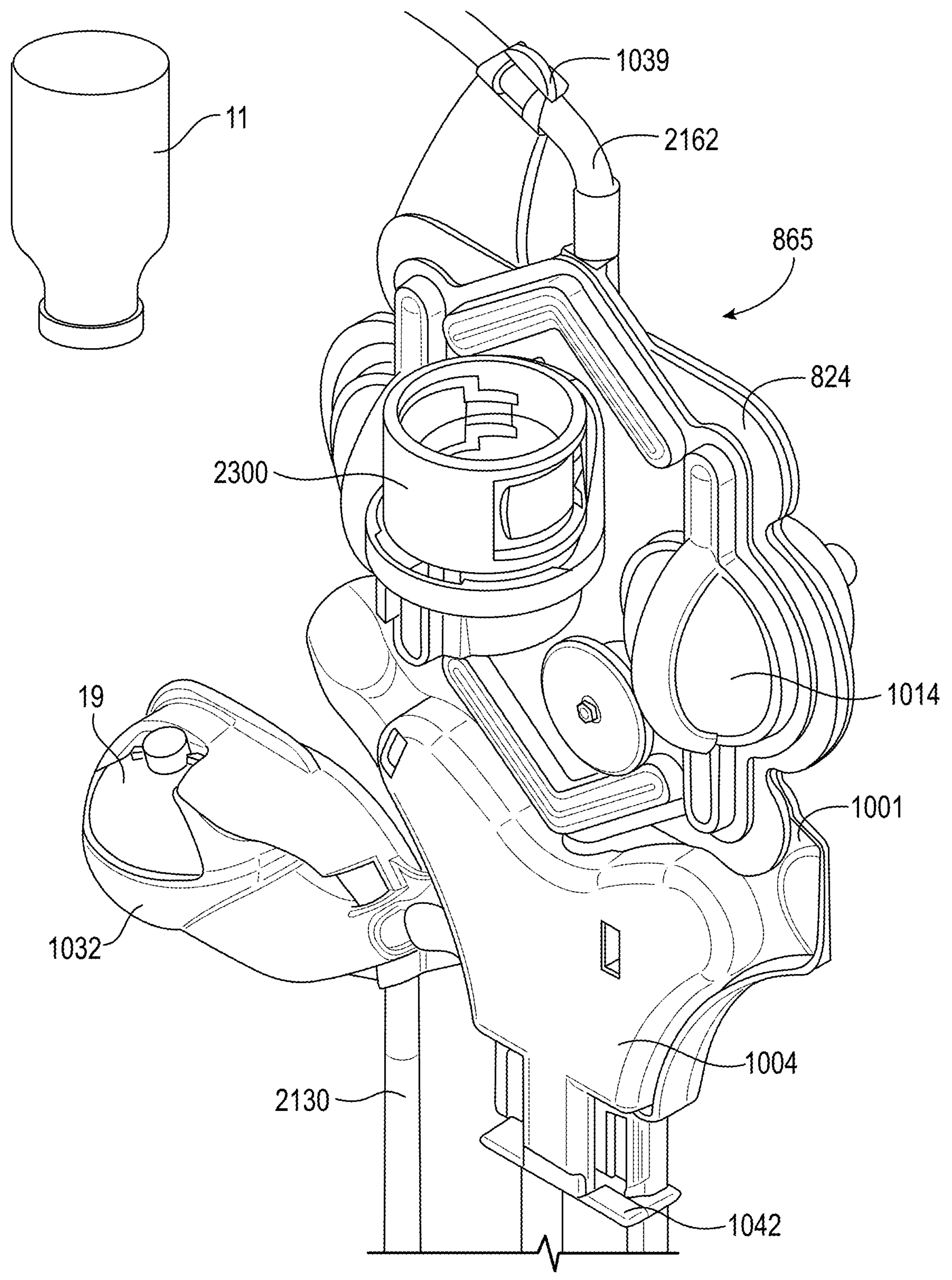
FIGS. 18-19 are perspective views of a blood pump assembly having a medication holder in an illustrative embodiment.
Figure 19:
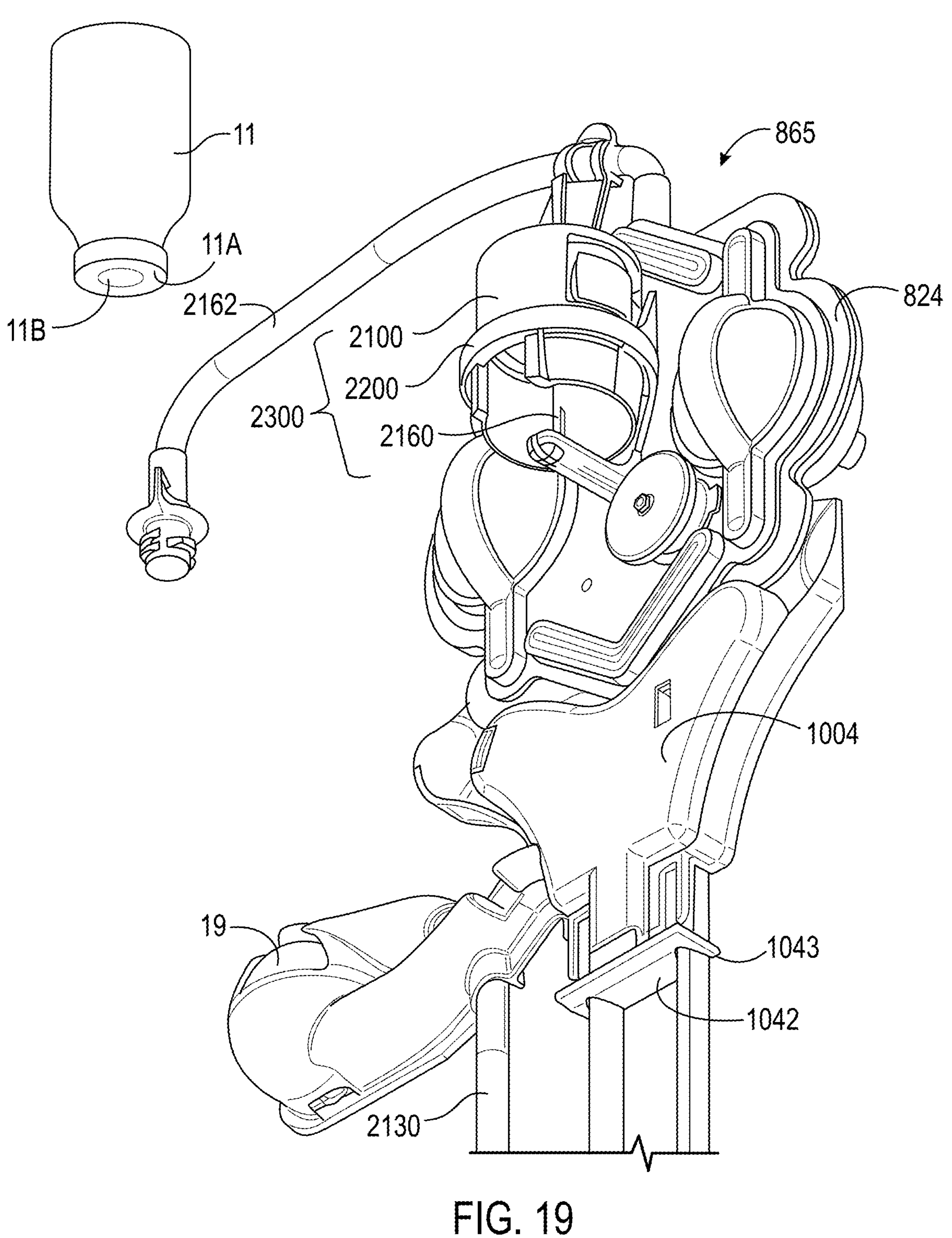

FIGS. 18 and 19 shows perspective views of a blood pump assembly 865 including the blood pump cassette 824. The blood pump cassette 824 includes a vial receptacle or vial receiver 2300 for holding or cradling or supporting a medication vial 11. The medication vial 11 contains a medication used in hemodialysis, e.g., an anticoagulant. The vial receiver 2300 supports the medication vial 11, which is impaled onto a hollow spike 2160 that provides a fluid conduit from the vial to fluid paths in the blood pump cassette 824 that fluidly connect to the metering pump 1015 (shown schematically in FIG. 3). The vial receiver 2300 aligns the medication vial with the hollow spike 2160 before the medication vial 11 makes contact with the hollow spike 2160.

Figure 20:
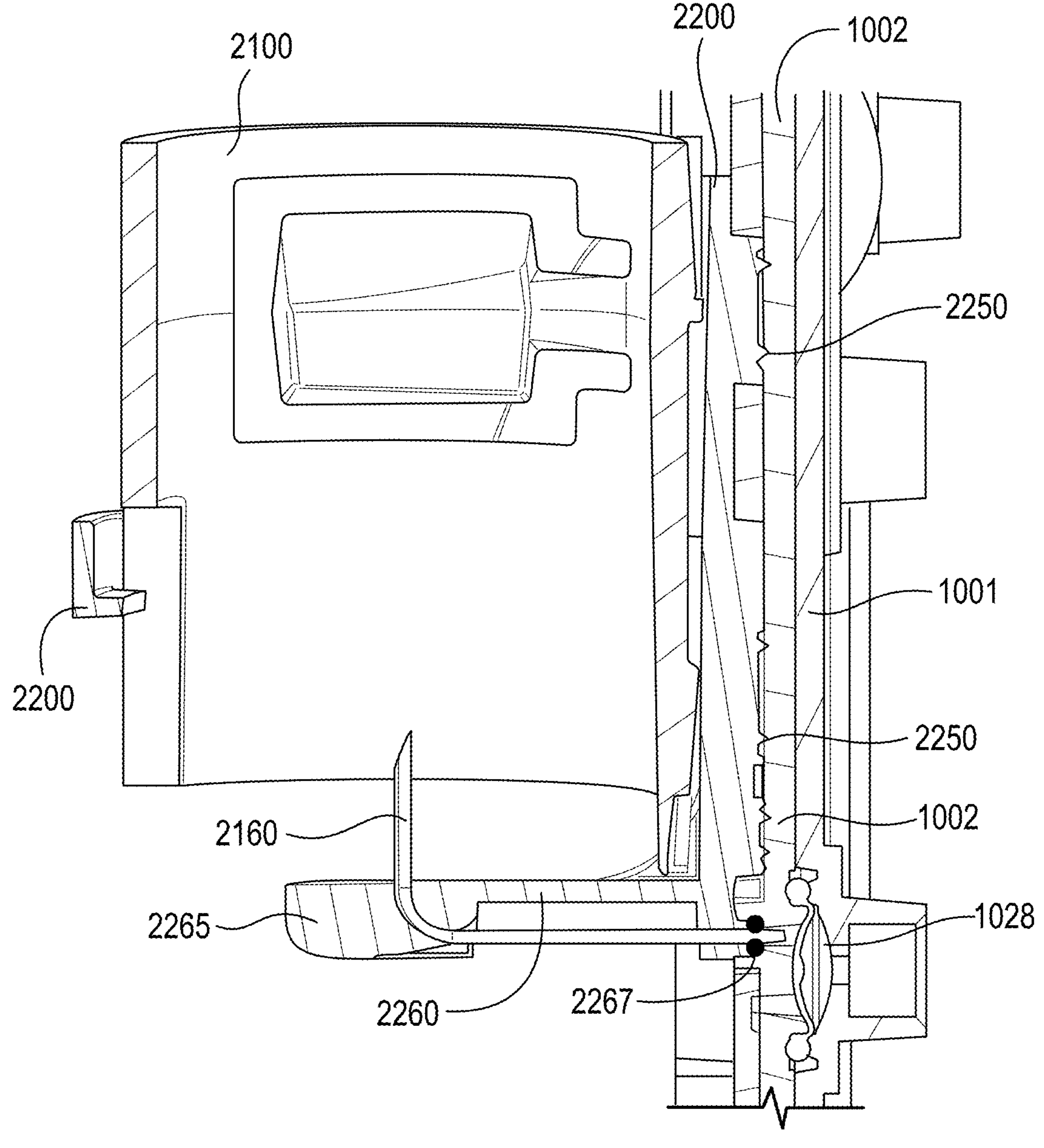
FIG. 20 is a cross-sectional view of the medication holder mounted on the blood pump cassette.

Referring now to FIG. 20, the vial receiver 2300 encourages central axis of the medication vial 11 to be aligned with vertical axis of the hollow spike 2160 so that the hollow spike 2160 enters the medication vial in the center of a pierceable cap 11A. The vial receiver 2300 also serves to prevent the medication vial 11 from being spiked at an angle with respect to the inverted top of the medication vial 11A. Spiking the top of medication vial 11 in a substantially perpendicular manner reduces fluid leaking from the vial 11 around the outside of spike 2160. Referring now to FIG. 19, in one example, the pierceable cap comprises a pierceable elastomer element 11B held to the medication vial 11 by a ring 11A that is mechanically attached to the medication vial 11.

Continuing to refer to FIG. 20, the vial receiver 2300 comprises a vial support 2200, a vial holder 2100 and a hollow spike 2160. The vial holder 2100 is mounted in a vial support 2200. The vial support 2200 is attached on the front plate 1003 of the blood pump cassette 824. In an example, the vial support 2200 is welded to the mid-plate 1002 at one or more locations 2250. The vial support 2200 may be welded to the mid-plate 1002 by laser welding, ultrasonic welding or another technique to bond the vial support to the mid-plate.

Figure 23:
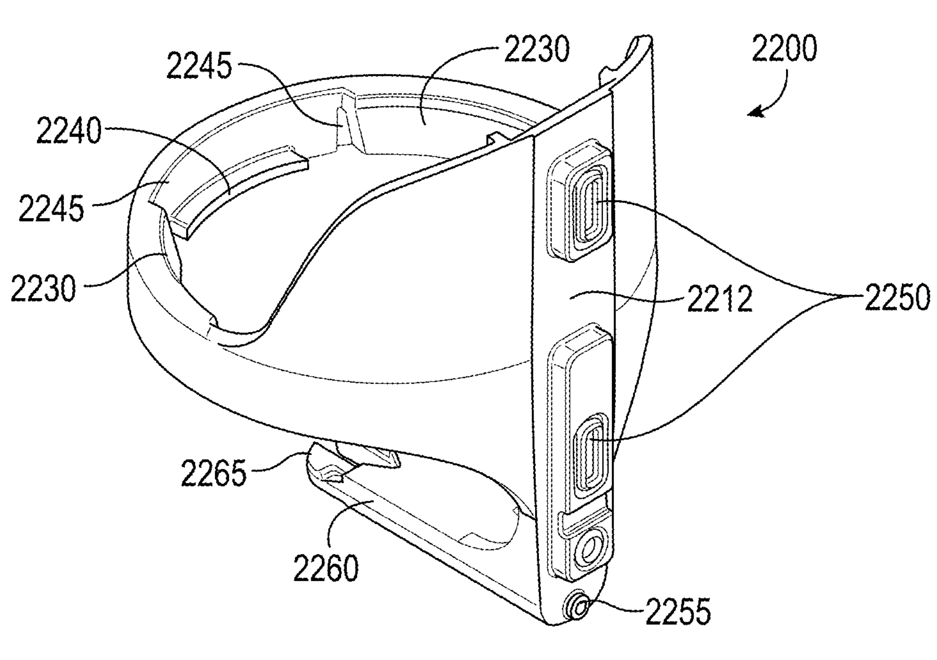

Referring now to FIGS. 22, 23, the vial support 2200 comprises vertical spine 2212, a support ring 2220 and a support arm 2260. The mounting protrusions 2250 may include rib or other surface features to facilitate ultrasonic or laser welding. Referring now to FIG. 20, the mounting protrusions 2250 on the vertical spine 2212 extend through an opening in the front plate 1003 to the mid-plate 1002. The vertical spine 2212 of the vial support 2200 is fused to the mid-plate 1002 of the blood cassette. The weight of the medication vial 11 is supported by the support arm 2260 when the medication vial is fully impaled on the hollow spike 2160. The spike 2160 comprises a metal tube a 90 degree bend, where the first end is sharpened and the other end extends into the flow paths in the blood cassette via the heparin valve 1028. The horizontal portion of the spike 2160 between the bend and the flow path is inserted in and supported by the support arm 2260.

Referring now to FIGS. 21A-23, the vial holder 2100 (FIG. 21A-C) slides into the support ring 2220 (FIG. 23) of the vial support 2200. The rails 2178 (FIG. 21A-B) slide into the opening 2245 of the support ring 2220 (FIG. 23). Referring now to FIG. 23, the openings 2245 are in part defined by the protrusion 2240 and the ramps 2230 In addition, guides 2215 on the vial support receive vertical protrusion 2152 (FIG. 21A-B) of the vial holder 2100. The rails 2178 and guides 2215 assure that the vial holder 2100 (FIG. 21A) is in the correct circumferential orientation with vial support 2200 and the location of the hollow spike 2160. During assembly, ramps 2174 on the vial holder 2100 (FIG. 21A) slide past opposing ramps 2230 in the vial support 2200. The opposing ramps 2230 snap into recesses 2176 (FIG. 21A) once the vial holder is fully inserted, which axially locates and secures the vial holder 2100 on the blood pump cassette 824 (FIG. 19). Referring again to FIG. 21A-B, bosses 2170 on the vial holder 2100 contribute to centering the vial holder 2100 in the vial support 2200 by contacting the gussets 2210 (FIG. 23). Axial loads are transferred from the vial holder 2100 to the vial support 2200 via the step 2177 that contacts the top surface of ring 2200. The ring 2220 (FIG. 23) is strengthened by gussets 2210 that connect the spine 2212 to the ring 2220.

Referring now to FIG. 21A, the cylindrical shape of the vial holder 2100 provides a strong, tough and resilient guard around a medication vial 11 impaled on the hollow spike 2160. The continuous hoop of material in the cylinder walls 2173 at the top and middle of the vial holder 2100 provide protection against shocks and impacts.

Referring now to FIG. 21A-21C, the vial holder 2100 includes two pads 2190 that are connected to the vial holder 2100 by living hinges 2192. Each pads 2190 is configured to pivot about a vertical axis that is parallel to the first end of the spike 2160 and press the medication vial 11 toward a center plane. In an example, the center plane is defined by vertical and horizontal portions of the hollow spike 2160. In an example the center line passes through the first end of the hollow spike 2160 and is perpendicular to the front plate 1003. The body of the medication vial 11 deflects the pads 2190 away from the center plane as the medication vial is inserted into the vial holder 2100. Each blades is formed to apply approximately equal force on the medication vial 11 to center the medication vial in the center plane.

In an example the blades have tapered surfaces 2194 above the contact surface 2193 that provide a ramp that contacts the shoulder of the medication vial 11 as it is inserted in the vial receiver 2300. The tapered surfaces 2194 are angled with respect a vertical axis defined by the hollow spike 2160. The tapered surfaces 2194 facilitate the insertion of the vial 11 into the vial receiver 2300 and reduce the possibility that the insertion of the vial will be stopped by the top edge of the pad 2190. The pads 2190 are formed to have an inner radius that is smaller than the inner radius of cylinder walls 2173. The smaller radius of the pads accommodates smaller vial sizes.

In another embodiment, the smaller radius of the pads the urges the outside diameter of the medication vial against the inner wall 2172 of the vial holder 2100. In this example the pads 2190 centers the medication vial 11 on the vertical portion of the hollow spike 2160 as indicated by location 2168. In this embodiment, the pads 2190 may contact the medication vial 11 with a narrow surface 2193, while pressing the medication vial 11 against the vertically extensive curve of the inner surface 2172, so that medication vial is both centered on and aligned with the vertical portion of the hollow spike 2160.

Referring now to FIG. 20, 23, the hollow spike 2160 is located in the vial support arm 2260. The hollow spike 2160 extends through the mid-plate 1002 to a port of the heparin valve 1029 that leads to the metering pump. The metering pump, as described elsewhere, controls the flow of the medication from the medication vial 11 to the blood circuit at a location between the blood pumps and the dialyzer. The hollow spike is fluidly sealed to the mid-plate 1002 by an O-ring 2267 captured between the spike support 2200 and the mid-plate 1002. The vial support 2200 may include an O-ring compression element 2255 that is received by a matching depression in the mid-plate 1002.

Blood Pump Cassette

Figure 24:
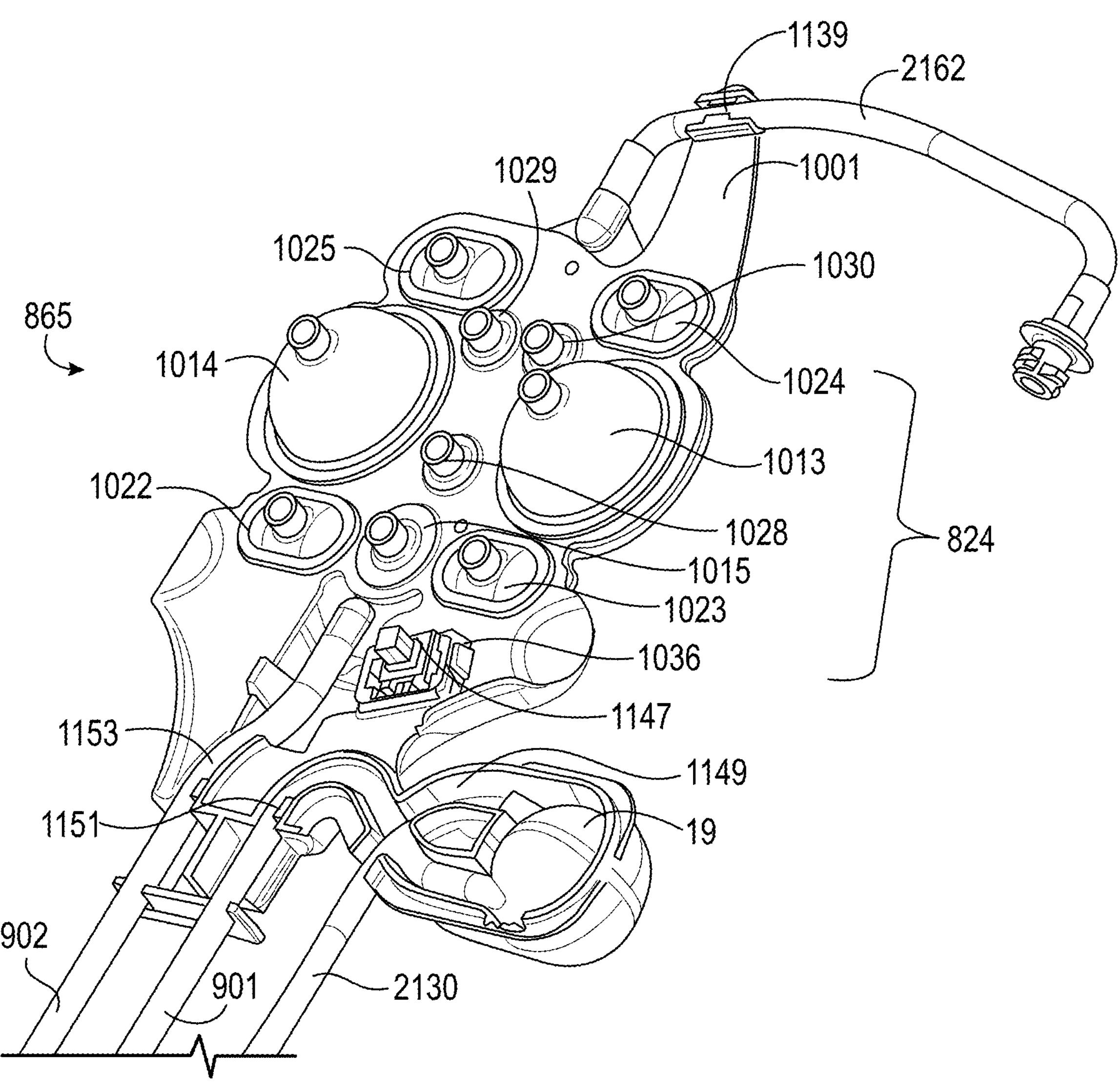
FIG. 24 are perspective views of the blood pump assembly.

Referring now to FIG. 24, the valves and pumps of the blood pump cassette 824 can be seen in on the actuation side of the blood pump cassette where the back plate 1001 is visible. The blood pump cassette 824 includes a left pod pump 1013 and a right pump 1014 for pumping fluid, which may be blood in the case of a hemodialysis apparatus through the fluid flow side of the cassette 824. The valves 1022-1025 are inlet and outlet valves for the pod pumps 1013, 1014. A metering pump 1015 is fluidly connected to the air vent 1019 via valve 1029 and to the medication port 1039 via valve 1028. The metering pump is also fluidly connected to the blood flow line 205 (FIG. 3) via valve 1030. The medication port is fluidly connected via the spike to 2160 to the vial 11.

Figure 25A:
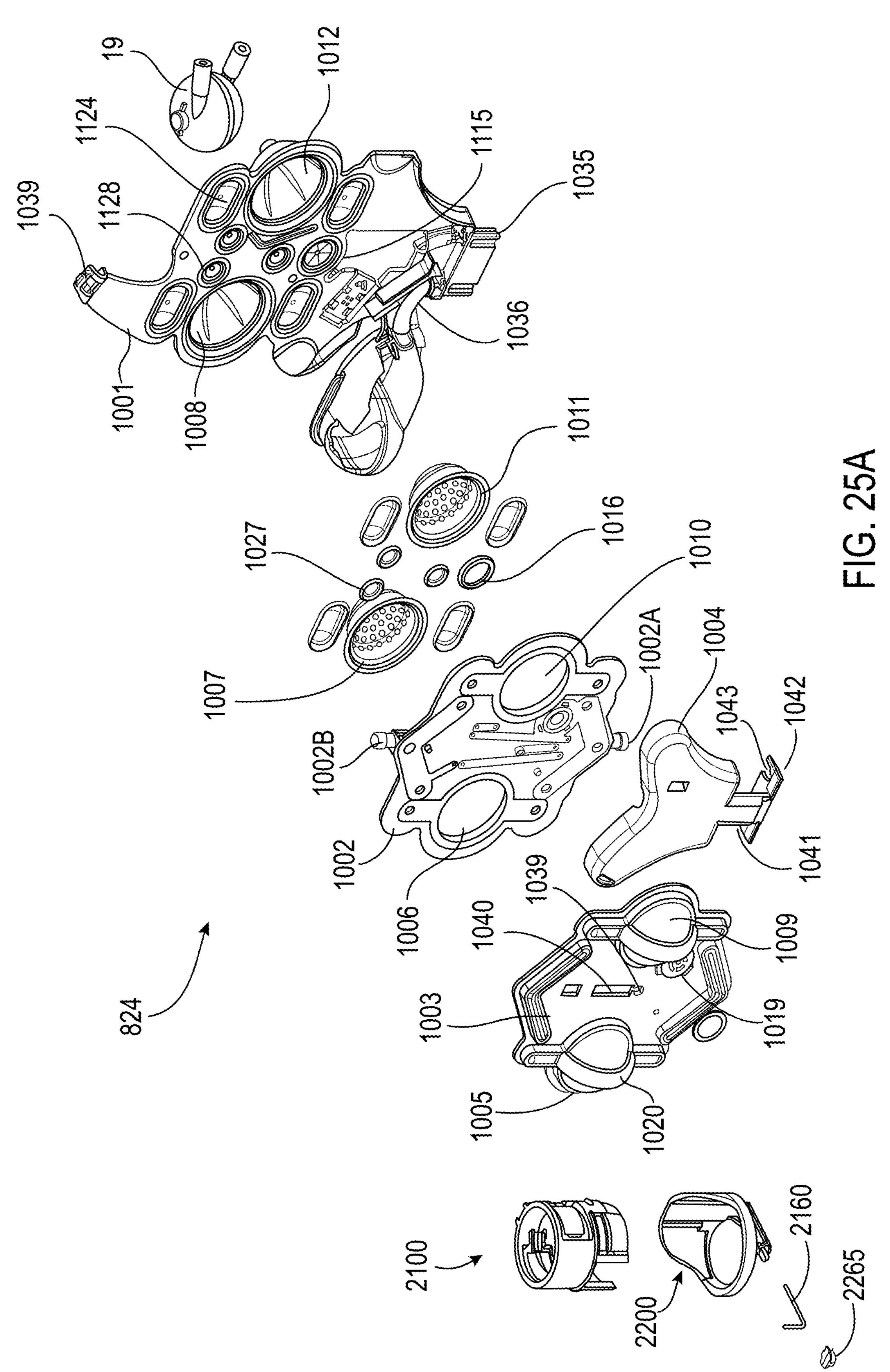
FIG. 25A is a front exploded view of the blood pump cassette of FIG. 17.
Figure 25B:
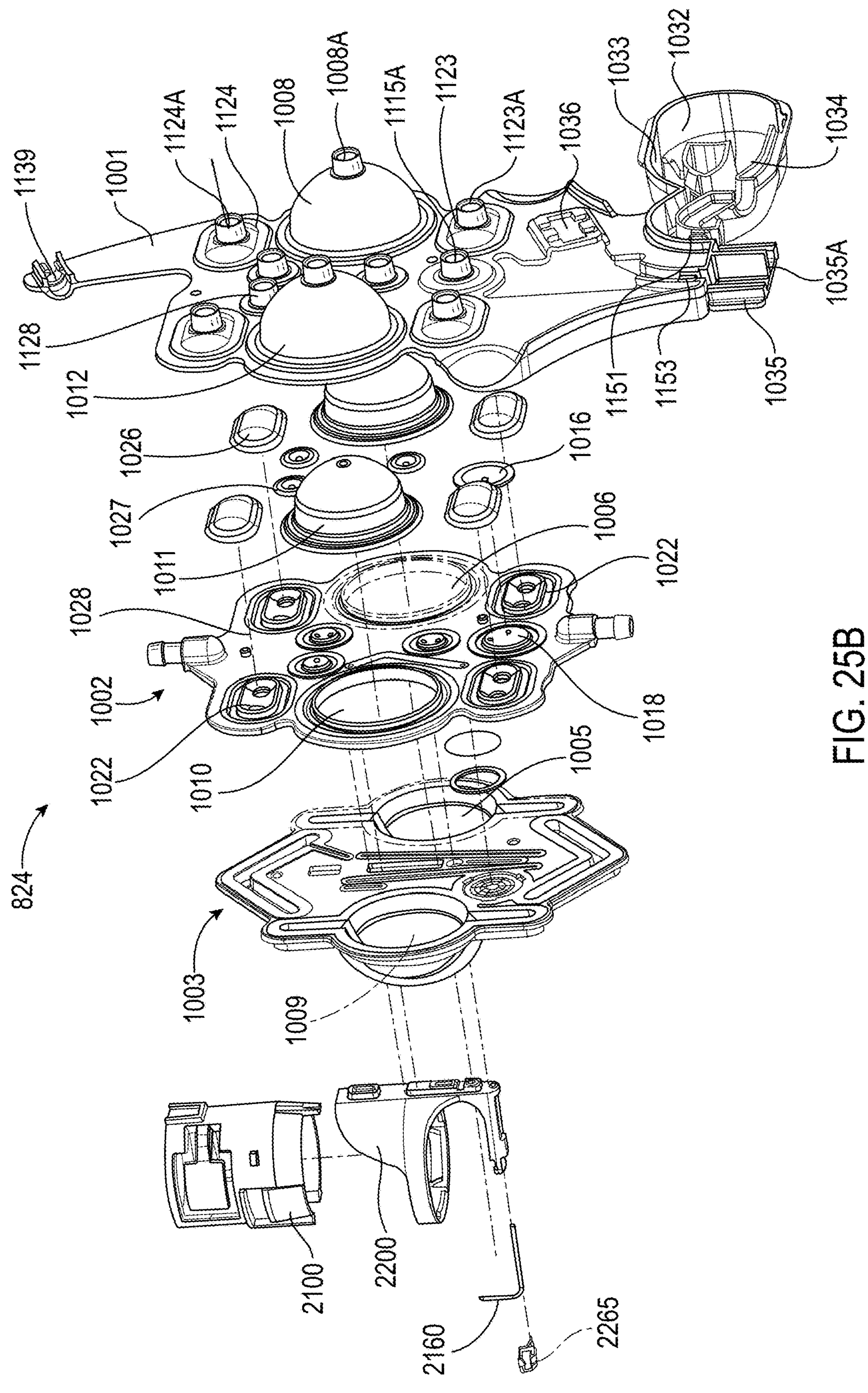
FIG. 25B is a rear exploded view of the blood pump cassette of FIG. 17.

FIGS. 25A, 25B show exploded, perspective views of an of the blood pump cassette 824. The blood pump cassette 824 is a physical implementation of the blood circuit in FIG. 3. FIG. 25A shows a front-perspective, exploded view of the cassette 824 having a back (actuation side) plate 1001 that includes a tubing organizer formed with the back plate on a single molded piece of material. FIG. 25B shows a back-perspective, exploded view of the cassette 824.

The cassette 824 includes a back plate 1001 that forms rigid outer walls of the actuation chambers of various valves and pumps, a mid-plate 1002 that holds various valve and pump diaphragms and helps to define various flow paths in cassette 824, and a front plate 1003 that forms rigid outer walls of some of the fluid chambers of the various valves and pumps of cassette 824. The cassette 824 optionally further includes a protective cover 1004 that is attachable to the front side of back plate 1001.

A medication vial may be coupled to a vial receiver 2300 having a hollow spike that places the vial in vial receiver 2300 in fluid communication with a fluid port 1039 in the front plate 1003. The vial may be filled, for example with anticoagulant medication for use during dialysis, or it may be empty and available for use during cleaning and disinfection procedures either before or after a dialysis treatment.

Continuing to refer to FIGS. 25A, 25B, the pumps 1013 and 1014 (also referred to herein as pod pumps) may be actuated by a pressured air or other gases that enters cassette 824 through ports on back plate 1001. The left pod pump 1013 includes a rigid chamber wall 1005 formed on the front (or top) plate 1003, a rigid chamber wall 1008 formed on the back (or bottom) plate 1001, an aperture 1006 formed on the mid-plate 1002, and a flexible membrane 1007 that can flex between the rigid chamber walls 1005 and 1008. The space between the rigid chamber wall 1005 and the flexible member 1007 defines the fluid or blood side (i.e., fluid chamber) of the left pump 1013 and the space between the flexible membrane 1007 and the rigid chamber wall 1008 defines the pneumatic side (i.e., control chamber) of the left pump 1013. Likewise, the right pod pump 1014 includes a rigid chamber wall 1009 formed on the top plate 1003, a rigid chamber wall 1012 formed on the bottom plate 1001, a hole 1010 formed on the mid-plate 1002, and a flexible membrane 1011 that can flex between the rigid chamber walls 1009 and 1012. The space between the rigid chamber wall 1009 and the flexible member 1011 defines the fluid or blood side (i.e., fluid chamber) of the right pump 1009 and the space between the flexible membrane 1011 and the rigid chamber wall 1012 defines the pneumatic side (i.e., control chamber) of the right pump 1014.

Each of the pod pumps 1013 and 1014 include a pair of membrane-based entry/exit valves 1022-1025 having each valving chamber formed between a valve station 1022 on the mid-plate 1002 and a diaphragm 1026. The valve stations 1022 include two fluid ports through the mid-plate and features to receive a thickened edge of the diaphragm 1026. Each entry/exit valve 1022-1025 is controlled by pneumatic pressure supplied through port 1124A to an actuation chambers defined by the chamber 1124 in the back plate 1001 and the diaphragm 1026. When the valve diaphragm is pulled away from the adjacent holes in mid-plate 1002 by pneumatic pressure and/or by the restoring force of the diaphragm, liquid can flow through the valve. The movement of liquid through the valve is primarily driven by the action of the pump diaphragm fluidly connected to the valve.

The valves may be actuated by the application of positive or negative pneumatic pressure on individual flexible membranes 1026 via control ports 1124A on the bottom plate 1001. The fluid valves can be opened and closed to direct fluid flow when the pod pumps are pumping. Depending on how the valve actuations are sequenced in relation to the actuation of their associated pump, fluid may be pumped either in a forward direction, or in a backward direction. Non-limiting examples of pod pumps are described in U.S. patent application Ser. No. 11/787,212, filed Apr. 13, 2007, entitled "Fluid Pumping Systems, Devices and Methods,"

incorporated herein by reference. The pod pumps 1013 and 1014 may be operated in any suitable fashion, e.g., synchronously, asynchronously, in-phase, out-of-phase, etc., with fluid flow in either direction.

Continuing to refer to FIGS. 25A, 25B a metering pump 1015 in cassette 824 can be used to control the flow of medication from an attached vial (such as anticoagulant) into a fluid path within the cassette 824. The metering pump 1015 may also be used to pump air through the fluid paths of cassette 824. The metering pump 1015 construction is similar to the valves 1022-1025, where the pumping chamber is defined by a pumping station 1018 on the mid-plate and the metering pump diaphragm 1016. The metering pump actuation chamber is defined by the rigid chamber 1115 on the back plate 1001 and the metering pump diaphragm 1016. The metering pump is actuated by pneumatic pressure supplied through port 1115A to the actuation chamber. Fluid moves through the pump through the metering pump 1015 through 3 holes in the mid-plate metering pump station 1018 that each lead to separate metering flow paths.

The metering pump 1015 includes three passageways connected to the fluid chamber 1018 defined in the mid-plate 1002. One passageway allows air from vent 1019 to be pulled into the metering pump 1015, a second passageway allows the air to be pushed to the spike/source container connected to vial holder 2300, and also alternately draws liquid from the source container or vial, and the third passageway allows the liquid from the source container to be pushed by the metering pump 1015 to a main fluid line connected to first pump 1013 (or pump 1014 in an alternate embodiment). Valves 1028, 1029, and 1030 determine whether the metering pump 1015 moves fluid or air, and in which direction.

The cassette 824 includes an air vent port 1019. Air may be introduced into the flow path of metering pump 1015 to equalize pressure in an attached vial with ambient pressure. In this case, valve 1030 closes flow between metering pump 1015 and the main flow path of the first 1013 (or second 1014) pump. In some cases, metering pump 1015 may also introduce air into the main flow path of the first 1013 or second 1014 pumps in order to allow a system controller to control the emptying of the blood or liquid carrying components of the system.

The pod pumps 1013 and 1014 include raised flow path 1020 and 1021 on the pump chamber walls 1005 and 1009, respectively. The raised flow paths 1020 and 1021 allow fluid to continue to flow through the pod pumps 1013 and 1014 after the diaphragms (i.e., flexible membranes) 1007 and 1011 reach the end of a stroke.

The ports on the back of the back plate of the blood pump cassette 824 plug into the control ports in the blood pump receptacle 515 (FIG. 16) that is mounted on the front panel 511 (FIG. 12B). The pump actuation ports 1008A in FIG. 25B plug into the control ports 617 in FIG. 16. The inlet/outlet valve actuation ports 1124A in FIG. 25B plug into control ports 616 in FIG. 16.

Referring again to FIGS. 25A, 25B, the bottom plate 1001 includes various organizer features integrated thereon. The bottom plate 1001 includes an air trap retaining member 1032 having tube guides 1033 and 1034 defined on the bottom plate 1001. The tube guides 1033 and 1034 guide a tube to and from an air trap disposed within the air trap retaining member 1032. The bottom plate 1001 also includes additional tube guides 1035 and 1039. The bottom plate 1001 also defines a receiving portion 1036 to receive an electrical connector that may be used in an arrangement to monitor for disconnection of the arterial or venous lines from a patient during therapy.

Protective Cover

Figure 26A:
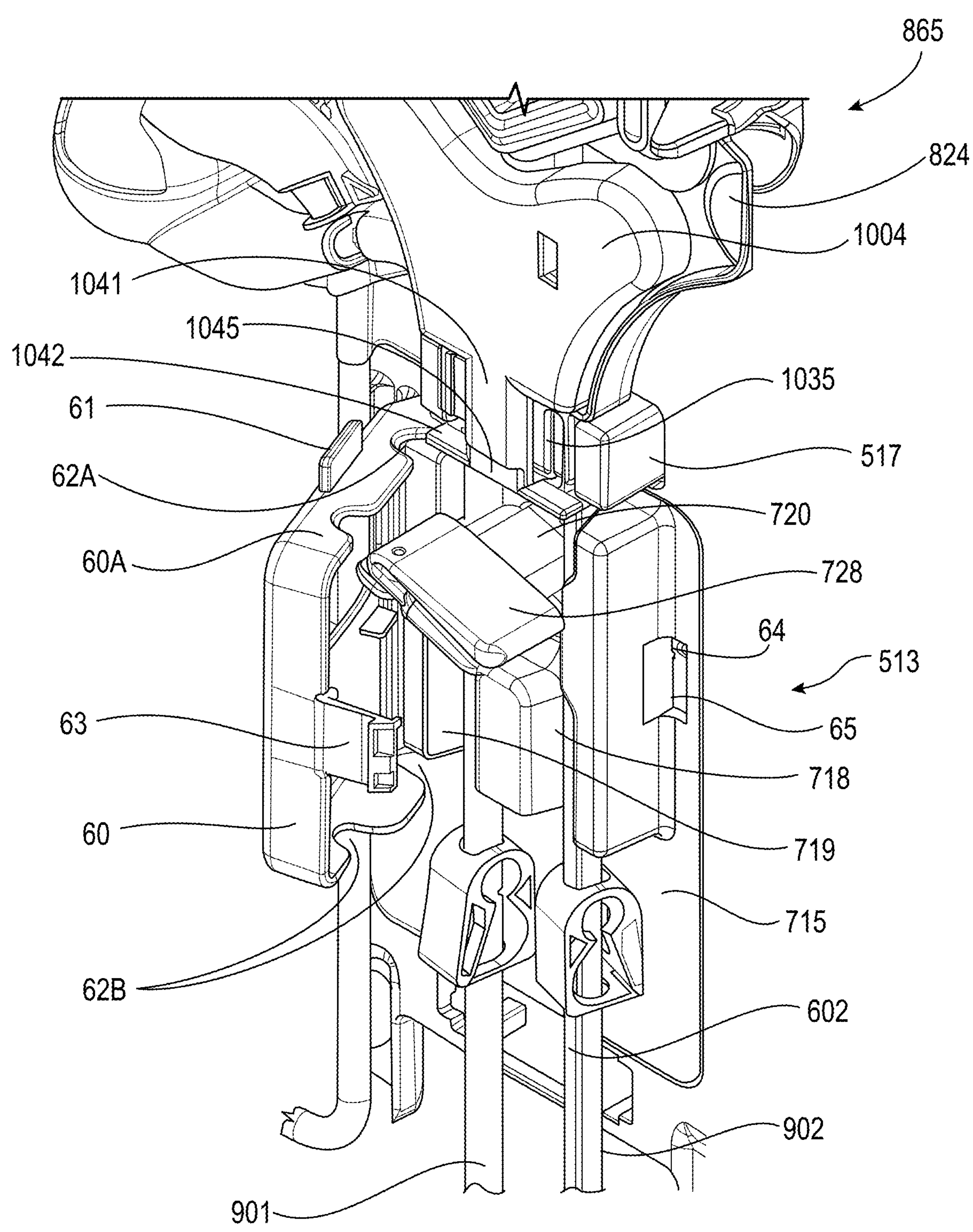
FIG. 26A is a right perspective view of the blood pump assembly installed on the front of the front panel with AIL sensor and occluder assembly.

Referring now to FIG. 26A, the protective cover 1004 covers at least the ADS wires that emerge from the blood lines and the ADS electric plug 1147 (FIG. 24) that electrically connects the ADS wires to the ADS circuit in the dialysis unit 51 at ADS receptacle 520 (FIG. 12B). The protective cover 1004 includes an extension 1041 and a flange 1042 that together with tube guides 1035 press the patient blood lines 901, 902 into the air-in-line sensors 517. Referring to FIG. 15, the AIL sensors 517 comprise an open channel 517C, 517D for each patient blood lines that is oriented vertically on the face of the front panel.

Referring again to FIG. 26A, in order to allow hemodialysis therapy to occur, the patient blood lines 901, 902 need to be correctly positioned in the AIL sensors 517 and in the occluder assembly 513 which is directly below AIL sensors. The occluder and how it functions are described on more detail below. The protective cover 1004 and occluder door 60 are configured to allow the occluder door to close only when the blood lines are correctly positioned in both the AIL sensor and occluder.

Figure 26B:
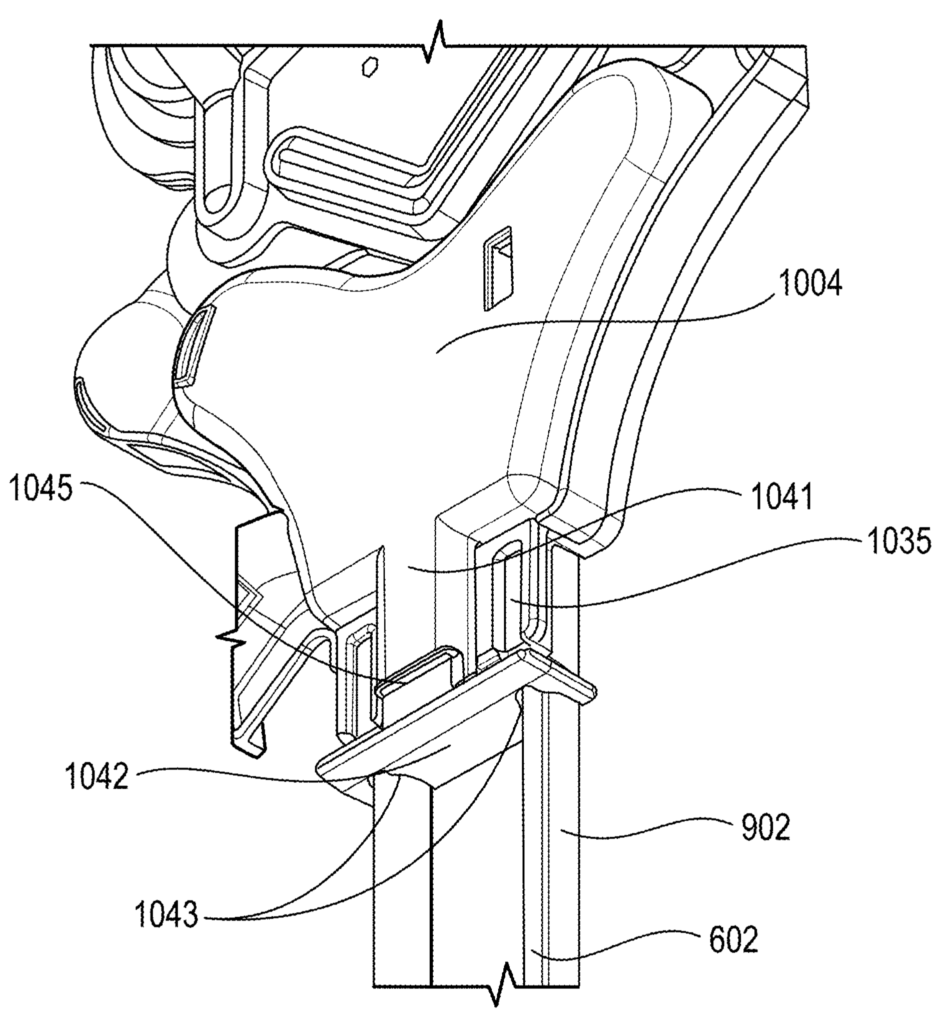
FIG. 26B is a right perspective view of the blood pump assembly.
Figure 26C:
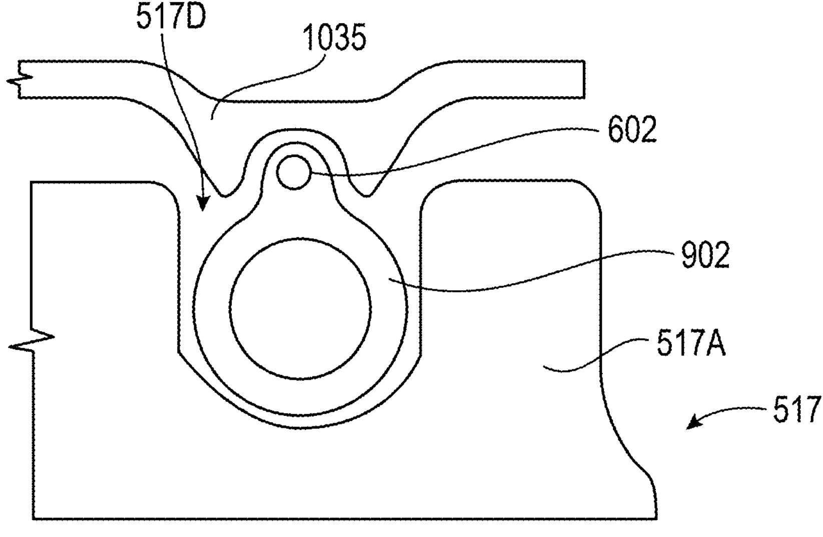
FIG. 26C is a cross-sectional view of a patient blood line in the AIL sensor.

The tube guides 1035 press on the patient blood lines 901, 902 into the slots of the AIL sensors 517. Referring now to FIG. 26B, the flange 1042 includes a notch 1043 for each of the blood lines. The notches 1043 holds the unconstrained sections of each of the blood lines in a position that is aligned with slots of each AIL sensors and aligned with tube guides 1035. Referring now to FIG. 26C, which shows a blood line 902 in one of the AIL sensors, the tube guides 1035 receives the second lumen 602 of the blood line. The tube guides 1035 press the patient blood lines 902 into the AIL sensor slots 517D and orient the second lumen 602 away from the sensor 517 walls. The tube guide 1035 orients the dual lumen patient blood lines 901, 902 so that the second lumen faces away from the front panel to improve air-in-line detections and improve occluding the blood lines in the occluder assembly 513. The second lumen 602 and the ADS wire in the second lumen could prevent good positioning of the tube in the AIL sensor 517 if the second lumen were in contact with the sides or bottom of the AIL slot 517D. Here, good positioning of the blood lines 901, 902 in the AIL sensor slot includes the first lumens of the blood lines are concentric with the curved bottom of the sensor slot 517D. The tube guides 1035 by gripping or receiving the second lumen assures that the second lumen and ADS wire are located away from the sides of the AIL slots 517C, 517D. Similarly, the tube guides 1035 assure that second lumen is not against the sides of the pathway walls and the occluder in the occluder assembly. In the occluder assembly, the second lumen may interfere with occluding the blood line when the second lumen and wire are against the compressing elements of the occluder.

The notches 1043 in the flange 1041 constrain the patient blood lines 901, 902 from moving horizontally away from the AIL sensor slots 517A, 517D. The notches 1043 grip the patient blood lines 901, 902 below the AIL sensor 517 and press the blood lines against the face of the front panel 511 so that the blood lines are engaged into slots in the AIL sensor 517 and against the front panel just above the occluder assembly 513.

Referring again to FIG. 26A, the installation of the blood pump assembly 865 includes positioning the patient blood lines 901, 902 in the AIL sensor and the Occluder assembly 513. The occluder assembly 513 includes a base 715 and two pathway 718, 719 for receiving tubing on either side of the occluding member 720. The pathways 718, 719 are indentations within base 715 shaped for receiving the patient blood lines. The pathways 718, 719 are substantially straight. Positioned on base 715 is the occluding member 720 that is rotationally moveable about a pivot (not shown). The occluding member 720 can partially rotate before it contacts an outer wall of the pathways 718, 719. The occluding member 720 may be constructed such that when it is rotated around the pivot, occluding element 720 enters and at least partially obstruct the pathways 718, 719. In order to install the patient blood lines 901, 902 in the pathways 718, 719, the occluding member 720 is manually rotated to an open position, where the occluding member is out of the pathways 718, 719. The occluder is turned by manually turning the grip member 728. In another embodiment, a controller in the hemodialysis unit rotates the occluding member 720 to install the blood lines 901, 902 in the pathways 718, 719. Once the patient tubes 901, 902 are positioned at or near the bottom of the pathways 718, 719, the occluding member 720 is allowed to rotate closed and pinch closed each of the patient blood lines 901, 902. The grip member 728 can be formed as part of, or otherwise immobilized with respect to occluding member 20.

Figure 27:
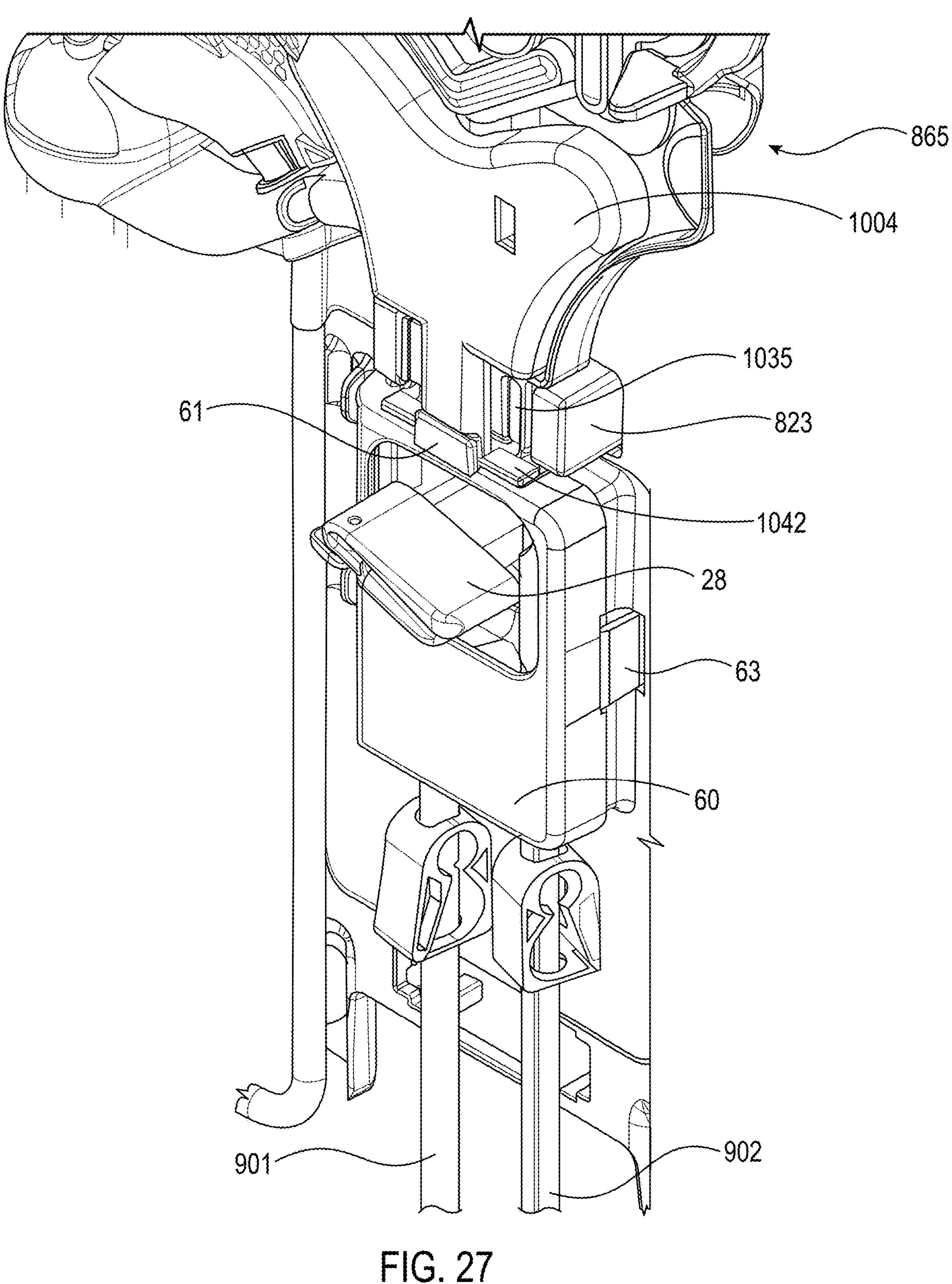
FIG. 27 is a right perspective view of the blood pump assembly installed on the front of the front panel with AIL sensor and occluder assembly with the occluder door closed

Referring now to FIGS. 26A, 27, an occluder assembly 513 includes a door 60 that covers the patient blood tubing and holds the blood tubing in the pathways 718, 719 when the occluding member 720 is rotated into the open position. Safe operation of the hemodialysis may depend on the occluder assembly 513 occluding the patient tubing 901, 902 during an alarm or an alert. Successful functioning of the occluder depends on the patient tubing 901, 902 being located in the pathways 718, 719. The occluder door 60 both holds the patient lines 901, 902 in the pathways 718, 719, when the door 60 is closed. In some cases, the occluder door 60 includes door notches 62A, 62B that aid in properly aligning the blood tubing within the pathways. The door notches 62A, 62B maintain the patient blood lines in the correct position in the pathways 718, 719 when the occluder member is in the open position. The occluder door 60 can only close when the door notches line 62A, 62B line up with the patient lines 901, 902. If the occluder door is not closed, then the tubing may not be in the correct position to be occluded by the occluding member 20. Thus in an embodiment, the hemodialysis unit controller will only open the occluder member 20 or proceed with therapy, when the occluder door 60 is closed.

Safe operation of the hemodialysis may depend on reliably detecting air in the patient blood lines with the AIL sensor. The AIL sensor is most reliable when the patient blood lines are fully inserted in the AIL slots 517C, 517D. The occluder door 60 and the protective cover extension 1041 are configured to assure that the patient lines 901 902 are fully inserted in the AIL slots, when the occluder door is closed.

The occluder door 60 includes a door tab 61 that extends vertically off the top of the door 60. In an instance where the blood pump assembly is installed on the front panel, the door tab 61 extends over the flat recess 1045 on the protective cover extension 1041. In this instance, the occluder door 60 is only able to close, when the protective cover extension has fully seated the patient blood lines 901, 902 in the AIL slots. The flat recess 1045 is slightly lower than the main section of the protective cover 1004 to receive the door tab 61. The door tab 61 and the flat recess are configured so that the occluder door 60 can only close when the blood lines are fully pressed into the AIL slots.

The occluder assembly 513 includes a detector 64 that provides a signal to the hemodialysis unit controller when the occluder door 60 is closed. In one embodiment the occluder door includes a door latch 63 with a living spring that latches with the door slot 65. The controller detects that the door 60 is closed when the door latch 63 is inserted into the door slot 65. The detector 64 detects the correct position of the door latch 63 with any of a number of know sensors to detect the position of a movable component include visible or IR light sensor that detects a broken light beam, a hall sensor that detects the position of a magnet on the door or a micro switch that is displaced when the door tab is 63 is inserted into the door slot 65.

Thus, the hemodialysis controller can detect unsafe operating condition when the occluder door is not fully closed. In one case, the patient lines may not be sufficiently pressed into the AIL slots. In another case, the patient lines may be improperly positioned within the occluder assembly. In either case, the controller will prevent therapy or stop pumping operation until the unsafe conditions have be corrected.

In one embodiment, the occluder door 60 can be constructed of transparent material such as a polycarbonate resin thermoplastic (LEXAN) (or other suitable plastic, polyethylene, polypropylene, or the like) to allow the user to visually confirm the proper positioning of the tubing in pathways 18 and/or 19, and the position of occluder 20.

In another embodiment, a switch 64 may be mounted on base 715. The binary switch detects when the occluder door 60 is closed. In one embodiment, the switch detects when the cover latch 63 is inserted to the receiving slot 65 in the base. The controller will monitor the switch state to determine if the occluder door 60 is completely or properly closed. The indication by the switch of an open or incompletely closed occluder door 60 can be transmitted to an electronic control system, which in turn can trigger and transmit an alarm condition to the user and stop the blood pumps in the blood pump cassette 824 and the dialysate pumps in the dialysis cassette assembly. In addition or separately, the electronic control system will not move the occluder 20 into the open position that allows the flow of liquid (blood) flow through the tubes 901, 902. Receiving a positive signal that occluder door is closed may also cause the controller to perform other functions, such as, for example, pumping blood with the blood pump cassette 824 through the tubes 901, 902.

In another example, the detector 64 reports a binary signal to the controller, where one signal indicates the occluder door 60 is closed and a second signal that the occluder door 60 is not closed. The hemodialysis controller monitors the switch 64 and will prevent at least the blood pump from operation if the switch 64 has not been tripped or detected that the door is not closed. In one example, the hemodialysis controller will prevent therapies from starting if the door detector 64 does not indicate that the occluder door 60 is fully closed.

In one example, the occluder door 64 cannot close and the controller will not start or continue therapy if any of the following conditions occur: a) the patient blood lines 901, 902 are not seated in the AIL sensor, b) the blood lines are not inserted in the pathways 18, 19 in the occluder. This can be understood in that the occluder door closes only when the blood lines are located within the occluder where the cutouts 62A, 62B fit over the installed blood lines.

Drain Cassette

In another aspect, as shown in FIG. 13, an embodiment of a front panel assembly 511 may include a modular drain assembly (or drain cassette) 815 having connection points 814 into which the arterial and venous blood lines may be connected. As shown in FIG. 6 and connected to the directing circuit 142, the drain circuit 145 includes detachable connection 67 of venous line 204 and the arterial line 203. The drain circuit 145 includes a drain valve 206 fluidly connected to the venous blood line 204. Alternatively or in addition, a valve is fluidly connected to the arterial blood line 203. is mounted in the on line the drain When attached to the drain circuit 145, the detachable venous line 204 and detachable arterial line are fluidly connected to a common space 147 that is connected to the circuit drain 31. The fluid path in the drain circuit 145 between the common space 147 and the arterial line 203 path includes one or more conductivity and temperature sensors.

Referring now to FIG. 12B, the drain circuit is implemented in a drain cassette mounted to the front panel 511 at the drain recess 600. The drain recess 600 includes a liquid port 620 that is fluidly connected to the drain for the dialysis unit 51. The drain recess 600 includes an electrical receptacle 610 that is electronically connected to the FPGA board that is part of the controller. A pneumatic port 630 provides positive or atmospheric or negative pressure to the dialysate cassette.

Referring now to FIGS. 3, 6, water, dialysate solution or another fluid may be introduced into the blood pathways of dialysis system 5 through the semi-permeable membrane of dialyzer 14 in order to expel air from the blood pathways and to prime the blood pathways, or in order to clean and disinfect the blood pathways. The drain circuit 145 may optionally include a valve in one or both arterial or venous blood pathways. In an embodiment, an electronically controlled valve 206 in or near the modular drain circuit 145 in the venous line may permit the blood pumps on the blood pump cassette 13 to sequentially fill or clear the arterial line while the valve 206 in the venous line is closed, and then fill or clear the venous line upon opening of the valve. In this method, any air or contaminants in the arterial line are forced to the drain outlet of the drain circuit 145, rather than into the venous tubing. Alternately, the valve 206 may be arranged to control flow between the arterial line and the drain, e.g., so contents in the venous line can be forced to the drain outlet rather than into the arterial line. The drain circuit 145 may also optionally include conductivity and/or temperature sensors 148. A temperature sensor may be used, for example to monitor the temperature of the fluid circulating through the blood lines during heat disinfection. Conductivity sensors may be used to monitor the conductivity of water or dialysate solution being circulated through the blood lines during tests of the urea or sodium clearance of a dialyzer, for example. An electronically controlled BTS drain valve 207 may be placed either at the drain outlet of drain circuit 145, or it may be positioned external to the drain circuit 145. The BTS Drain valve 207 may be useful, for example, when heated water or chemical disinfectant is being circulated within the blood circuit components of dialysis unit 51.

Figure 28:
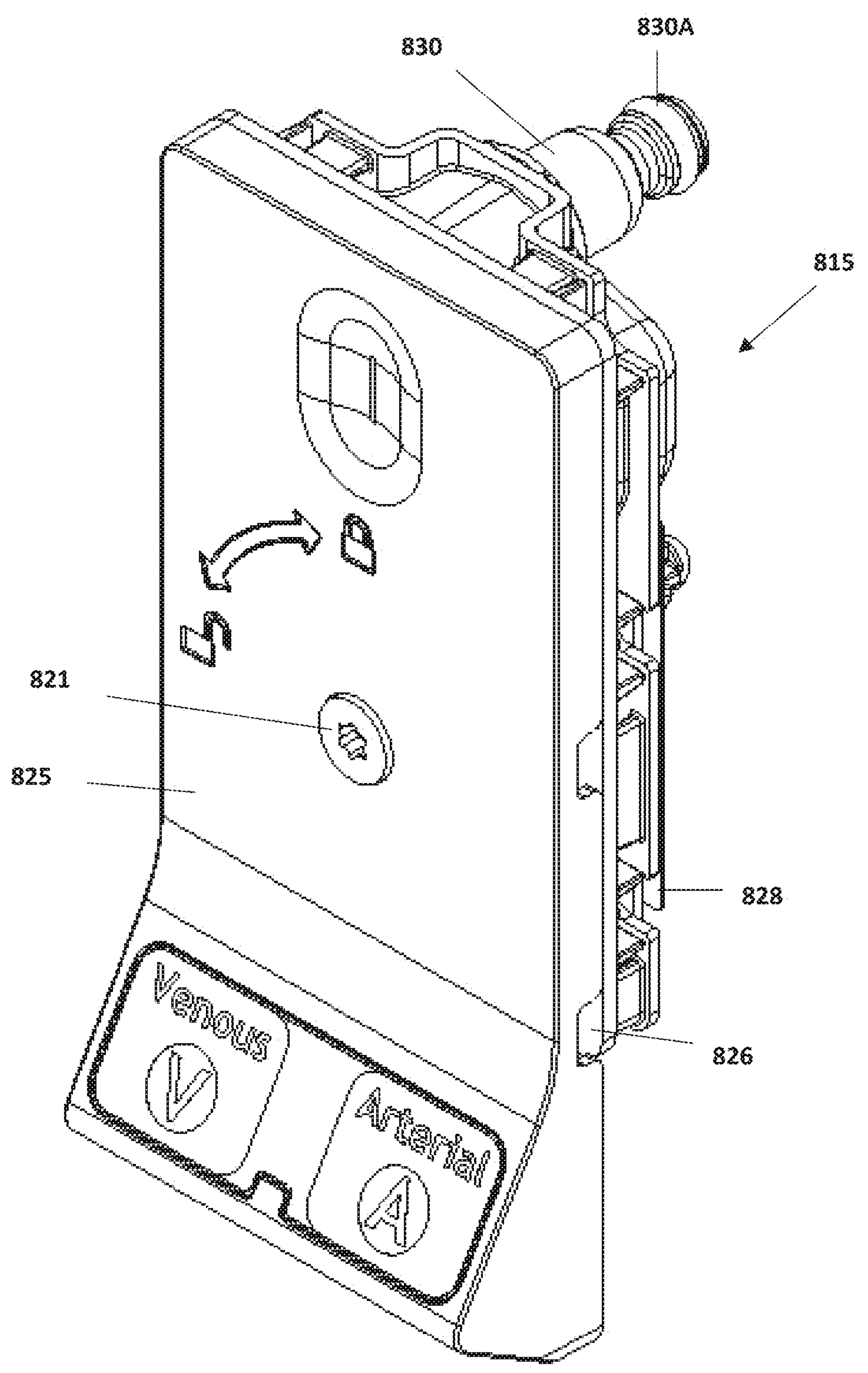
FIG. 28 shows a perspective view of the drain cassette in an illustrative embodiment.
Figure 29:
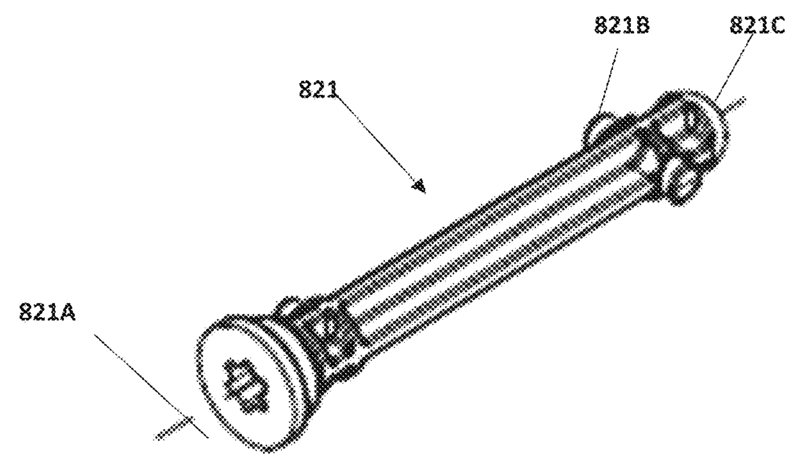
FIG. 29 is a perspective view of the attachment fastener for the drain cassette of FIG. 28.

FIG. 28 shows an exemplary modular drain cassette 815. In this view, the drain cassette cover 825 of the drain cassette 815 includes markings identifying the arterial and venous line connection points 814. A mechanical fastener 821 on the face of the drain cassette cover 825 may be turned with a tool to engage or disengage the drain cassette 815 from the front panel 511. Referring now to FIG. 29, the fastener 821 comprises a fitting 821A to receive a tool at the proximal end and two posts 821B at the distal end that is configured for a quarter turn closure. The distal end of fastener 821 includes a rounded end 821C to center the faster in the receive part. Requiring a tool to turn fastener 821 reduces the chance that the drain cassette will be removed and tampered with a non-qualified person.

Figure 30:
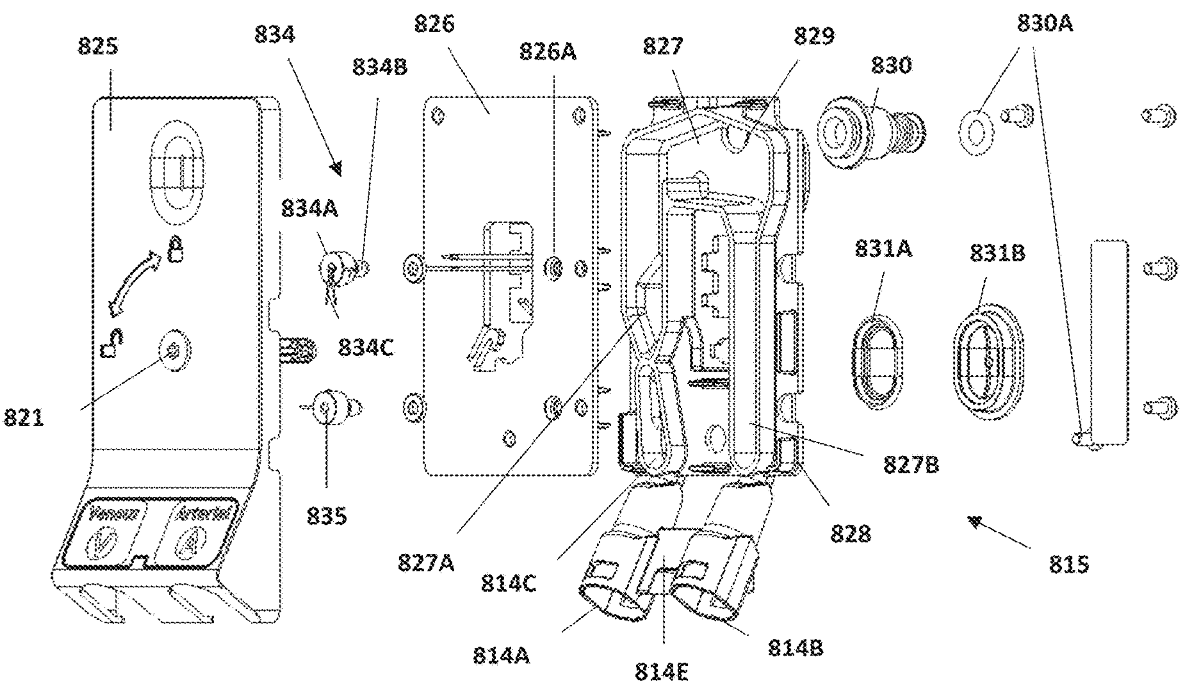
FIG. 30 shows the drain cassette of FIG. 28 in an exploded view with an escutcheon positioned anterior to a front wall of the drain cassette in an illustrative embodiment.

FIG. 30 shows the drain cassette 815 in an exploded view, with drain cassette cover 825 anterior to the front wall 826 of the drain cassette 815. The arterial blood line and venous blood line may be connected to the drain cassette 815 via connection points 814A, 814B of the drain cassette 815. The drain cassette 815 may include a chamber 827 which merges fluid flow from the venous and arterial blood lines, exiting via a common outlet 830 to a drain line 31.

The front wall 826 sealingly forms a front wall for the channel 827A, 827B and chamber 827 of the housing 828 of drain cassette 815. A common outlet 829 to a drain line from the channel 827 is equipped with a common outlet 830 mounted on the back wall of housing 828, which optionally may include a one-way check valve (e.g., such as a duckbill valve) to prevent fluid within the drain line from re-entering the channel 827. A mating connector 620 (FIG. 12B) is mounted on front panel 511, and is connected to a fluid line ultimately leading to drain. Outlet 829 is preferably positioned higher than either fluid connection points 814*a* and 814*b*, in order to trap and ultimately expel to drain any air that may be present in the arterial or venous blood lines when connected to drain cassette 815. In this regard, the fluid channel 827 may have a U shape, with the venous and arterial blood line connectors 802 fluidly coupling with a respective connection port 814*a*, 814*b* at ends of the U shape, and the drain outlet port 829 located at the bend of the U shape.

Continuing to refer to FIG. 30 valve 831 may be present on one or both fluid channel portions of channel 827A, 827B leading from connection points 814A and 814B. Thus, the valve may controllably open and close fluid communication in the channel 827 between the connection ports 814 and the drain outlet port 829. In embodiments where only one valve 831 is provided in the channel 827, flow between one connection port 814 and the outlet drain port 829 may be controlled by the valve while fluid communication between the other connection port 814 and the drain outlet port 829 may be permanently open. In the illustrated example, a pneumatically actuated membrane valve 831 mounted on the back of housing 828 is positioned over the portion of the channel 827A leading from venous blood line connection point 814A. A mating pneumatic connector 630 (FIG. 12B) mounted on the front panel 511 supplies valve 831 with positive or negative pneumatic pressure to actuate the valve. A pneumatic pressure line extending to front panel 511 from a pneumatic pressure distribution module or manifold located in a rear portion of dialysis unit 51. Both connector 830 and the pneumatic connector for valve 831 may be constructed to form radial sealing engagements (e.g., using elastomeric O-rings) with mating connectors on the drain recess 600 in order to allow for drain cassette 815 to be plugged into or unplugged from front panel 511 with relative ease.

Continuing to refer to FIG. 30, an electrical connector (not shown) mounted in the back wall of housing 828 to make electrical connections outside of channel 827 with temperature and/or conductivity probes positioned within channel 827. The electrical connector on the drain cassette may be constructed to form a keyed connection with a mating electrical connector 610 on the drain recess 600 (FIG. 12B) on front panel 511 in order to facilitate engagement and disengagement of the connector when drain cassette 815 is installed or removed from front panel 511. In some embodiments, the connections of the outlet drain port connector 830, the valve control port connector 831 and the electrical connector to respective connectors on the panel 511 may be made essentially simultaneously and/or in a single operation, e.g., by pushing the drain cassette 815 into place on the panel 511.

Figures 31A, 31B:
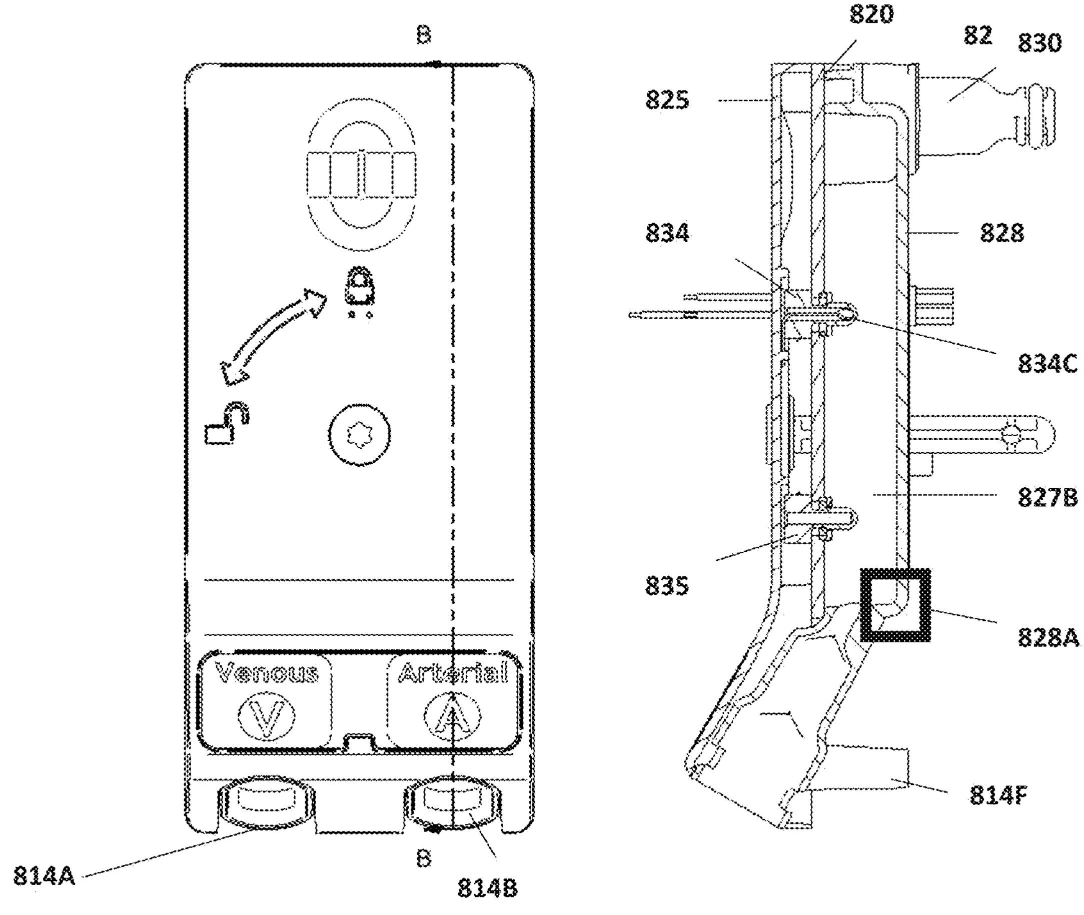
FIG. 31A show a front view of the drain cassette.
FIG. 31B shows a cross-sectional view of the drain cassette.

Referring now to FIG. 31A-B, the thermal and/or conductivity probes 834 and 835 are shown to illustrate their positioning in a portion 827*b* of fluid flow channel 827. Each probe, although sealingly installed on front wall 826, has an element that penetrates through front wall 826 to be in contact with the fluid channel 827B. The probes 834, 835 comprise conductive exterior surfaces that are exposed to the liquid in the flow path 827B. The conductive exteriors of the sensor are each electrically connected to an electrical connector (not shown) that connects to the controller electrical receptacle 610 (FIG. 12B) in the drain recess 610 on the front panel 511. One or both of the probes 834, 835 comprise a temperature sensor such as a thermistor, RTD, thermocouple or similar sensor that is located within the sensor 834, 835 and thermally connected to the exterior of the sensor that is in turn exposed to the liquid in the channel 827B. In one example, the probes 834, 835 comprise stainless steel cylinders 834A with an axial hole that extends part way through the cylinder from the back. In this example, a thermistor 834C is glued to the end of the hole in the cylinder 834B. The back end of the probes 834A, 835 are connected by one wire each to the electrical plug. The probes 834, 835 are sealed to the front wall 826 by O-rings or a compliant gasket captured between the back portion of sensors 834A and the gland 826A formed in front wall 826. The controller determines the conductivity of the liquid in channel 827B based on measured current, temperature and know distance between the two probes 834,835.

Referring now to FIG. 2, draining and flushing the blood circuit 141 to the drain circuit 145 results in biological fluids containing fibrous and or viscous elements to flow through the drain circuit 145. These waste fluids may deposit fibrous, viscous and or solid material on obstructions or protrusions into the flow. These obstructions could include the raised lip of a volcano valve port 126 (FIG. 11B) or a sensor probe that extends into the flow channel.

Figure 32:
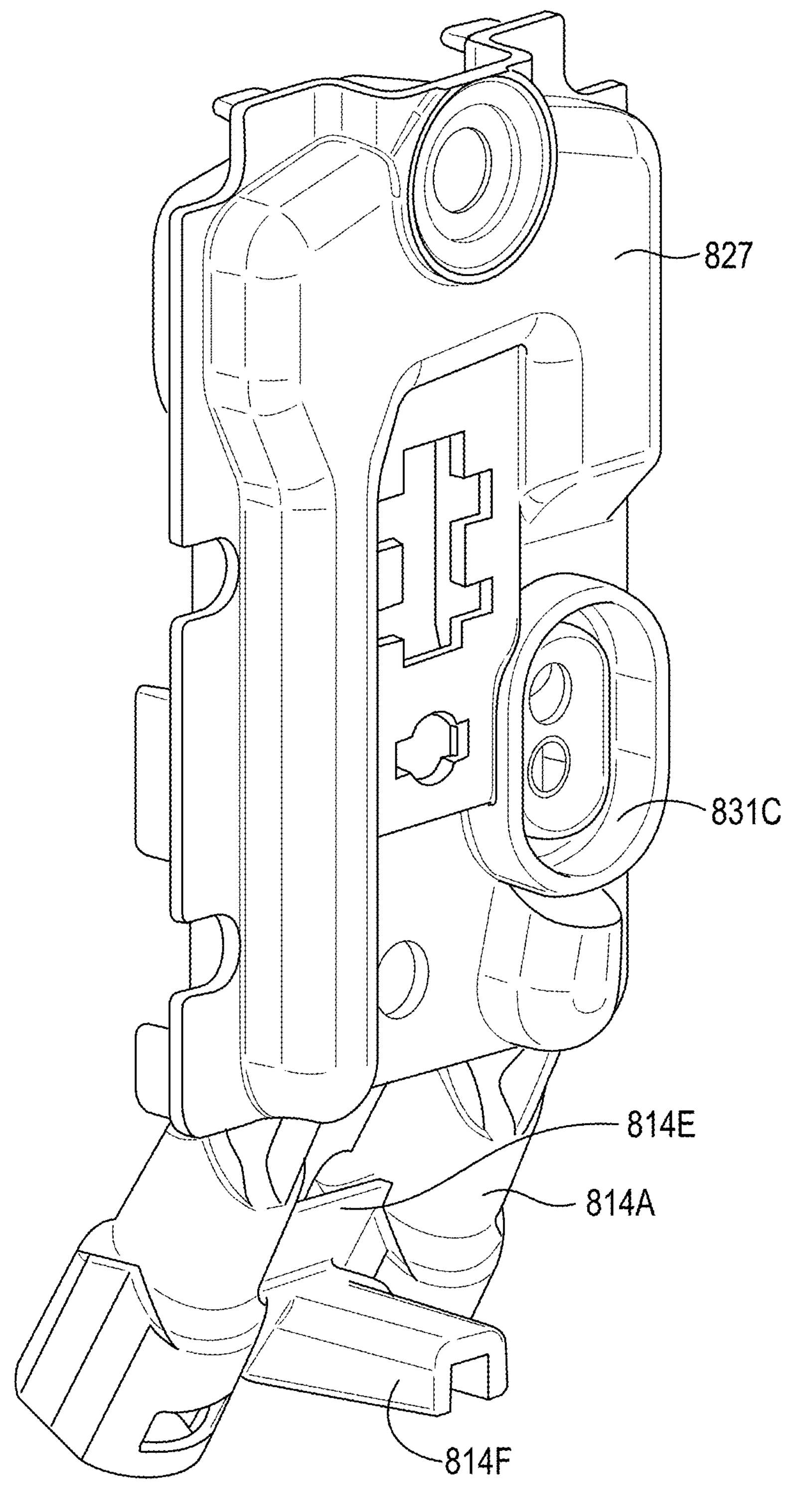
FIG. 32 shows a rear perspective view of the drain cassette of FIG. 28 in an illustrative embodiment.

Referring again to FIG. 3, an embodiment that minimizes the deposition of biological material within the fluid circuits, the disposable cassettes are provided with a low obstruction path for fluids flushed or drained from the blood circuit 141. The low obstruction design may include using only smooth valves between the dialyzer 14 and the drain 31 in the blood circuit 141 and drain circuit 145. In an embodiment, the valves 122 in the blood pump cassette 824 are also smooth and without volcano valve ports as seen in FIG. 8B. In an embodiment, the valves 206 and 207 between the blood circuit 141 and the drain 31 are smooth valves with matching valve diaphragms FIG. 9A. Referring now to FIGS. 31A, 31B, the sensor probes 834, 835 are shorter than sensor probes 1826 (FIG. 60) in the sensor cassette and protrude less than half way into the main flow of channel 827B as shown in FIG. 31B Referring now to FIG. 13B, the connection ports 814 receive the blood connectors 400 at the end of the patient blood lines 901, 902 before and after a therapy is executed. The act of inserting the blood connectors 400 into the connection ports 814 applies an upward force and a backward force on the connectors. The backward force is directed toward the drain recess 600 (FIG. 12B). Referring now to FIGS. 31B, 32, the backward force may cause the connection ports 814 to bend and rotate with respect to the lower edge 828A of the flat section of the drain cover 828. The repeated bending may lead to a shortened life of the drain cassette 815.

Continuing to refer to FIG. 32, the ports 814 are made more rigid by joining the two port 814A, 814B to each other with a drain flange 814E in this example. The drain flange 814E may be a flat plate located between the two connectors 814 and is approximately aligned with the center lines of the two connectors 814. The connectors are further made robots by rigidly attaching a drain post 814F to the drain flange 814E. The drain post 814F extends from the drain flange 814E in a plane that is parallel to the axis of the two connectors 814. In an example, the drain post 814F is centered between the two connectors 814. In an example, the drain post 814 is perpendicular to drain cassette cover 825 and or the back surface of the drain recess 600. The drain post 814F is configured to contact the surface of the drain recess 600, when the drain cassette 815 is installed in the recess. In an example, the drain post 814 contacts back wall of the drain recess 600 as the mounting screw 821 is threaded into the threaded hole 615 of the drain recess 600. The drain post transfers the backward force to the back wall of the drain recess 600, thereby reducing the bending and rotation of the connection ports 814 about the bottom edge 828A. In one example, the drain post 814F has a "U" shaped cross-section to increase the stiffness of the post, reduce the weight and avoid a thick section that are difficult to mold.

Conductivity Measurements and Automatic Disconnect Sensor

Figure 33:
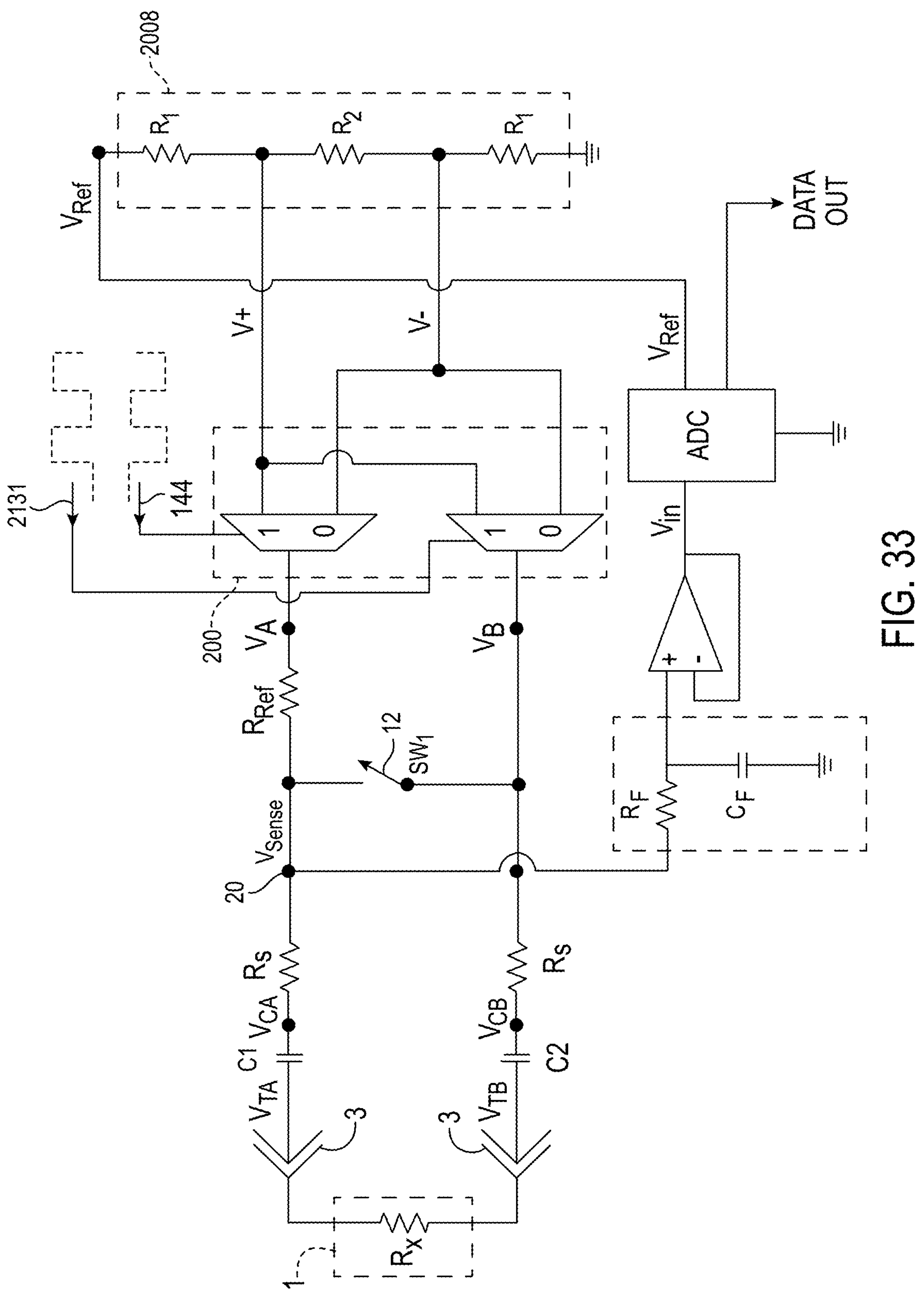
FIG. 33 is a schematic representation of a conductivity circuit in an illustrative embodiment.

An exemplary electrical circuit shown in FIG. 33 can be used to measure the electrical conductivity or resistance of a subject fluid. In one embodiment, the fluid may be an electrolyte solution or dialysate fluid, and the circuit may ultimately provide a measurement of the conductivity of the fluid to ensure its compatibility for intravascular administration. In addition to monitoring the concentration of dissolved solutes in the fluid, the electrical circuit can also monitor for any interruption in the continuity of the fluid between the electrodes connected to the circuit. For example, it can be used to monitor an intravenous fluid line for the presence of air bubbles, or for the presence of a contaminating substance. In another embodiment, the fluid may be blood, and a change in the measured electrical resistance of a blood flow path (for example, in a conduit) may be used to indicate if a discontinuity occurs between the blood flow path and measuring electrodes.

The circuit shown in FIG. 33 may be used to measure an unknown resistance Rx of a subject media 1 using inexpensive electronic components, particularly where the unknown resistance involves a conductive path through an electrolytic fluid. A switching network 2 comprising a pair of multiplexers allows the connection of nodes VA and to reference voltages V+ and V−. The subject media 1 having unknown resistance Rx is connected to terminals VTA and VTB 3, and forms a voltage divider with reference resistor Rref 4. To make a conductivity measurement, alternating voltages can be presented to the subject media 1 via switching network 2 to the voltage divider created by the known reference resistor Rref (680 ohms, for example, in the case of dialysate fluid) a 8nd the unknown resistance Rx of the subject media 1. The midpoint of the voltage divider is measured. The signal Vsense at point 8 is buffered by amplifier 10 to make the input signal Vin of the analog-to-digital converter (ADC). Vsense switches between two values as the voltage divider is driven first one way and then the other way. This signal is valid only for a short period of time after switching because the fluid in the conductivity cell 1 is AC coupled into the circuit through capacitors C1 and C2. Thus DC-blocking capacitors C1 and C2 may be used to prevent DC currents from passing through the unknown resistance (which may include a conductive path through electrolytic fluid or blood). In an embodiment, series capacitors C can each comprise two capacitors in parallel, one having a value, e.g., of 0.1 uF, and the other having a value, e.g., of 10 uF. Series resistors Rs may be used to reduce exposure by the switch network and other sense circuitry to noise and surge voltages. ADC can take multiple samples of the signal as the circuit is switched between the two configurations.

Figure 34:
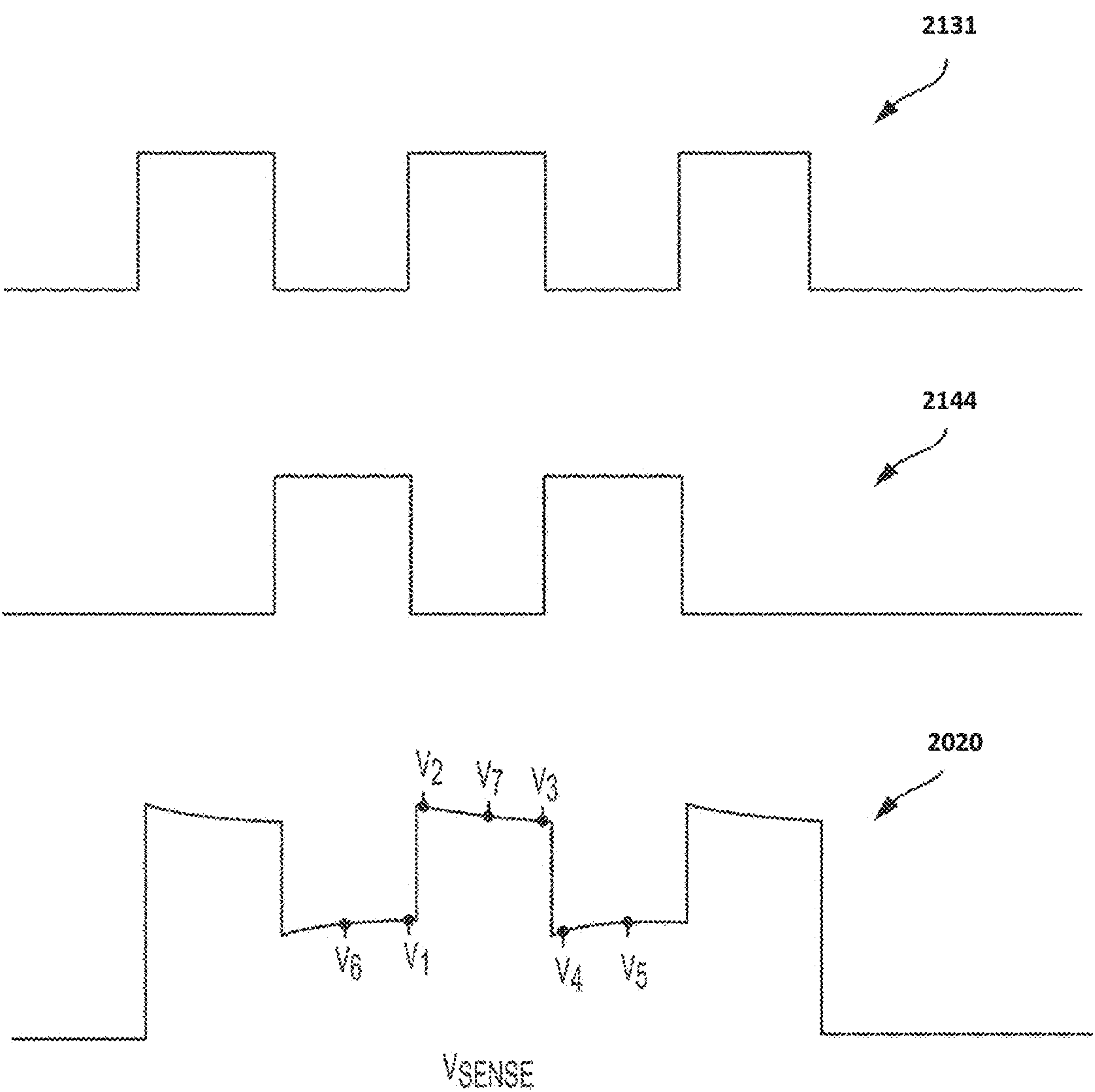
FIG. 34 is a diagram of the electrical waveforms processed by the circuit of FIG. 33.

The switching network 2002 can be driven by a pair of alternating binary control signals 2131, 2144 that connect VA to V+ and VB to V− during one half-cycle, and VB to V+ and VA to V− during the other half-cycle. The binary control signals 2131, 144 may be characterized by the duration of the cycle (T) or the frequency of the signal (f=1/T), The binary control signals 2131, 2144 may be further characterized by an active period in which the signals are alternating as shown in FIG. 34 between high and low values and an inactive period in which both signals are off. In one embodiment, the active period consists of a first control signals supplying three high half-cycles, while the second control signal supplies two high half-cycles. Applying the binary control signals 2131, 2141, to a circuit similar to the circuit in FIG. 33 produces a waveform at the Vsense node 2058 that is similar to the waveform 2020 shown in FIG. 34. In other embodiments, the number of high half-cycles for each control signal 2131, 2144 during the active period may be any integer number of high half-cycles for signal 2131 alternating with any integer of high half-cycles for signal 2144. Alternatively, during the active period the control signal 2131 may produce one high half-cycle alternated with one high half-cycle in control signal 2144.

In this embodiment, Vref is 4 volts, resulting in a Vsense amplitude of less than 4 volts, as shown in FIG. 34. A voltage divider 2008 creates the voltages V+ and V− that are near the positive reference voltage Vref and near ground, respectively. In one embodiment, R1 can have a value of ten ohms, and R2 can have a value of 2K ohms. When both multiplexers of switching network 2002 are commanded to zero, the circuit is at rest and the lower voltage is presented to terminals VTA and VTB 3. When VA is high and VB is low, the higher voltage is presented to the reference resistor Rref and the lower voltage is presented to the subject media 1 having unknown resistance Rx. When VB is high and VA is low, the higher voltage is presented to the subject media 1 having unknown resistance Rx and the lower voltage is presented to the reference resistor Rref.

Vascular Disconnect Detector

With the appropriate modifications of a conductivity measurement circuit such as the one described above, it is possible to detect the conductivity and changes in the conductivity of blood. More specifically, it is possible to detect the change that occurs in the conductivity of a volume of blood when air enters the volume. This situation can occur, for example, when an intravascular access site becomes dislodged in an extracorporeal blood circuit.

The circuit shown in FIG. 33 can be used to measure the resistance of a volume of fluid in a conductivity cell or conduit 1. For measurements of Rx of a conductivity cell 1 representing the resistance or conductivity of a volume of dialysate solution, a convenient value for the reference resistor Rref 4 can be chosen to be approximately 680 ohms. For measurements of Rx of a conduit 1 representing the resistance or conductivity of a column of blood extending from a first cannula or needle, through an arterio-venous fistula, to a second cannula or needle, a convenient value for the reference resistor Rref 4 can be chosen to be approximately 200 k ohms.

With the lower reference resistor Rref 4 value (e.g. 680 ohms), this circuit is appropriately configured for dialysate conductivity measurements. With a much higher reference resistor Rref 4 value (e.g. 200 k ohms) this circuit is appropriately configured for measuring the resistance between an arterial needle and a venous needle to detect vascular needle dislodgement from an arterio-venous fistula.

Electrode Placement

The continuity of a fluid column leading from a fluid delivery apparatus to a patient's blood vessel or vascular graft can be monitored using the electronic circuit described above. The fluid being delivered may include blood or any electrolyte solution, including dialysate fluid. Although the following discussion will involve a hemodialysis system, the same principles of operation of the invention can apply to any device that is configured to deliver a fluid to a patient via a vascular access. In an embodiment illustrated by FIG. 35, the conductivity of a volume of blood or other fluid within a fluid flow circuit 100 of a hemodialysis machine 200 can be monitored electronically, using electrodes on each end of the volume that make direct contact with the blood or other fluid. Using an electrical circuit such as the one shown in FIG. 33, one electrode can be connected to the VTA terminal, and the other electrode can be connected to the VTB terminal of the circuit. The voltages applied to the electrodes by the circuit can be sufficiently small (e.g., about 4 volts or less), sufficiently brief, and with DC voltages sufficiently decoupled so as to prevent any harm to the patient. In this example, a fluid flow circuit 3100 is shown, including an arterial access needle 3102, an arterial catheter tubing 3104, an arterial catheter tubing connector 400, arterial blood circuit tubing 902, and hemodialysis machine 51, a blood pump 13, a dialyzer 14, a dialyzer outlet line 120, air trap 19, and venous blood circuit tubing 901, a venous catheter tubing connector 400, a venous catheter tubing 3130, a venous access needle 3132, and the intraluminal volume of that portion of the patient's blood vessel or fistula 3134 that lies between the arterial access needle 3102, and the venous access needle 3132. It should be noted that the invention described herein also encompasses circumstances in which the arterial access needle may reside in one blood vessel of a patient, while the venous access needle may reside in a separate blood vessel some distance away from the arterial access site. Furthermore, the circuit described above may be used to monitor the integrity of a vascular access in a fluid delivery system that does not have the venous return line shown in FIG. 35. In that case, for example, an electrode at location B could be paired with an electrode in contact with fluid in a dead-end line communicating with a second needle or cannula accessing the blood vessel or vascular graft. In another example, an indwelling hollow cannula or solid trocar in the vascular segment can be equipped with a conductive wire which could then serve as the second electrode in the monitoring system. The vascular segment being accessed may be a surgically constructed arterio-venous fistula, and may also include an artificial conduit such as a GoreTex® vascular graft. The term 'arterial' is used herein to denote the portion of the blood flow circuit that conducts blood away from the patient and toward the hemodialysis machine 200. The term 'venous' is used to denote the portion of the blood flow circuit that conducts blood away from the hemodialysis machine 200 and back toward the patient. The term 'access needle' is used to denote a needle or catheter device that penetrates the patient's vascular segment or fistula. In different embodiments it may be permanently fused or reversibly connected to a corresponding catheter tubing 104, 130.

The continuity of any segment of the fluid flow circuit 3100 can be monitored by positioning two electrodes in contact with the fluid on either side of the fluid and blood-containing segment of interest. In order to monitor for a disconnection of the arterial access needle 3102, or the arterial catheter tubing 3104, or the venous access needle 3132 or venous catheter tubing 3130, one electrode can be placed in continuity with the lumen of the venous side of the blood flow circuit, while a second electrode is placed in continuity with the lumen of the arterial side of the blood flow circuit. In a preferred embodiment, both electrodes can be positioned to be nearer to the patient's blood vessel or vascular graft than the equipment associated with the dialysis machine 51. This may further reduce electrical interference associated with the dialysis machine 51. An electrode A can be conveniently placed at or near the arterial catheter tubing connector 106 and a second electrode B can be conveniently placed at or near the venous catheter tubing connector 128. In some cases, the access catheters 3104 and 3130 can be as short as about a foot, whereas the arterial and venous tubings 902 and 901 can be about six feet long.

Connector Electrodes

Figure 37B:
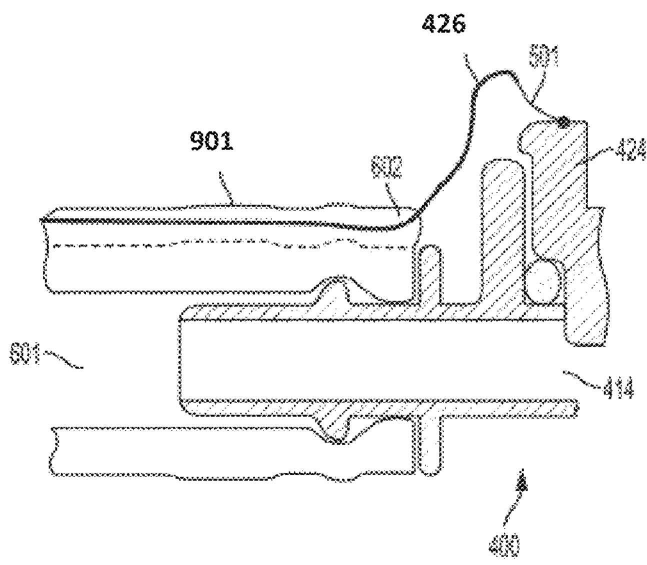
FIG. 37B is a cross-sectional view of a connector similar to the connector of FIGS. 36C, with an attached wire and tubing similar to the double-lumen tube of FIG. 37A.
Figure 37A:
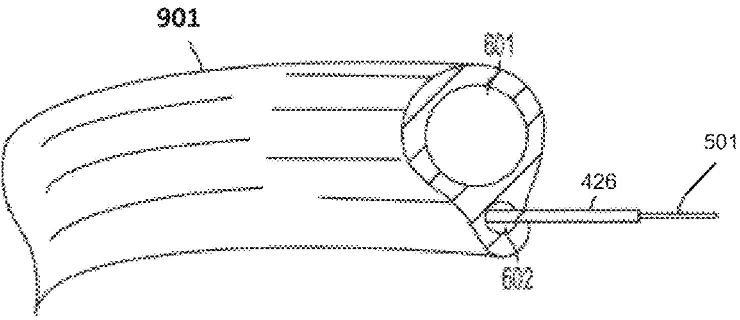
FIG. 37A is a perspective view of a flexible double-lumen tube having a fluid-carrying lumen and a wire-carrying lumen.

Referring now to FIGS. 37A-37C, a blood line connector 400 for the blood circuit of a hemodialysis system may incorporate electrodes that can make contact with any liquid within the lumen of the connector. The electrode is preferably constructed from a durable and non-corrosive material, such as, for example, stainless steel. The distal coupling end 404 of connector 400 can be constructed to make a sealing engagement with a corresponding Luer-type connector of an arterial or venous catheter, for example. An O-ring 416 or a suitable sealant can be placed between the cap electrode 410 and the proximal end 402 of the connector to maintain a fluid-tight connection between the connector and any flexible tubing attached to the connector.

An elastomeric O-ring may be particularly useful in hemodialysis or other extracorporeal systems in which the blood-carrying components are subjected to disinfection or sterilization using heated liquids. The thermal coefficients of expansion of the plastic components of a connector may be sufficiently different from that of an incorporated metal electrode that a permanent seal may not be preserved after one or more sterilization or disinfection procedures. Adding an elastomeric component such as an O-ring at the junction between an electrode and the connector seat on which it is positioned may preserve the seal by accommodating the different rates of expansion and contraction between the electrode and the connector.

Continuing to refer to FIGS. 37A-37C, a connector 400 as described in U.S. Patent Application Publication No. 2010/0056975 (the contents of which are hereby incorporated by reference) has been modified so that a mid-portion 406 of the connector 400 can incorporate an electrode. Placement of the electrode along the mid-portion 406 of the connector 400 avoids having to alter the distal coupling end 404 of the connector, and avoids any alteration of the interaction between the termination of the flexible tubing and the proximal end 402 of the connector. In this example, the blood line connector 400 is constructed to make two different types of sealing connections on its distal coupling end 404, including an internal screw-type connection 405 for a Luer-type connector of a patient access line, and an external press-in type connection 407 with a dialysis machine port for recirculation of priming and disinfecting fluid through the blood carrying components of a dialysis system. The press-in feature 407 is formed having a frustoconical shape on the outside surface of the distal end 404 of the connector 400, while the Luer-compatible screw-type feature 405 is formed on the corresponding internal surface of the distal end 404 of the connector 400. The outside surface of the frustoconical member is constructed to make sealing engagement with the seat of a mating connector of a dialysis machine 200 or other device. A pair of locking arms 408 extending proximally from the distal coupling end 404 of the connector 400 can each have a barbed portion 409 to engage a corresponding locking feature on a mating connector on the dialysis machine, and a finger depression portion 410 to aid in disengaging the barbed portions 409 from the dialysis machine. The barbed portion 409 helps to lock the frustoconical member in sealing engagement with its mating connector on the dialysis machine when making a press-in type of connection. The distal ends of the locking arms can be constructed to attach to the connector via a flange 411 located proximal to the frustoconical portion 407 of the connector 400. The connector 400 has a proximal tubing attachment end 402 to sealingly engage a flexible tube. The tubing attachment end 402 may have one or more barb features 412 to help prevent disengagement of the end of a flexible tube from the connector 400.

FIG. 37B shows a side view of connector 400, bringing into view an access feature or port 420 that can permit placement of an electrode in direct communication with the lumen of connector 400. In other embodiments, the access feature may house an elastomeric stopper—with or without a septum—to permit sampling of fluid from within the lumen 414 of connector 400 using a syringe with a sharp or blunt needle. Alternatively, the feature may serve as a port to allow connection of another fluid line to the lumen 414 of connector 400.

In yet another embodiment, the mid-portion 406 of connector 400 may have two access ports, as shown in the cross-sectional view of FIG. 37C. A fluid access port 420*a* can serve as a sampling port, and an electrode port 420*b* can serve as an electrode cradle. An elastomeric stopper 422 within sampling port 420*a* can be shaped to extend to the lumen 414 of connector 400, simultaneously permitting sampling of fluid in the lumen 414 with a needle, while maintaining an air-tight seal. Alternatively, a Luer-type connector having a septated cap or seal can be incorporated into the port, which is capable of connecting with a syringe or catheter having a mating Luer-type connector. An electrode port 420*b* can serve as a seat or cradle for an electrode 424. In can be press-fit or cemented into position, and sealed with an adhesive, or with an O-ring 416 as shown. A wire 426 can be soldered, welded or otherwise secured onto the outer surface of electrode 424, and can travel proximally toward dialysis machine 200 with the arterial tubing 108 or venous tubing 126 to which connector 400 is attached.

In any of the above electrode embodiments, the electrodes may be replaced by a suitably sized thermistor, or combination of a thermistor and electrical conductor, for the additional purpose of monitoring the temperature of the fluid passing through connector 300, 400 or variants thereof.

Wire Assembly

Figure 35:
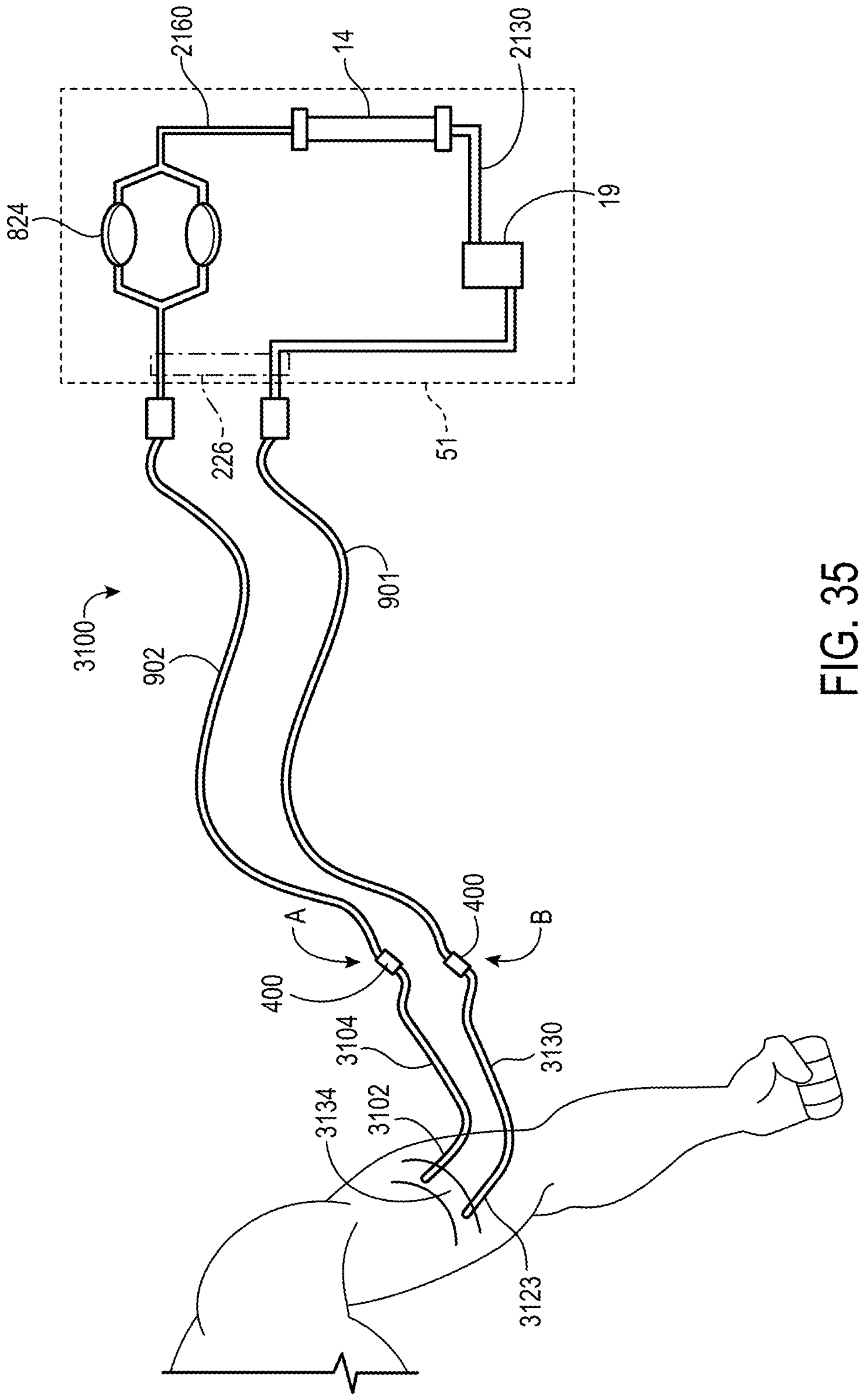
FIG. 35 is a schematic representation of an exemplary blood flow circuit of a hemodialysis system.
Figure 36A:
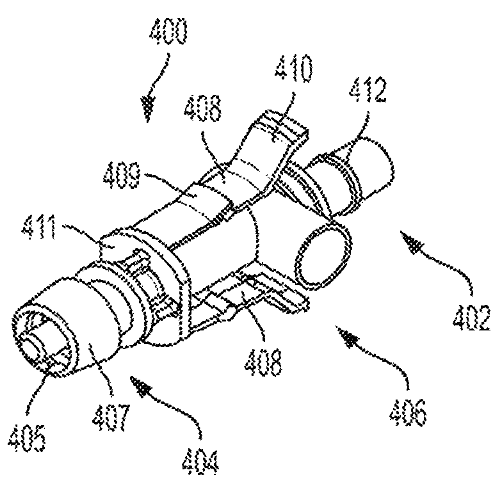
FIG. 36A is a perspective view of an alternate embodiment of a connector that may be used in the blood flow circuit of FIG. 35.
Figure 36B:
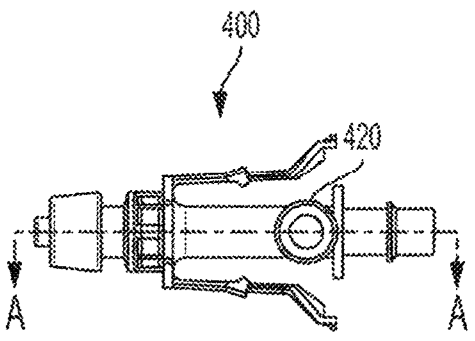
FIG. 36B is a top view of the connector of FIG. 35.
Figure 36C:
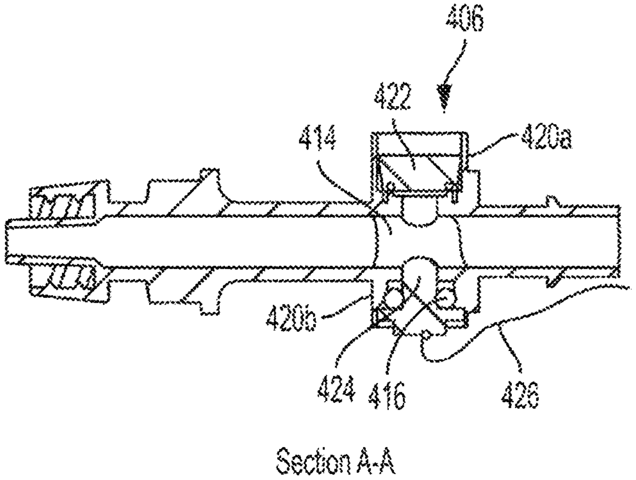
FIG. 36C is a cross-sectional view of the connector of FIG. 35.

Referring now to FIG. 35, in one embodiment, the wires carrying electrical signals to or from a pair of electrodes on connectors 400 (one on the arterial side and one on the venous side of the blood flow circuit) can travel separate and apart from the blood tubing 901, 902 back toward dialysis machine 51, where they ultimately terminate and connect to, a conductivity detecting circuit, such as the conductivity circuit shown in FIG. 33. The conductivity circuit, in turn, provides an appropriately configured signal to a processor on the dialysis machine to determine whether a change in fluid conductivity consistent with an access disconnection has occurred. If so, the processor can trigger an alarm condition, or can initiate a shut-down of blood pump 823, and trigger the occluder 513 to pinch closed the blood tubing 901, 902, for example.

Wires that extend together or separately between the dialysis machine and the patient are at risk of getting tangled, broken or becoming disconnected. Therefore, preferably, each wire 426 can be attached, fused, or otherwise incorporated into its associated tubing 901, 902. Incorporating a wire into its associated tubing provides a convenient way of protecting the wires and connections, and simplifying the interface between the patient and the dialysis apparatus.

Figure 38:
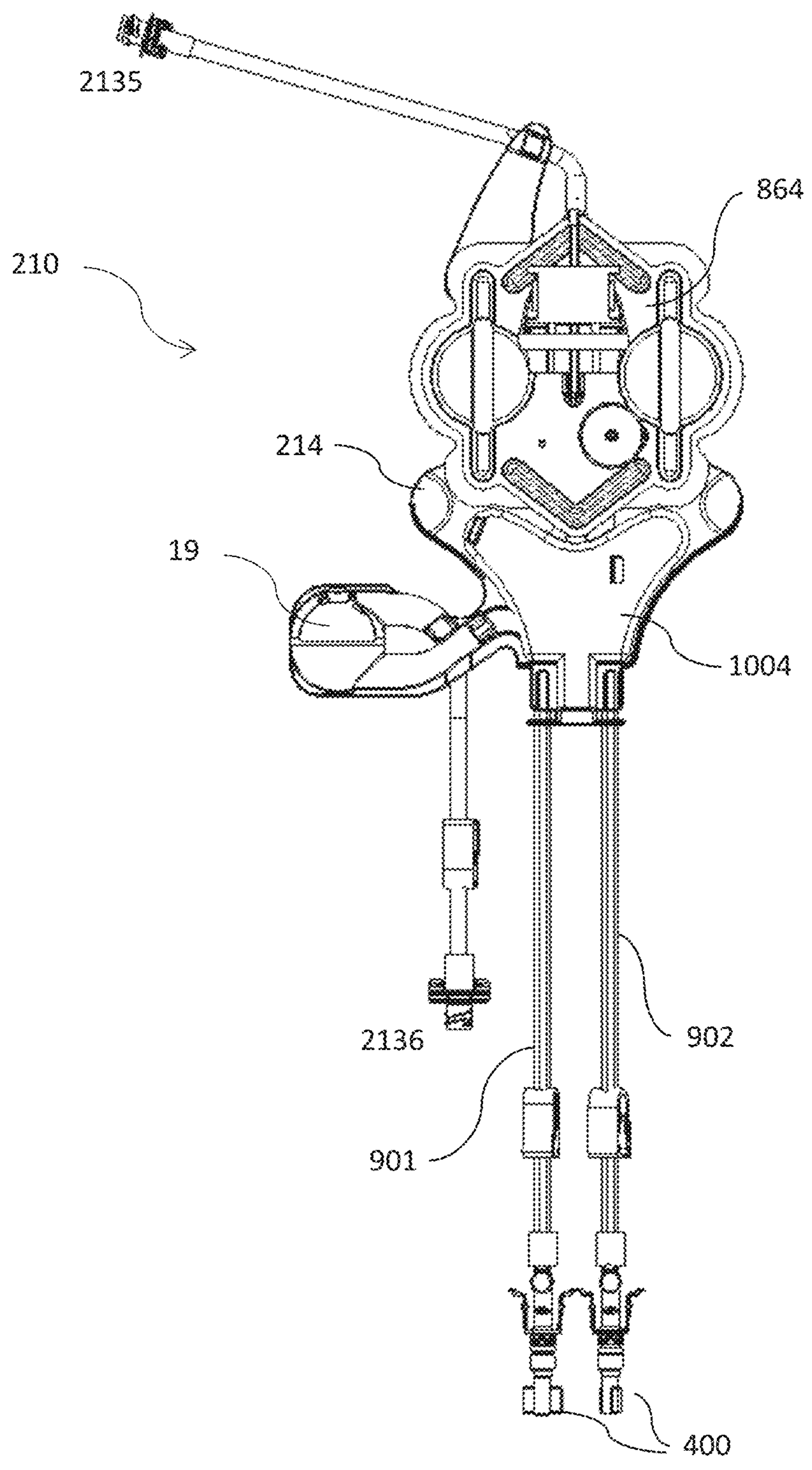
FIG. 38 is a front view of an exemplary blood pump to implement the extracorporeal blood flow circuit used in a representative hemodialysis system.

In a preferred embodiment, a co-extrusion process incorporating an insulated wire can generate a tube-wire bundle as shown in FIG. 37. In this example, flexible tubing 901 is a co-extrusion of a fluid-carrying lumen 601 and a wire-carrying lumen 602. Preferably, the wire 426 is multi-stranded for flexibility and durability. In another embodiment, the wire 426 is bare inside the wire-carrying lumen 602. FIG. 38 shows a cross-sectional view of an exemplary connector-wire-tubing assembly. The proximal tubing connection end of a connector 400 is shown with the end of a double-lumen tubing 901 attached. The fluid-carrying lumen 601 is press-fit and/or cemented to the proximal end of connector 400, allowing for fluid flow through the central lumen 414 of connector 400. Stranded wire 426 is soldered or otherwise attached to electrode 424, which is in conductive contact with any fluid present within the lumen 414 of connector 400. The non-connecting portion of the wire 426 that travels outside tubing 901 is preferably sheathed in an insulating synthetic coating, such as, for example, PTFE. Optionally, this portion of both the exposed and sheathed wire may also be sealed with a sealant, such as RTV. The wire 426 enters the wire-carrying lumen 602 of tubing 502 near its termination onto connector 400. The wire/tubing bundle then makes its way toward the dialysis machine 51, where the wire emerges from the tubing to make a connection to a conductivity circuit such as the one shown in FIG. 33.

Figure 39:
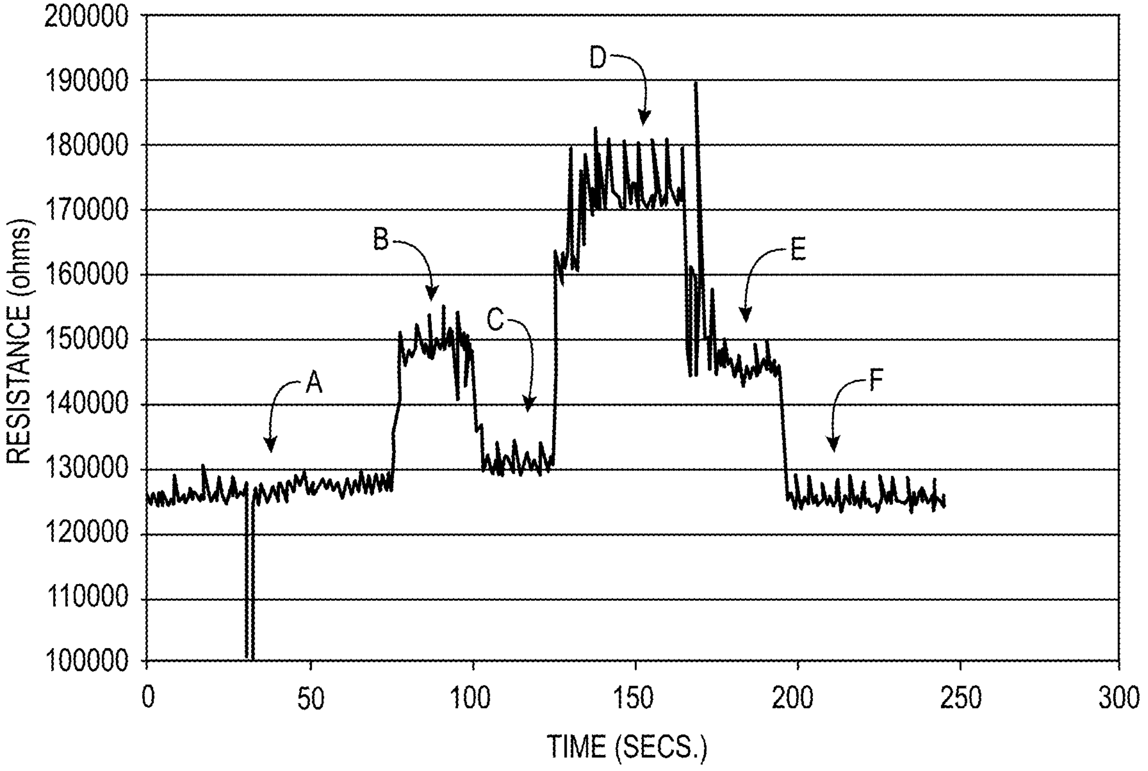
FIG. 39 is a representative plot of the resistance measured by the conductivity circuit of FIG. 33 under various conditions.

FIG. 39 shows an exemplary blood cassette assembly 865 that together with a dialyzer makes up the blood assembly 210. The blood assembly 210 that may be used as a removable, replaceable unit in a hemodialysis unit 51 as shown in FIG. 13A. In this embodiment, the extracorporeal circuit comprises a blood pump cassette 864, dialyzer connected to dialyzer connectors 2135, 2165, venous return air trap 19, arterial blood tubing 902, venous blood tubing 901, and the arterial and venous catheter connectors 400. The arterial and venous connectors may be of a type similar to the connector 400 shown in FIGS. 37A-37C, or variants thereof. The arterial 902 and venous 901 blood tubes may be of a type shown in FIGS. 37A-37C. Wires forming terminal connections to electrodes on connectors 400 may exit arterial 902 and venous 901 tubes to make a connection with a connector that ultimately passes the connection through on the dialysis apparatus to terminals associated with a conductivity circuit such as that shown in FIG. 33. The uninsulated wire segment between the connector and the blood tubes 901, 902 may be covered with a shield 1004 (FIG. 39) that connects to the bottom plate 1001. The placement of the wire 426 within the arterial and venous tubes 901, 902 and the relative location of the arterial tube 108 to the venous tube 126 can create a capacitive conductance between the wires 501 in each of the tubes 901, 902. This capacitive conductance may serve as an additional conductive path between the terminals VTA and VTB 3 (FIG. 33) and in parallel with the purely resistive impedance through the blood columns of the catheter tubes 3104, 3130 and the fistula 3134 (FIG. 35). The capacitive conductance between the wires 426 within the arterial and venous tubes 901, 902 will vary with the distance between the tubes. The Vsense measurement made with a circuit similar to FIG. 33 can be made insensitive to the position of the arterial and venous tubes 901,902 be selecting a frequency of the binary voltage signals 2131, 2144 (FIG. 34) low enough to saturate the capacitance between the wires 426 within the arterial and venous tubes 901,902. In an exemplary embodiment, the binary voltage signals are each operated at a 50% duty cycle at a frequency of about 2174 Hz during periodic active phases. The active phase may be set to occur every 80 milliseconds.

Operation of the Disconnect Detection Circuit

FIG. 40 shows test results utilizing the disconnect detection circuit described above and shown in FIG. 33. In this case, a hemodialysis blood circuit and apparatus was employed that is similar to that disclosed in U.S. Patent Application Publication Nos. 2009/01 14582 and 2010/0056975, (the contents of which are hereby incorporated by reference). The blood flow circuit tested included a pair of membrane-based blood pumps arranged on a blood pump cassette 864 shown in FIG. 35 a dialyzer 14, a venous return air trap 19, an arterial blood tubing set 902, a venous blood tubing set 901, arterial and venous connectors 400 and catheter tubing sets 3104, 3130 connected to vascular access needles 102, 132. The needles 102, 132 were placed in a container holding anticoagulated bovine blood. The blood tubing set 901, 902 was approximately six feet long, and the catheter tubing sets 3104 and 3130 were approximately two feet long or less. The needles were alternately manually placed in or withdrawn from the container during blood flow to simulate disconnection of a needle from a fistula or blood vessel. Periods A, C and F in FIG. 40 represent the times during which the needles were submerged in the blood in the container. The electrical resistance measured by the disconnect detection circuit shown in FIG. 33 during these periods averaged between 120,000 and 130,000 ohms. Periods B and E in FIG. 40 represent the times during which the venous return needle 132 (under positive pressure from the blood pumps) was withdrawn several centimeters above the surface of the blood within the container, forming a stream of blood mixed with air as the blood exited the venous return needle and entered the container of blood below. The electrical resistance measured during these periods averaged between 140,000 and 150,000 ohms. Period D represents the time during which one of the needles was completely removed from the container, creating a fully open electrical circuit. The electrical resistance measured during this period averaged between about 160,000 and 180,000 ohms. Thus a controller can be readily programmed to distinguish the difference in the monitored resistance of the electrical circuit between an uninterrupted and an interrupted flow of blood. These results showed that an interruption of the continuity of the blood between the arterial 102 and venous 132 needles can reliably produce a detectible change in the measured electrical resistance between two electrodes when placed relatively closer to the arterial and venous access sites than to the blood processing components 13, 14 and 122 of the extracorporeal blood circuit. Furthermore, even a partial interruption of the continuity of blood flow (as in the streaming of blood through air) can be reliably detected, albeit with a smaller change in the measured electrical resistance.

DTS Assembly

Figure 55:
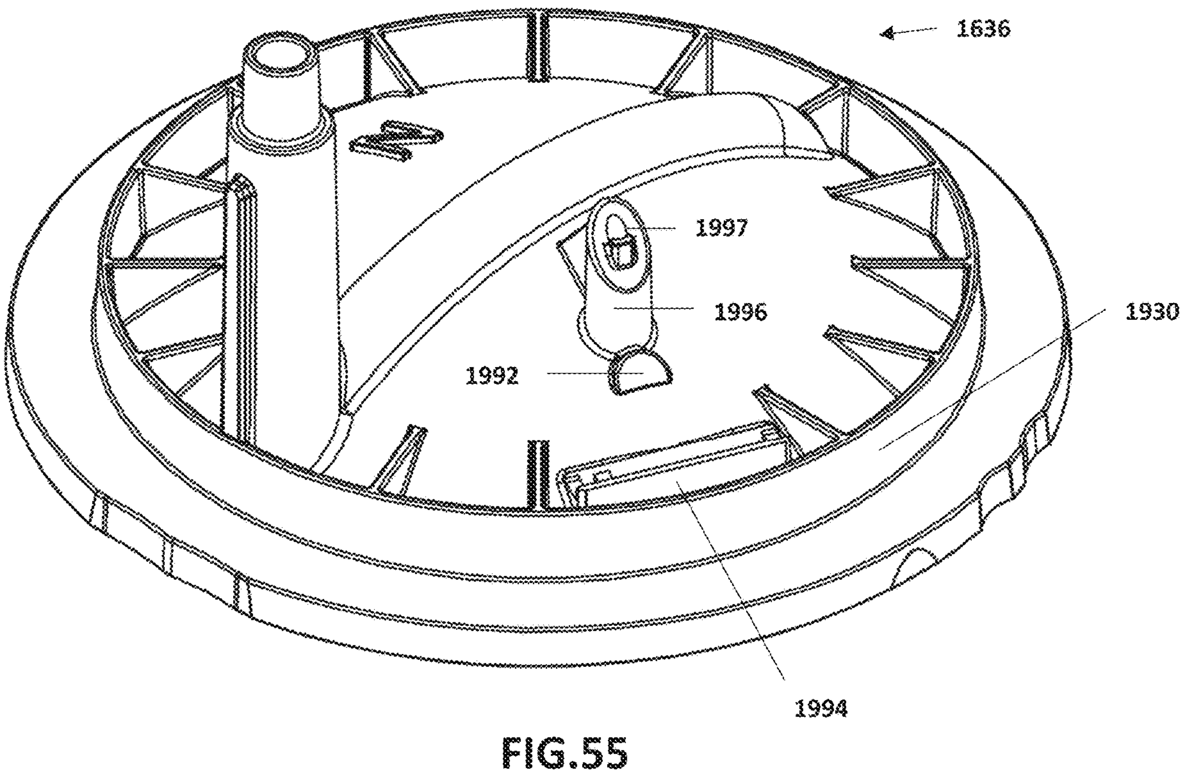
FIG. 55 is a perspective view of one of the domes of the balance pod.

Referring now to FIG. 55, the Integrated Cassette assembly 1626 may be used in connection with a hemodialysis system. The integrated cassette assembly 1626 is described below with respect to a hemodialysis system, i.e., a system including a cassette system that mixes dialysate, transports dialysate and balances the volume of dialysate before and after flowing through a dialyzer. The integrated cassette system may be used in conjunction with hemodialysis systems and methods, for example, similar to the hemodialysis systems and methods described in the U.S. patent application entitled Hemodialysis Systems and Methods (U.S. patent application Ser. No. 12/072,908), which is being filed on even date herewith and is hereby incorporated by reference in its entirety.

FIG. 55 shows an example of a cassette assembly 1626 with three cassettes 1628, 1630, 1632 are joined together by fluid-handling pods 1634, 1636. Cassette 1800 is a sensor cassette that is mounted to the mixing cassette 1632. The inter-cassette pods 1634, 1636 may include self-contained diaphragm pumps having both actuation and fluid conduits, or other liquid-carrying chambers 1636, having only fluid conduits. Examples of other types of liquid-carrying pods include fluid mixing chambers, or fluid balancing pods in which the flow through a first fluid line is balanced by the flow through a second fluid line through a pod having a first variable volume separated from a second variable volume by a flexible diaphragm. Each fluid-handling pod 1634, 1636 fluidly connects to either or both cassettes that flank it, either by flexible or rigid conduits. Rigid liquid conduits 1638 may be preferred, because they can provide structural support for the cassette assembly. In the case of a diaphragm pump pod 1634, both liquid-carrying and actuation conduits may extend to one or both cassettes flanking it. The conduits 1638 penetrate the face of the flanking cassette to reach a fluid or actuation channel located in the first or second inter-plate space of that cassette. Generally, actuation channels driving the inter-cassette pump pods will course without interruption from a cassette actuation port to the actuation chamber of the pump pod. Fluid channels of either an inter-cassette pump pod or another type of fluid-handling pod will connect to a corresponding inter-plate fluid channel in one or both flanking cassettes via one or more diaphragm valves located in the cassette. The actuation channels of these diaphragm valves, the actuation channels for the pump pods, and any other actuation channel in the cassettes travel within the first or second inter-plate space of each cassette to a first edge of the respective cassette to terminate into a cassette actuation port 1640. In the cassette assembly, each cassette 1628, 1630, 1632 has actuation ports 1640 located on a narrow side or edge of the respective cassettes, and are all configured to face in the same direction, so that the cassette assembly actuation ports occupy one side of the cassette assembly. This allows the cassette assembly 1626 to be plugged into or unplugged from one or more receptacle assemblies in a single motion.

An exemplary embodiments in FIG. 55 shows a first carrier frame 1705 and a second carrier frame 1707 that can engage with the cassette assembly 1626 from opposing directions. Some embodiments can provide similar carrier frames to secure the cassette assembly 1626 from adjacent sides. Other embodiments can also provide a monolithic carrier frame to secure the cassette from more than one pair of opposing sides.

Carrier frames 1705 and 1707 can further include plate rails that can slide over the corresponding cassette plates of cassettes 1628, 1630 and 1632 for engaging with the cassette assembly 1626. Connecting the frame components together, and securing the enclosed cassette plates in rails may eliminate the need for puncturing or drilling holes into any of the three cassette plates in order to secure them to the frames. The rails configuration and absence of screws, nuts or clips through the cassette plates can reduce the possibility of damaging the cassette assembly and interfering with any of the pneumatic connections or pathways therein. For example, first carrier plate 1705 can include a first set of plate rails 1705A, 1705B and 1705C and the second carrier plate 1707 can include a second set of the plate rails 1707A, 1707B and 1707C. Plate rails 1705A, 1705B, 1705C, 1707A, 1707B and 1707C can comprise elongated slots capable of partially or completely receiving at least one edge or a portion of the edge of corresponding cassette plates of cassettes 1628, 1630 and 1632. For example, with reference to first carrier frame 1705, the plate rails 1705A, 1705B and 1705C can receive edges of cassette plates of cassettes 1628, 1630 and 1632, respectively.

The integrated cassette assembly 1626 is a physical implementation of the dialysate flow circuits 25, 143 and 142 in FIG. 2. Each of the three cassettes 1628, 1630, 1632 implements a dialysate flow circuit. The dialysis cassettes comprise a plurality of pneumatic-diaphragm valves. Cassettes 1628 and 1630 include one or more pneumatic diaphragm pumps that are also referred to as metering pumps. The dialysis cassettes include a plurality of fluid channels that connect the various pumps, valves and external ports. Each dialysis cassette includes a plurality of pneumatic channels that fluid connect the actuation chambers of pumps or valves the actuation ports 1640 on one edge of each cassette. The integrated cassette assembly 1626 comprises a plurality of pump pods 1634 and balance pods 1636 and one mixing pod that are located between pairs of cassettes and mounted in surface ports on the plate of the cassettes facing the pods.

The mixing cassette 1632 in FIG. 55 is a physical implementation of the mixing circuit 25 in FIG. 7 minus the dialysate ingredients 49 and sensor 178, 179. The mixing cassette 1632 is fluidly connected to the dialysate ingredients 49 and the sensors 178, 179 of the mixing circuit (FIG. 7) via flexible tubes. The mixing cassette 1632 comprises the two metering pumps 183, 184 of the mixing circuit (FIG. 7) that pumps bicarbonate and acid into the water drawn from the inlet line 30A. The mixing cassette 1632 includes the four pneumatic diaphragm valves 270, 271, 274, 275 that control flow to and from the pod pumps 280, 282 of the mixing circuit (FIG. 7). The mixing cassette 1632 includes the pneumatic diaphragm valves 272, 273, 277, 278 that control flow through the metering pumps 183, 184 of the mixing circuit (FIG. 7).

The pneumatic diaphragm valves in the mixing cassette 1632 are presented above in FIGS. 8A, 8B, where the diaphragm closes the ports 85 when pneumatic is applied to the actuation chamber 98. The large pod pumps 280, 282 and the mixing pod 189 of the mixing circuit (FIG. 7) are located between the mixing cassette 1632 and the directing cassette 1630.

The pumping pods and mixing pod pictured in FIGS. 10A, 10B. The pumping pods have one fluid port connected to a pumping chamber moves water, dialysate etc into and out of the pod pump. The second port receives positive or negative pneumatic pressure to move the diaphragm in order to fill and then deliver water, dialysate etc through the first port. The pod pumps and the mixing pod mounted in ports the face of mixing cassette 1628 facing the directing cassette 1630 and are fluidly connected to the fluid paths in the mixing cassette 1632.

The directing cassette 1630 in FIG. 55 is a physical implementation of the directing circuit 142 in FIG. 6 minus the drain cassette 145, the dialysate tank 169, the heater 72 and the ultrafilter 73. The directing cassette 1630 is fluidly connected to the drain cassette 145, the dialysate tank 169, the heater 72 and the ultrafilter 73 of the directing circuit (FIG. 6) via flexible tubes. The directing cassette 1630 includes the four pneumatic valves 208 that control fluid flow through the pod pumps 159A, 159B of the directing circuit (FIG. 6). The directing cassette 1630 includes the other pneumatic valves 207, 147 of the directing circuit (FIG. 6) that control flow through the fluid channels and connections. The pod pumps 159A. 159B of the directing circuit (FIG. 6) are located between the mixing cassette 1632 and the directing cassette 1630. The pod pumps are mounted in ports on the face of the directing cassette 1630 facing the mixing cassette 1632 wherein the ports are fluidly connected to the fluid paths in the directing cassette 1630.

The balancing cassette 1628 is a physical implementation of the balance circuit 143 in FIG. 5. The balance cassette 1628 comprises the four pneumatic valves 213, 232, 223.242 control fluid flow through the pod pumps 161, 162 of the balance circuit (FIG. 5). The balance cassette 1628 also comprises other pneumatic valves 211, 212, 221, 222, 231, 241, of the balance circuit (FIG. 5) that control flow through the fluid channels and connections. The pod pumps 161, 162 of the balance circuit (FIG. 5) are located between the balance cassette 1628 and the directing the directing cassette 1630. The pod pumps are mounted in ports on the face of the balancing cassette 1628 that faces the directing cassette 1630 wherein the ports are fluidly connected to the fluid paths in the balance cassette 1628. The balance pods 341, 342 of the balance circuit (FIG. 5) are also mounted the face of the balancing cassette 1628 facing the directing cassette 1630 and in ports in the face of the directing cassette 1630 that is facing the balance cassette 1628. The ports for the balance pods are fluidly connected to the fluid paths in the balance cassette 1628.

The sensor cassette 180 is physically mounted on the mixing cassette. The sensor cassette receives fluid from a plurality of flowpaths in the cassettes. The temperature and conductivity of the fluid from each flowpath is measured and reported to the hemodialysis unit controller.

Dialysis Cassettes

The three dialysate cassettes 1628, 1630, 1632 have similar designs and constructions. The following description is specific to the mix cassette 1632, but applies to the directing cassette and balance cassette. All three dialysis cassettes comprise a middle plate with a plurality of open channels on each side. The larger channels are fluid channels that lead valve stations, pump stations and ports in the face of the cassette. The narrow channels are pneumatic channels that connect actuation ports on one edge of the cassette to the actuation chambers of the pumps and valves. The front and back plates are fused to the top of the channels and stations to create air and fluid tight passages and chambers. The front and back plates also include pneumatic ports actuate the pod pumps and fluid ports to the pod pumps and other conduits.

Figure 42:
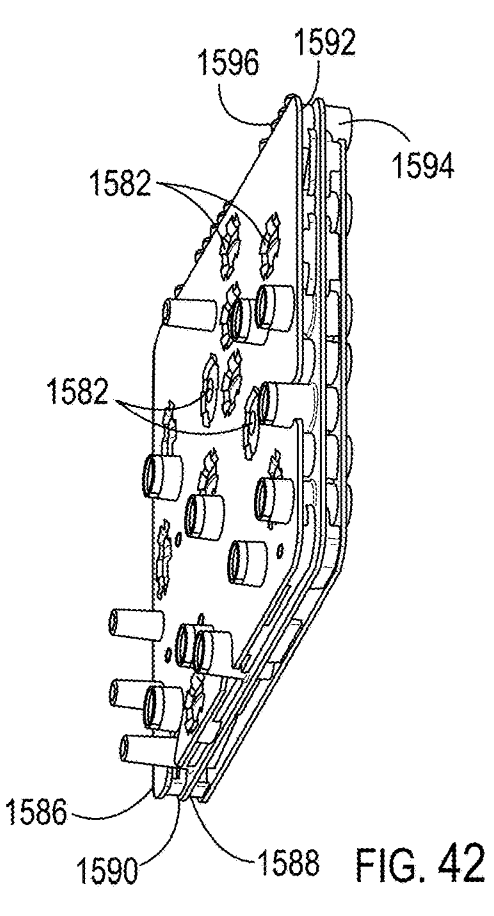
FIG. 42 is perspective view of the mixing cassette.

Referring now to FIG. 42, an exploded view of the integrated cassette assembly 1626 shows the mixing cassette 1632 on the left, the directing cassette 1630 in the middle and the balance cassette 1628 on the right. The balance pods 1636 are located between the directing cassette 1630 and the balance cassette 1628. A port on the balance pod 1636 plugs into a fluid port 1662 in the directing cassette 1630. The joint between the balance pod port and the fluid port 1662 is sealed with an O-ring 1660. O-rings 1660 are used to seal the ports 1634A of the pod pumps 1634 where they is plugged into the either pneumatic ports or fluid ports. The pod pumps 1634 between the directing cassette and the balance cassette 1628 are a physical embodiment of the pod pumps 161, 162 in FIG. 5. The directing cassette 1630 and the balance cassette 1628 are also fluidly connected by one or more conduits 1638.

The mixing cassette 1632 is connected to the directing cassette 1630 by a number of conduits 1638, pod pumps 1634 and a mixing chamber 1635. The conduits 1638, pod pumps 1634 and mixing chamber 1635 are fluidly connected to either fluid ports or pneumatic ports in the faces of the cassettes. A O-ring 1660 seals each joint between the cassette ports 1622 and the pump ports 1662.

Figure 43:
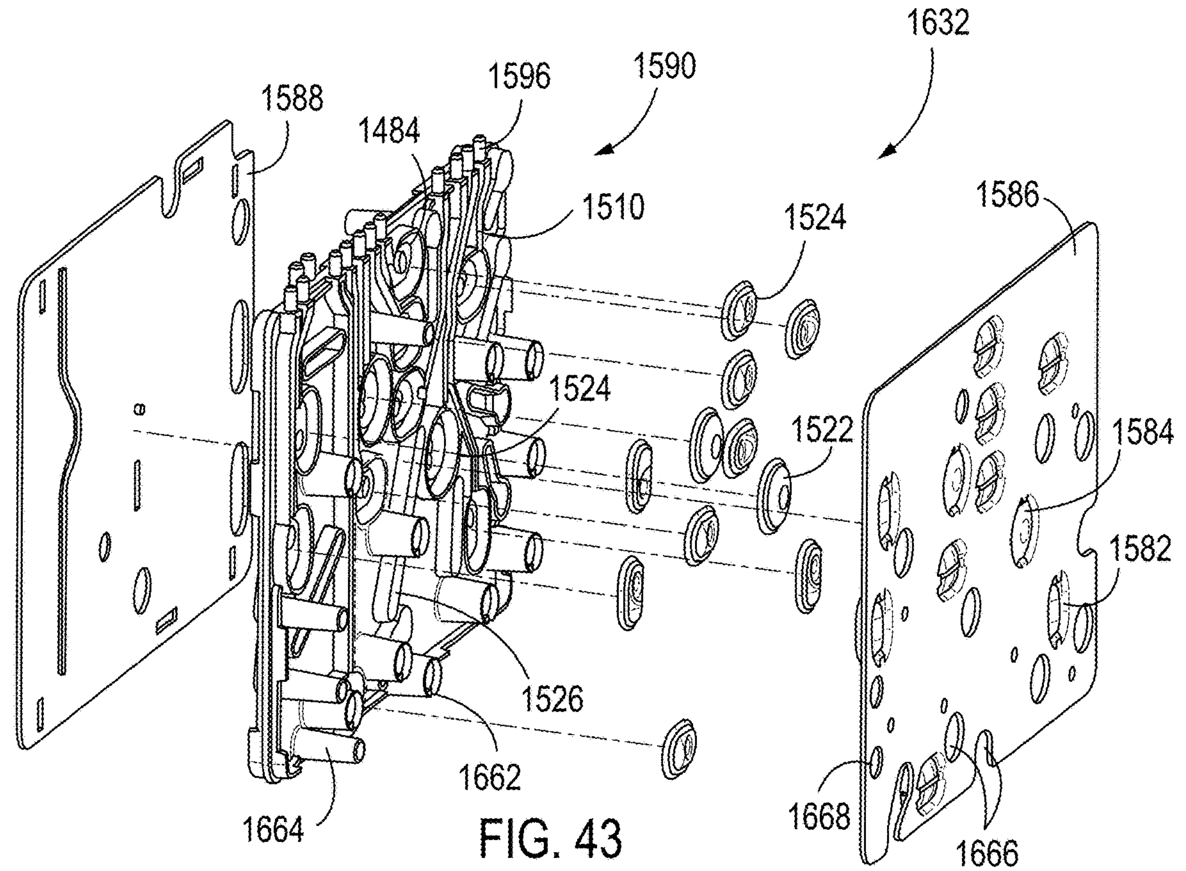
FIG. 43 is an exploded view of the mixing cassette.

FIG. 43A shows a perspective view of an exemplary mixing cassette 1630 that includes a plurality of valve stations 1582 and pump stations 1584. In one example, a cassette was constructed to have a length of about 16 cms, a width of about 19 cms and a thickness of about 1.5 cms. The first outer plate or actuation plate 86 has been molded with indentations on its external surface at the valve 1582 and pump 1584 stations to provide a curved inner surface to conform with the associated diaphragms in those regions. In this example, the nominal thickness of each of the first outer plate 1586, the second outer plate or liquid-side plate 1588 and the middle plate 1590 is approximately 2 mm, whereas the overall thickness of the cassette is approximately 15 mm. The cassette actuation channel ports 1596 are shown arrayed within the first inter-plate space 1592 of the cassette 1580. Thus a diaphragm excursion of about 4.5 mm can be achieved in a cassette whose width is about 10.5 mm plus the width desired for liquid channels in the second inter-plate space 1594.

FIG. 43B shows an exploded view of the mixing cassette showing the first side of the middle plate 1590 comprising a plurality of pneumatic channels 1510, valve stations 1518, pump stations 1484 and liquid channels 1526. The first plate 1586 is fused to the top edges of the channels and the perimeter walls around the valve and pump stations to create closed pneumatic and liquid conduits. The first plate 1586 captures the valve diaphragms 1524 and pump diaphragms 1522 against valve and pump stations of the middle plate 1590. The second plate 1588 is similarly fused to the outer edges of the fluid channels on the second side of the middle plate 1590 to create fluid conduits. The first outer plate 1586 includes holes and notches 1666 to accommodate the plurality of ports 1662 and the spouts 1664 that fluidly connect the mixing cassette 1632 to other elements in the hemodialysis system.

Figure 44:
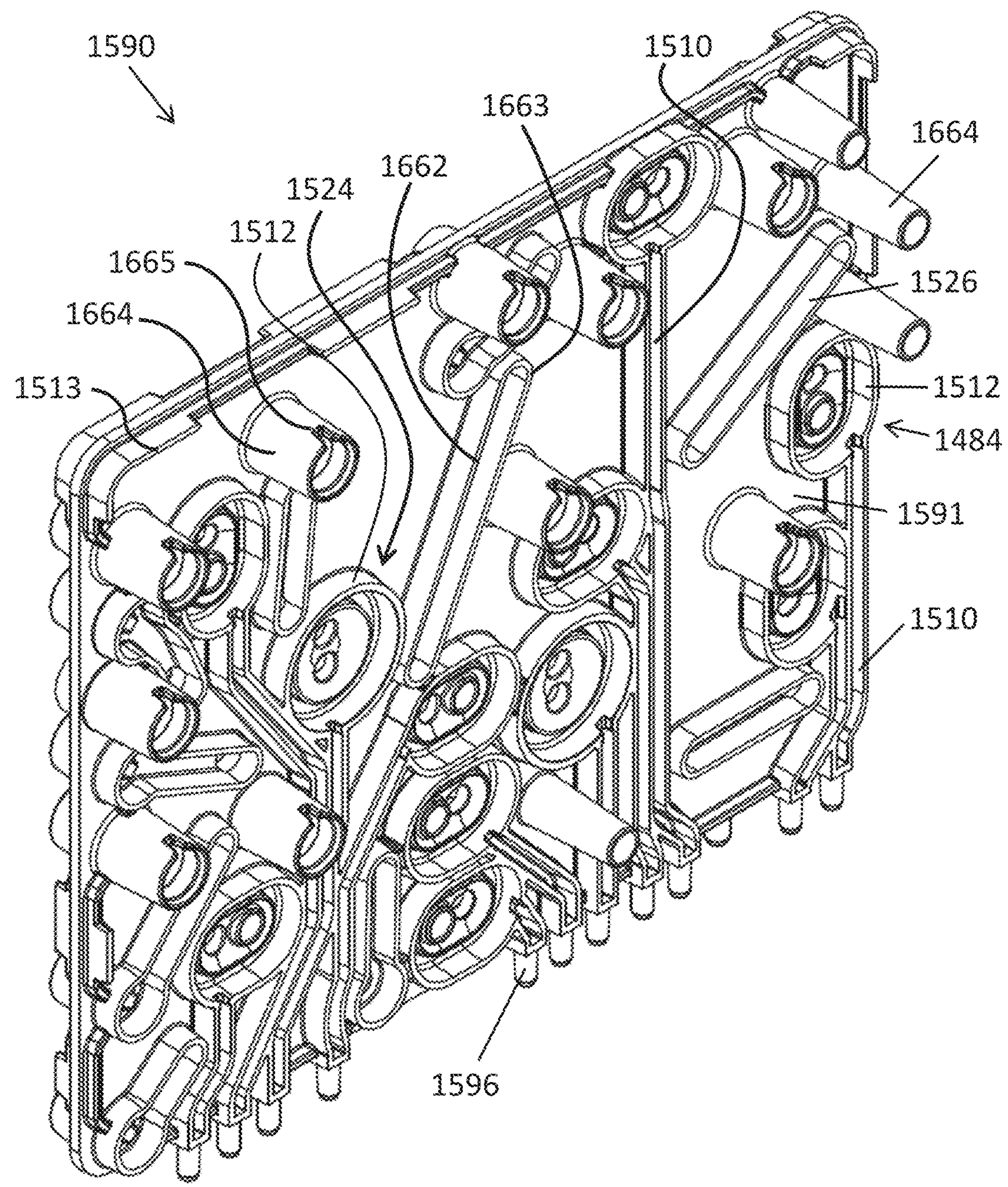
FIG. 44 is a perspective view of the actuation side of the middle plate of the mixing cassette.

FIG. 44 shows a perspective view of the first side of the middle plate 1590 of cassette 1630. In this example, the actuation channels 1510, valve and pump station perimeter walls 1512, and cassette actuation ports 1596 have been formed or molded as part of the middle plate 1590. In this example, most of the diaphragm valve stations 1484 or pump stations 1524 are fed by a separate actuation channels 1510 leading from a dedicated cassette actuation port 1596. The cassette's actuation channels 1510 comprise two walls that extend up from the center plate 1591 of the middle plate 1590 and spanning the inter-plate space. Adjacent channels may share a wall. In some cases, it may be desirable to actuate two or more valve stations at once, in which case a single actuation channel path is fluidly connected to two or more valve stations. Each valve station 1484 is surrounded by a perimeter wall 1512 that seals the station when the top edge is fused to the adjacent first plate 1586. The first plate 1586 may also be fused to the top edge of walls 1513 around the perimeter of the middle plate 1590 to strengthen and stiffen the cassette 1632.

Continuing to refer to FIG. 44, fluid channels 1662 may be formed on the first side of the middle plate 1590. Fluid channels 1662 generally connect a first opening or port through the center plate 1591 to a second opening or port. The fluid channel comprise two walls that extend from the center plate 1591 to the same height as the actuation channels or valve stations. In most cases the two walls of the fluid channels are joined at each end of the channel 1663 and can be described as a single wall that encloses a channel. The fluid channel 1662 on the first side of the middle plate is are closed into a conduit by fusing the first plate onto the top edge of the fluid channel walls. Fluid may move into or out of the mixing cassette 1632 via ports 1664 that receive rigid conduits or pod pumps. Some ports 1664 include a notch 1665 that receives a matching ridge on the conduit or pod pump ports. The notch keeps the pod pumps and conduits from rotating about the center of the port and increasing the rigidity of the integrated cassette assembly. The spouts 1664 provide a fluid connection to a flexible tube to another cassette, a tank, a heater or other element outside the integrated cassette assembly 1626.

Figure 45:
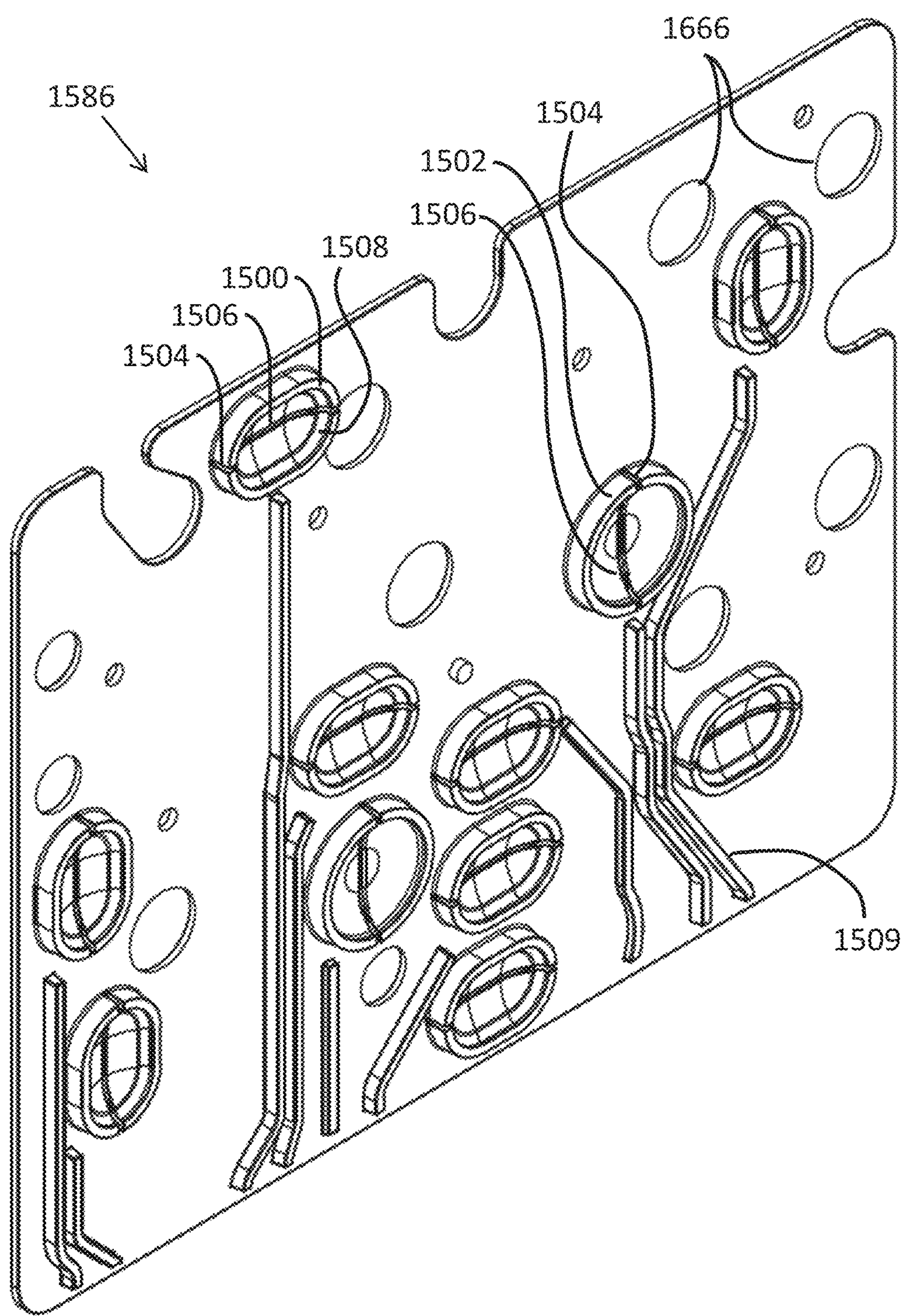
FIG. 45. is a perspective view of the inner side of the plate on the actuation side of the mixing cassette.

FIG. 45 shows a perspective view of the inner side of the first plate 1586 of cassette 1632. In this example, the diaphragm retainer or retaining walls 1500, 1502 have been molded as an integral part of the internal side of the first outer plate 1586. In this example, each diaphragm retainer 1500, 1502 has a number of fenestrations or holes 1504 and optionally a top-side groove 1506 to distribute actuation pressure evenly over the diaphragm to be retained against the middle plate 1590. The curved inner walls 1508 of the outer plate 86 in the valve and pump stations are arranged to conform with the associated diaphragm shape as it extends fully into the actuation chamber (within which the retainers 102 are placed). In some cases, optionally, ribs 109 may be included in the mold of the outer plate 1586, which are configured to encroach mating actuation channels of the opposing middle plate. Ribs 1509 may be constructed to have a cross-sectional size and length to adjust the total volume of the associated actuation channel to a pre-determined volume. This may minimize the amount of pneumatic gas volume to be delivered (or compressed), and may improve the responsiveness of the associated diaphragms to actuation by a pressure delivery manifold.

Figure 46:
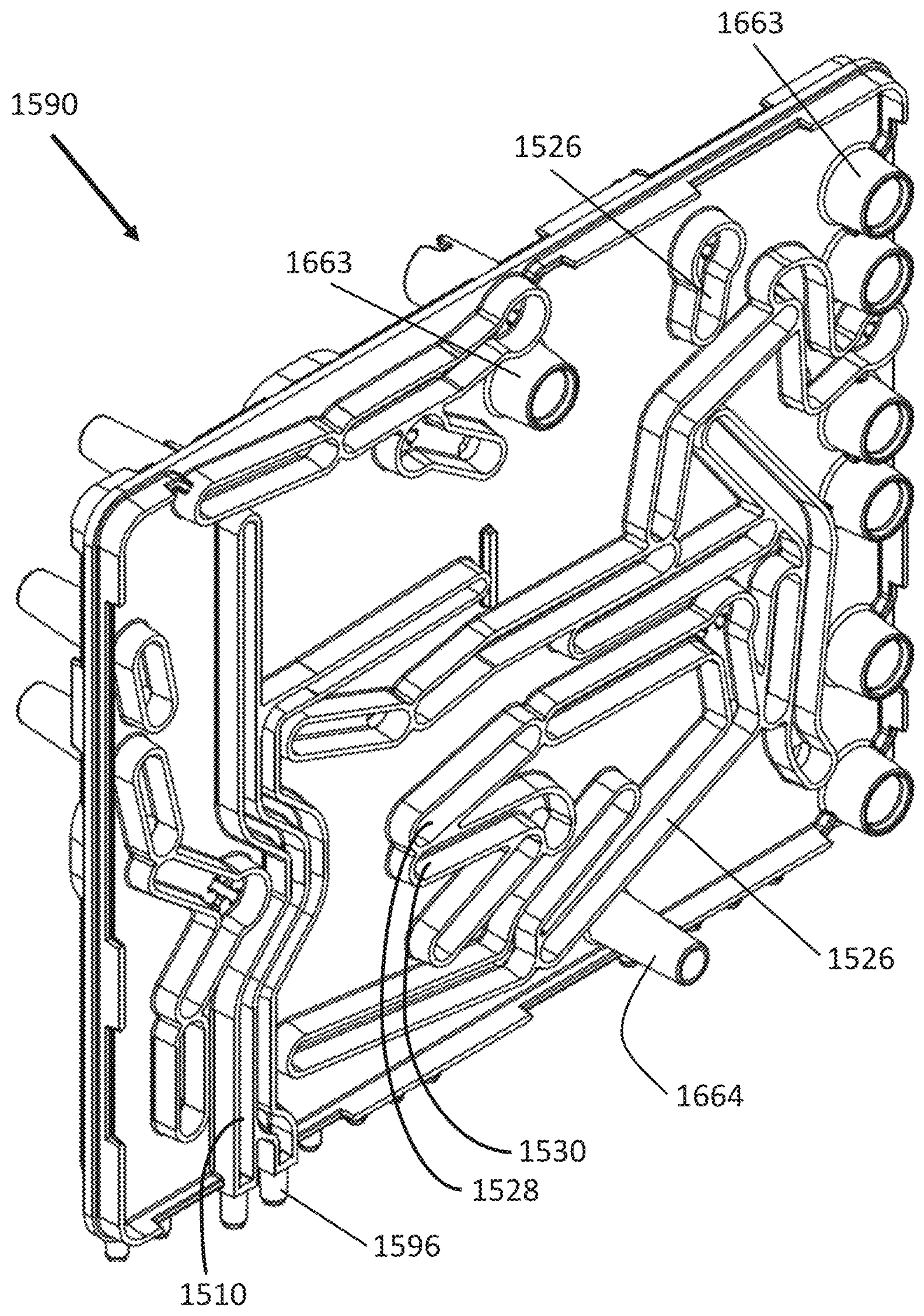
FIG. 46 is a perspective view of the fluid side of the middle plate of the mixing cassette.

FIG. 46 shows the second side of middle plate 1590 of mixing cassette 1632. In this example, the liquid channels 1526 have been molded in as part of the middle plate 1590. In the case of a pump station 1524 (FIG. 44), each of the two ports 1624A, 1624B is associated with a separate liquid channel 1528, 1530, so that one port functions as an inlet port of the pump chamber, whereas the other port functions as an outlet port of the pump chamber. Whether a particular port functions as an inlet or outlet can be determined by which downstream valve is actuated or closed. The second side of the mixing cassette middle plate 1590 also comprises actuation channels that connect actuation ports 1596 to ports 1622 that receive pod pumps in the directing circuit to actuate the directing circuit pod pumps. The second side of the middle plate 1590 further comprises sensor ports 1663 and a spout 1664. The sensor ports 1663 provide a fluid connection to the sensor cassette 1800 as will be discussed below. The spot 1664 provides a fluid connection via a flexible tube.

Figure 47:
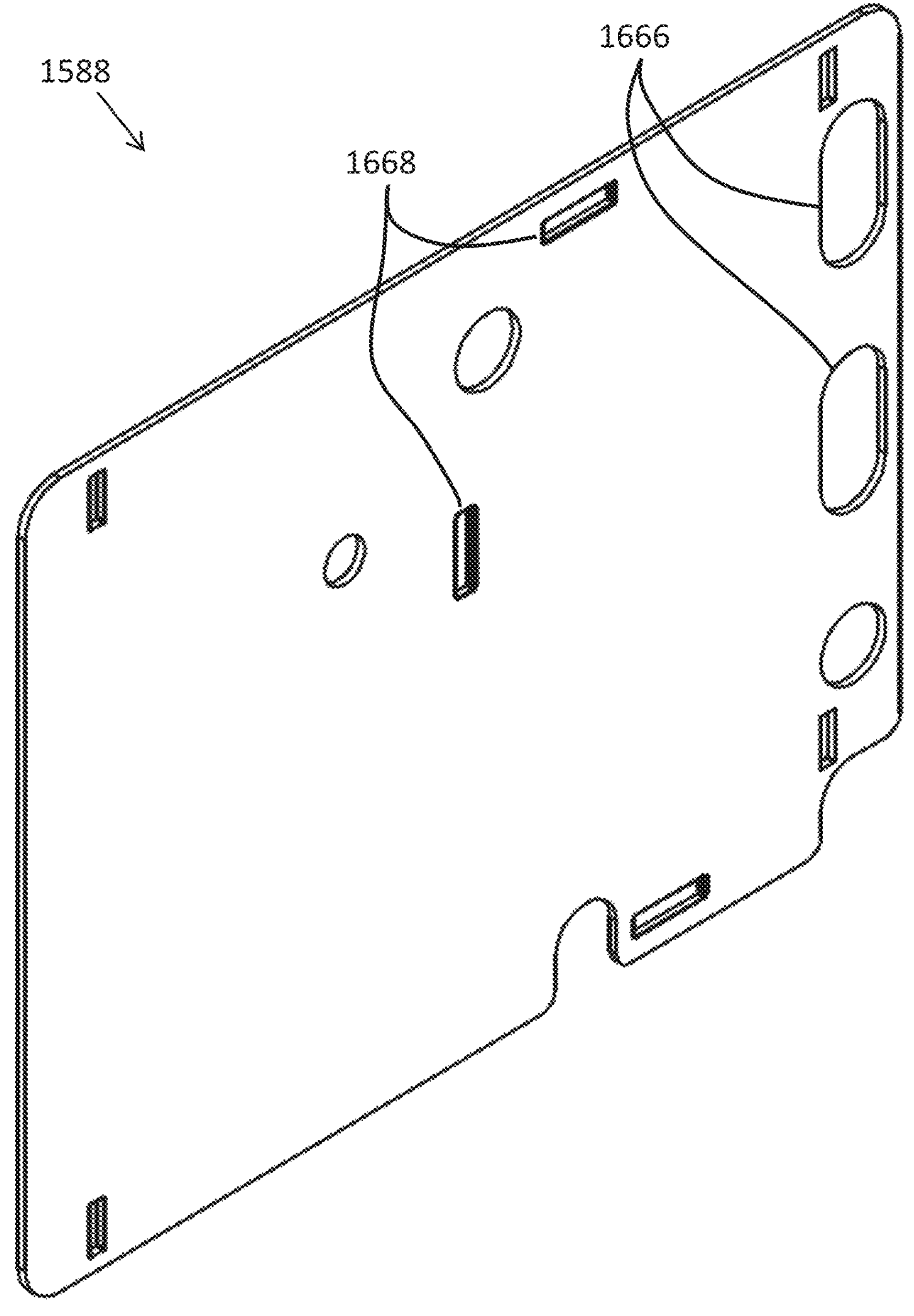
FIG. 47. is a perspective view of the inner side of the plate on the fluid side of the mixing cassette.

FIG. 47 shows the outer side of the second plate 1588 of the mixing cassette. The second plate 1588 is fused to the top edges of the fluid channels 1526 and the actuation channels 1510 to create conduits for fluid and pneumatic gas. The second plate 1558 comprises openings 1666 to the sensor ports 1663. In one embodiment the openings are not fused to the ports or any part of the middle plate 1590. The openings 1666 on both outer plates 1586, 1588 are sized to provide a location fit over the ports 1662, 1663. In an embodiment, the openings 1666 serve to key and orient the outer plates 1586, 1588 on the middle plate 1590 during fabrication. The openings 1666 assure the correct outer plate is mounted on the correct side of the correct middle plate 1590.

Sensor Cassette

Figure 48:
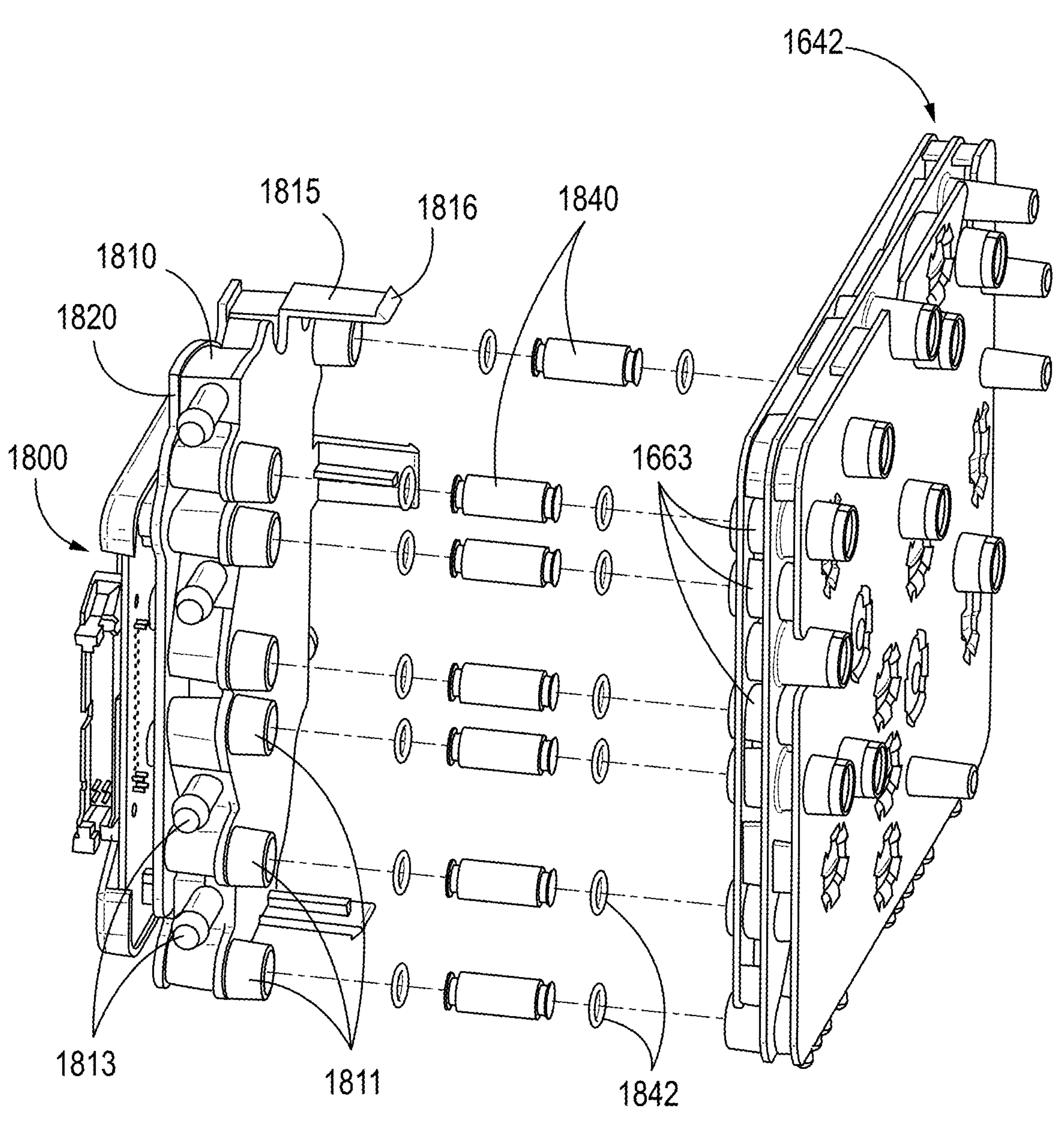
FIG. 48 is an exploded view of the mixing cassette and sensor cassette.

Referring now to FIG. 48, the sensor cassette 1800 is part of the integrated cassette assembly 1626. The sensor cassette 1800 is mounted to one end of the integrated cassette assembly 1626 (FIG. 40). In one embodiment, the sensor cassette is mounted to the mixing cassette 1632 and plumbed through rigid tubes 1840 to the mixing cassette 1632.

Continuing to refer to FIG. 48, the sensor cassette 1800 is fluidly and structurally connected to the mixing cassette 1632. Attaching the sensor cassette 1800 to the integrated cassette assembly 1626 simplifies the installation of the dialysate elements into the hemodialysis unit 51. Reducing the number of flexible tubes attached to the sensor cassette reduces the assembly cost. The cassette manifold 1810 includes legs 1815 with steps at the end that fit into and then grip slots 1668 seen in FIG. 47. The legs 1815 are living hinges and the step include tapered end 1816, so the legs 1815 deflect as the tapered ends 1816 are pushed into the slots 1668 (FIG. 47) before snapping into position once fully inserted. Referring now to FIGS. 46, 47, the slots in the second plate 1588 are located to not enter the fluid paths 1526 shown FIG. 46. Referring now to FIG. 48, the insertion of the legs 1815 into the slots 1668 (FIG. 47) is limited by the rigid short tubes 1840 that fluidly connect the ports 1811 on the sensor cassette 1800 to the sensor ports 1663 (FIG. 46.) The legs 1815 and the rigid short tubes 1840 are sized so that the tapered ends 1816 are inserted just far enough into the slots 1668 to snap into place locking the sensor manifold 1800 to the mixing cassette 1632.

The short tubes 1840 create a short and direct fluid path to the fluid paths in the mixing cassette. The sensor cassette 1800 may receive fluids from other cassettes in the integrated cassette assembly through the fluid conduits between the mixing cassette and the directing cassette. In one embodiment, the short tubes are sealed to the sensor ports in the mixing cassette and the ports 1811 in the sensor cassette with O-rings 1842. In one embodiment, the short tubes are incorporated into either the molded middle plate 1590 of the mixing cassette or the molded cassette manifold 1810 of the sensor cassette, which would reduce by half the number of O-ring joints between the mixing cassette and the sensor cassette.

Figure 49:
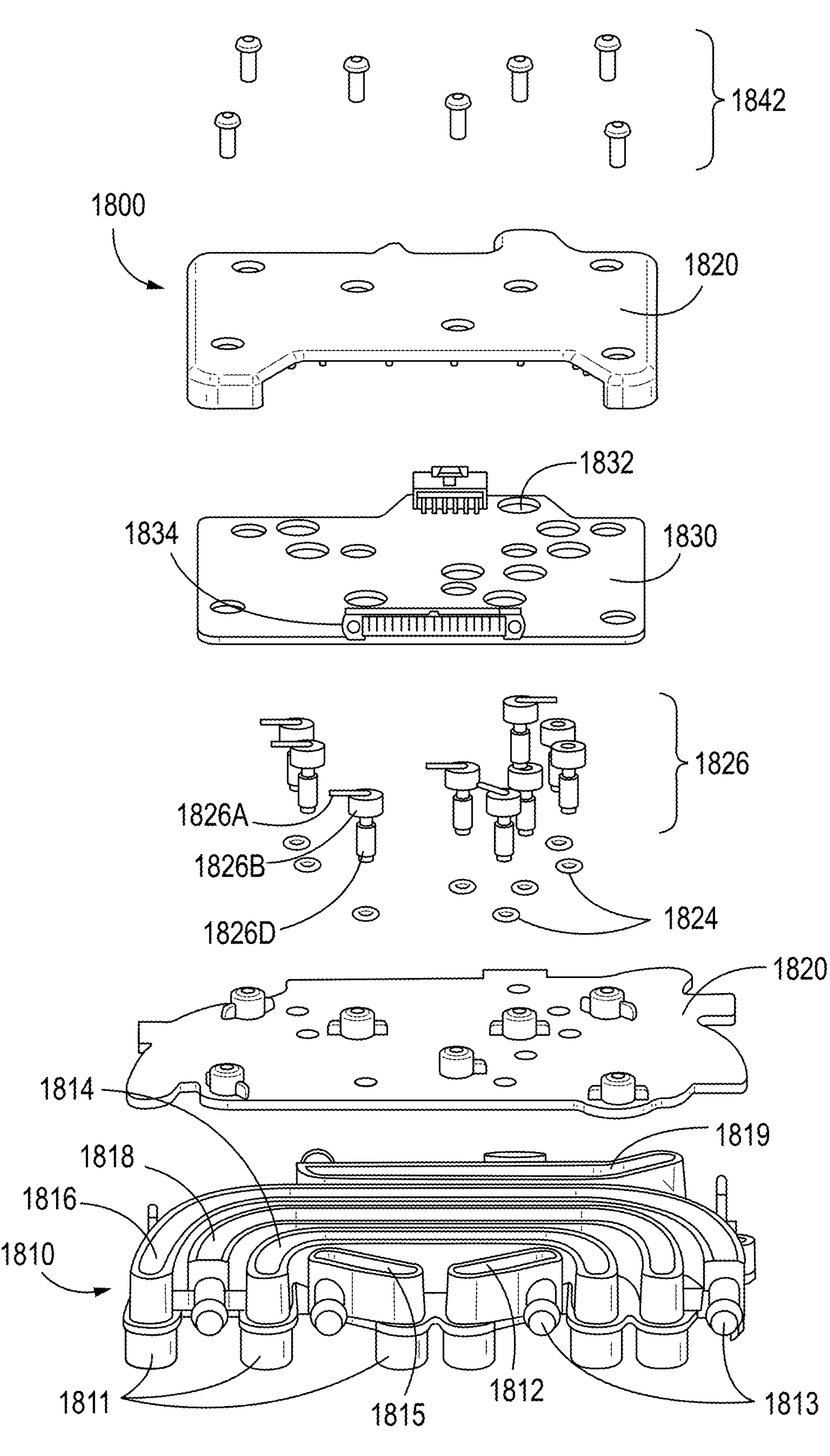
FIG. 49 is an exploded view of the sensor cassette.

The components and function of the sensor cassette is best understood by referring to the exploded view of the sensor cassette in FIG. 49. The sensor cassette 1800 includes a cassette manifold 1810 with a plurality of isolated fluid channels, a top plate 1820 that mounts on the top of the channels to create a plurality of isolated flow paths, a plurality of sensor probes 1826 that extend into the flow paths and are electrically connected to the PCB 1830 and a cover 1840 with fasteners 1842. The fasteners 1842 pull the cassette manifold 1810 toward the cover 1840, thereby combining the cassette manifold 1810, cover 1840, the top plate 1820, PCB 1830 with the sensors 1826 into the sensor cassette 1800. PCB 1830 is shown with electrical connector 1834. PCB 1830 also contains opening 1832 for attachment to top plate. The connector 1834 may be connected to the controller of the hemodialysis system.

Referring now to FIG. 49, one or more subject media, preferably a liquid in these exemplary embodiments, may be contained in or flow through cassette manifold 1810. For example, one subject media may enter cassette manifold 1810 via port 1811 and exit the cassette manifold via tube connector 1813. Between tube connector 1811 and 1813, there is a fluid path 1816 though the cassette. Likewise fluid paths 1812, 1815, 1816 1819 extend from one of a plurality of tube connectors 1811 and one of a plurality of barbed connector 1813. Fluid path 1814 extends between a first port 1811 and a second port 1811. Each fluid path is fluidly distinct and separated for the other fluid paths. Each fluid path may contain subject media of different composition or characteristics. In other embodiments, one or more fluid paths may contain the same or similar subject media. In certain embodiments, the same subject media may be flowed through more than one flow path at the same time to check and/or calibrate the sensor apparatus systems associated with such fluid paths The cassette manifold 1810 and the top plate 1820 may be constructed of a variety of materials. Generally, in the various exemplary embodiment, the materials used are solid and non-flexible. In the preferred embodiment, the plates are constructed of polysulfone, but in other embodiments, the cassettes are constructed of any other solid material and in exemplary embodiments, of any thermoplastic. Preferred embodiments of sensor manifold 1810 may be fabricated utilizing the systems and methods described in U.S. Patent Application entitled Cassette System Integrated Apparatus Ser. No. 12/038,648, which is being filed on even date herewith.

Continuing to refer to FIG. 49, in exemplary embodiments of the sensor manifold 1810, ports 1811 and tube connectors 1813 are utilized to bring subject media into or remove subject media from fluid paths 1812, 1814, 1815, 1816, 1819. Sensing probes, such as sensing probe 1826 extending into fluid paths are incorporated into sensor manifold 1810 so as to determine various properties of the subject media contained in or flowing through the particular fluid path in the sensor manifold. In various embodiments one sensing probe may be utilized to sense temperature and/or other properties of the subject media. In another embodiment, two sensing probes may be utilized to sense temperature and/or conductivity and/or other properties of the subject media. In yet further embodiments, three or more sensing probes may be included. In some embodiments, one or more combination temperature and conductivity sensing probes of the types generally described herein may be utilized. In other embodiments, the conductivity sensors and temperature sensor can be any conductivity or temperature sensor in the art. In one embodiment, the conductivity sensor elements (or sensor leads) are graphite posts. In other embodiments, the conductivity sensors elements are posts made from stainless steel, titanium, or any other material of the type typically used for (or capable of being used for) conductivity measurements. In certain embodiments, the conductivity sensors will include an electrical connection that transmits signals from the sensor lead to a sensor mechanism, controller or other device. In various embodiments, the temperature sensor can be any of the temperature sensors commonly used (or capable of being used) to sense temperature. In accordance with certain embodiments, sensor manifold 1810 is passive with respect to control of the fluid flow and does not contain valves or pumping mechanisms to control the flow of the subject media. In such embodiments, the flow of the subject media may be controlled by fluid control apparatus external to sensor manifold 1810.

Continuing to refer to FIG. 49, the sensing probes, such as sensing probe 1826, may be all the same, may be individually selected from various sensors based on the type of function to be performed, or the same probe may be individually modified based on the type of function to be performed. Similarly, the configuration of the fluid paths, such as the length of the fluid path and the shape of the fluid path, may be selected based on the function to be performed. By way of example, to detect the temperature of the subject media in a fluid path, a temperature sensor, such as a thermistor, may be used.

Again, by way of example, to measure the conductivity of the subject media, one sensing probe configured to measure temperature and conductivity. The sensing probe 1826 comprises electrically and thermally conductive well 1826D that when assembled extends through the top plate 1820 and into the flow paths in the cassette manifold 1810. Sensing probes that measure temperature include a thermistor located inside the thermally conductive well 1826D. The thermistor is electrically connected by wires 1826A to circuits on the PCB 1830 to determine the thermistor temperature. In embodiments, where the conductive is measured, a second sensor 1826 is placed in base fluid pathway at the known distance from the first sensor 1826. The first and second sensing probes 1826 comprises a conductive wire or electrical connection between the circuit on the PCB and the conductive surface 1826D of the probe. The circuitry on the PCB 1830 measures the electrical impedance between the first and second sensor and determines the conductivity of the fluid based on the measured impedance and the temperature of the fluid measured by the thermistor.

Balance Pods

Figure 50:
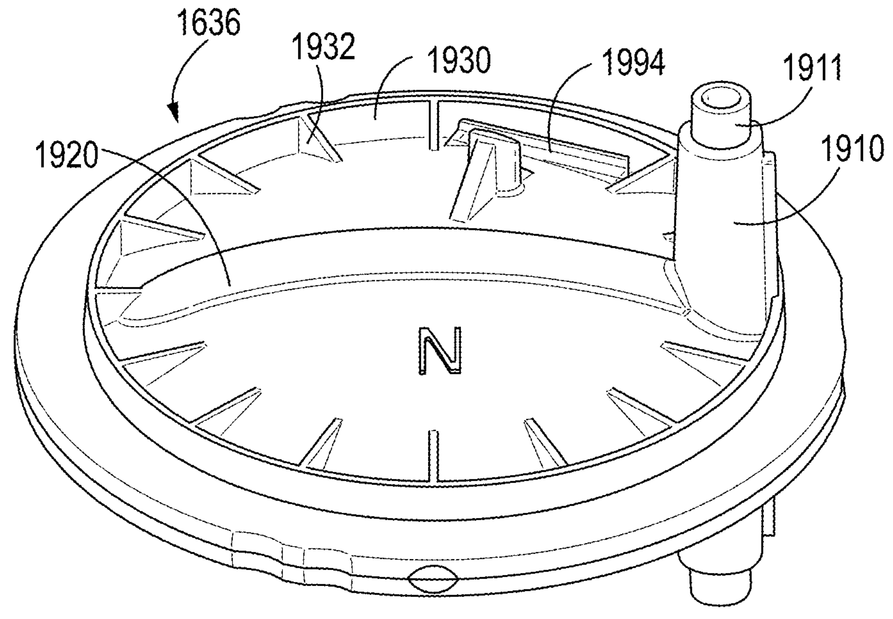
FIG. 50 is a perspective view of the balance pod from the cassette assembly of FIG. 40.
Figure 51:
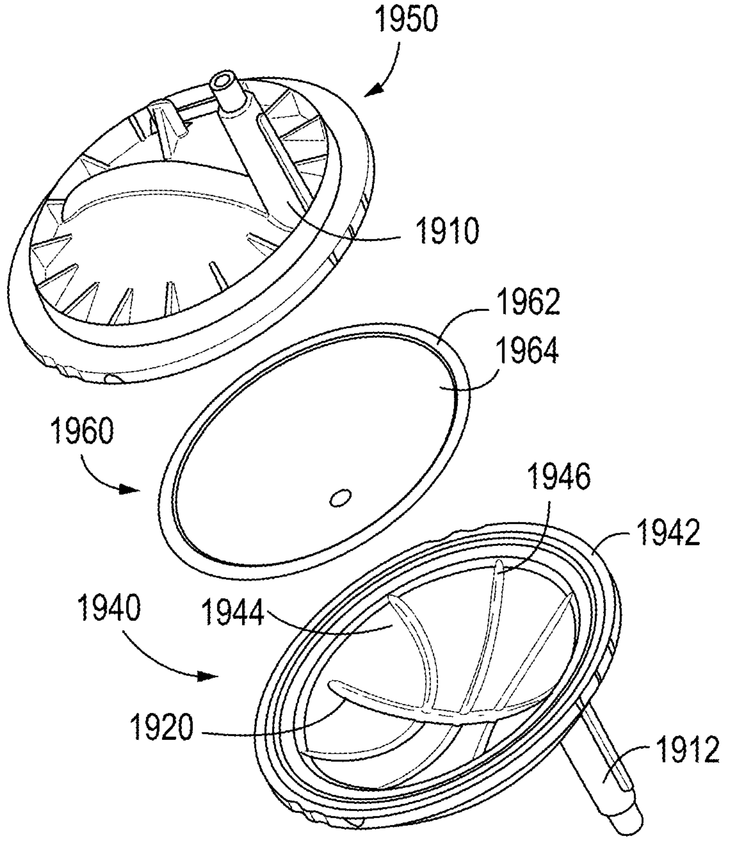
FIG. 51 is an exploded view of the balance pod.

The balance pod 1636 in FIG. 50 is a physical implementation of one of the balance pods 341, 342 in the balance flow circuit 143 in FIG. 5. The balance pods 341, 342 assure equal volumes of dialysate are pumped into and out of the dialyzer 14. Referring now to FIG. 51, a balance pod is formed from attaching a first rigid domes 1940 to a second rigid dome 1950 and trapping a membrane 1960 between the two rigid domes to create a first chamber and second chamber. The first chamber is defined by dome 1940 and the diaphragm 1960. The second chamber is defined by dome 1950 and the diaphragm 1960. The rigid domes fix the total volume of first chamber and the second chamber, so any increase in the first chamber volume results in a decreased volume in the second chamber. Referring now to FIG. 2, the first chamber receives clean dialysate from the directing circuit 142 and the second chamber receives used dialysate from the one of the pod pumps 15 in the balance circuit.

Referring now to FIGS. 51 and 5, in an exemplary process the diaphragm 1960 starts in a position against the second dome 1950, so the first chamber is full of clean dialysate and the second chamber volume is near zero. In the next step, the pod pump 162 (FIG. 5) pushes a pod pump volume of used dialysate into the second chamber of the balance pod 342, which displaces the clean dialysate in the first chamber toward the dialyzer 14. The balance pod 1936 is sized have the same volume as the pod pumps 1634, so a full stroke of a pump pod drives the diaphragm from the second dome 1950 to the first dome 1940 there by emptying the first chamber and filling the second chamber.

Balance pods are distinct from the pod pump 1634 in FIG. 10A, wherein one of the chambers (actuation chamber) is filled with air. In the balance pod both chambers in are filled with liquid. One theory among others is that having liquid on both sides of the diaphragm in 1636 creates higher momentary loads on the diaphragm 1960 and the dome chambers 1940, 1950. The balance pod 1936 includes several features to strengthen the domes and make the domes and the diaphragm more resilient the cyclic loading as dialysate moves through the balance pod.

Figure 52:
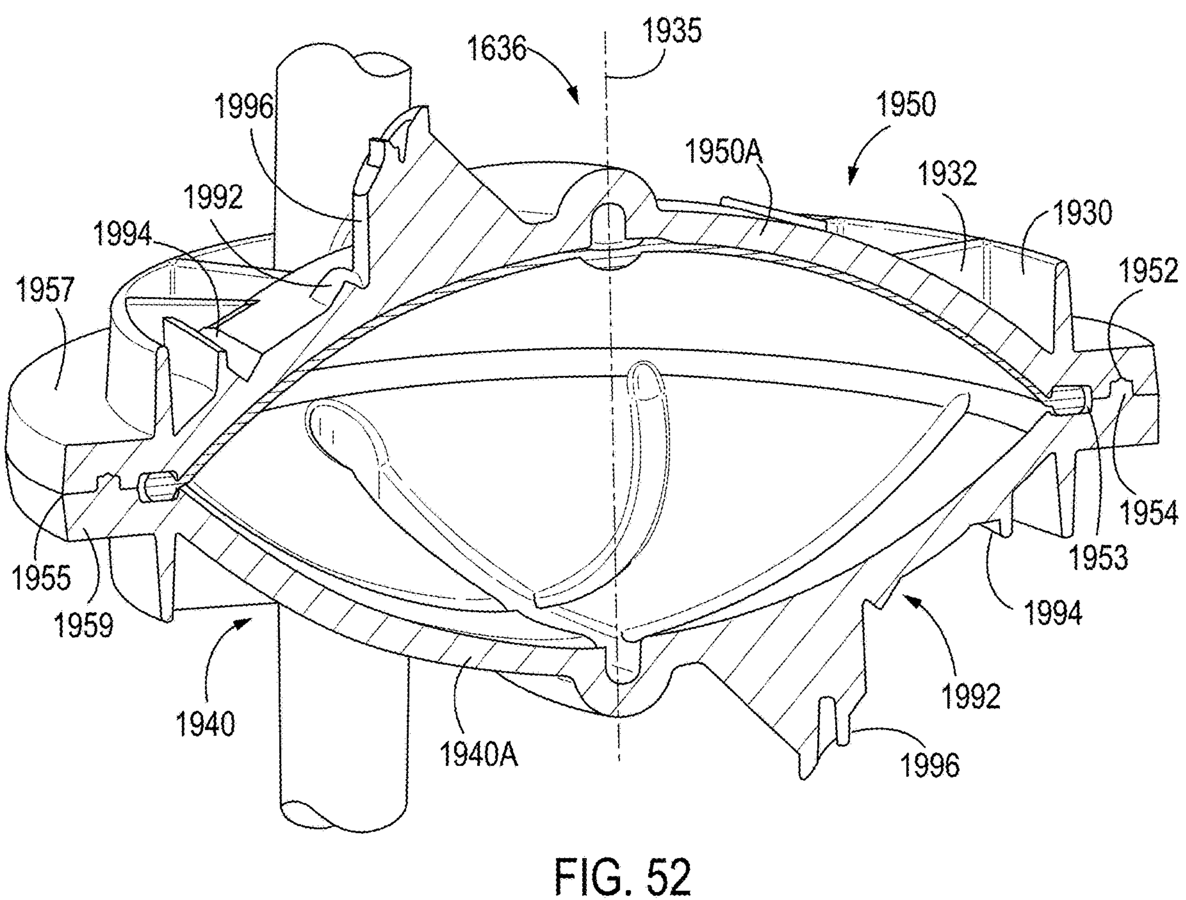
FIG. 52-53 are cross-sectional views of the balance pod.

Referring now to FIG. 52, the pressure applied by the pod pumps to push fluid into the balance pod 1636 tends to push the two chambers 1940, 1950 apart. The two chambers 1940, 1950 are joined by a fused joint between the two rims 1957, 1959. In one theory, among others, the pressure on the inside of the domes may cause the center of domes to move away from each other and create a bending moment at the joint between the two rims 1957, 1959. In one embodiment, the fusion joint is located inboard of the outside diameter 1955 to reduce the bending stress on the joint. In an example, a fusion joint is created in the center of rim half way between the OD 1955 and the gland for the diaphragm 1953. Locating the joint at the midpoint of the rim 1957, 1959 changes the bending load to a tensile load.

Continuing to refer to FIG. 52, in one embodiment, the fusion joint is formed where a circumferential ridge 1954 extends above rim 1959 and is received by a matching circumferential groove 1952. A fusion joint at 1951 has several advantages. Locating the joint away from the OD of the rim reduces the bending load and reduces the magnitude of the load. The insertion of the ridge 1954 into the groove 1952 both properly locates the two chambers for assembly and reduces tendency of the rims to rotate away from each other about the outer diameter 1955. The fusion joint may made in one of several ways including laser weld, an ultrasonic weld or an adhesive weld.

Continuing to refer to FIG. 52, in an embodiment the chambers 1940, 1950 include a fence 1930 with gussets 1932 to stiffen the domes 1940A, 1950A and thereby reduce the bending at the rim 1957, 1959. In one example, the fence 1930 is a thin cylinder that extends axially from the joint of the dome 1950A and the rim 1957 and is centered on the dome axis 1935. The fence 1930 further stiffens the dome 1950A with gussets that extend radially from the fence 1930 to the dome 1950A. The fence 1930 and gussets are less than half the thickness of the dome 1950A. The fence extends to approximately half the height of the dome 1950A. Here approximately may read as plus or minus 10% of height of the dome.

Referring now to FIG. 50, the gussets 1932 are distributed around the circumference of the fence, where the angular distance between the gussets is generally 22 degrees. In one example the fifteen gussets 1932 are distributed around fence 1930. In an example, there are larger angular gaps between the adjacent gussets to accommodate an inlet port 1910 or sensor mount features 1994 on the dome 1950. In an example, the top of the gussets 1932 extend horizontally from the top of the fence, where horizontal is perpendicular to the dome axis 1935.

Referring now to FIG. 51, each dome 1940, 1950 includes open channels 1920, 1944, 1946 to prevent fluid being trapped under the diaphragm 1960, when the diaphragm is contacts the inner surface of the dome 1940A, 1950A. Center channel 1920 extends radially from the fluid port of the inlet/outlet line 1912, 1910 across most of the dome. Here most of the dome refers to 75% to 90% of dome diameter. Furthermore, there are three open channels 1944, 1946 that extend perpendicularly from the center channel to near the edge of the dome surface. In this case, "near" means with 5% of the dome diameter. The middle open channel 1946 extend radially from the center of the dome. The curved open channels 1944 curve away from the middle channel 1946 to be equal distant on a circumferential basis from the middle open channel 1946 and the center open channel 1920.

Figures 53, 54:
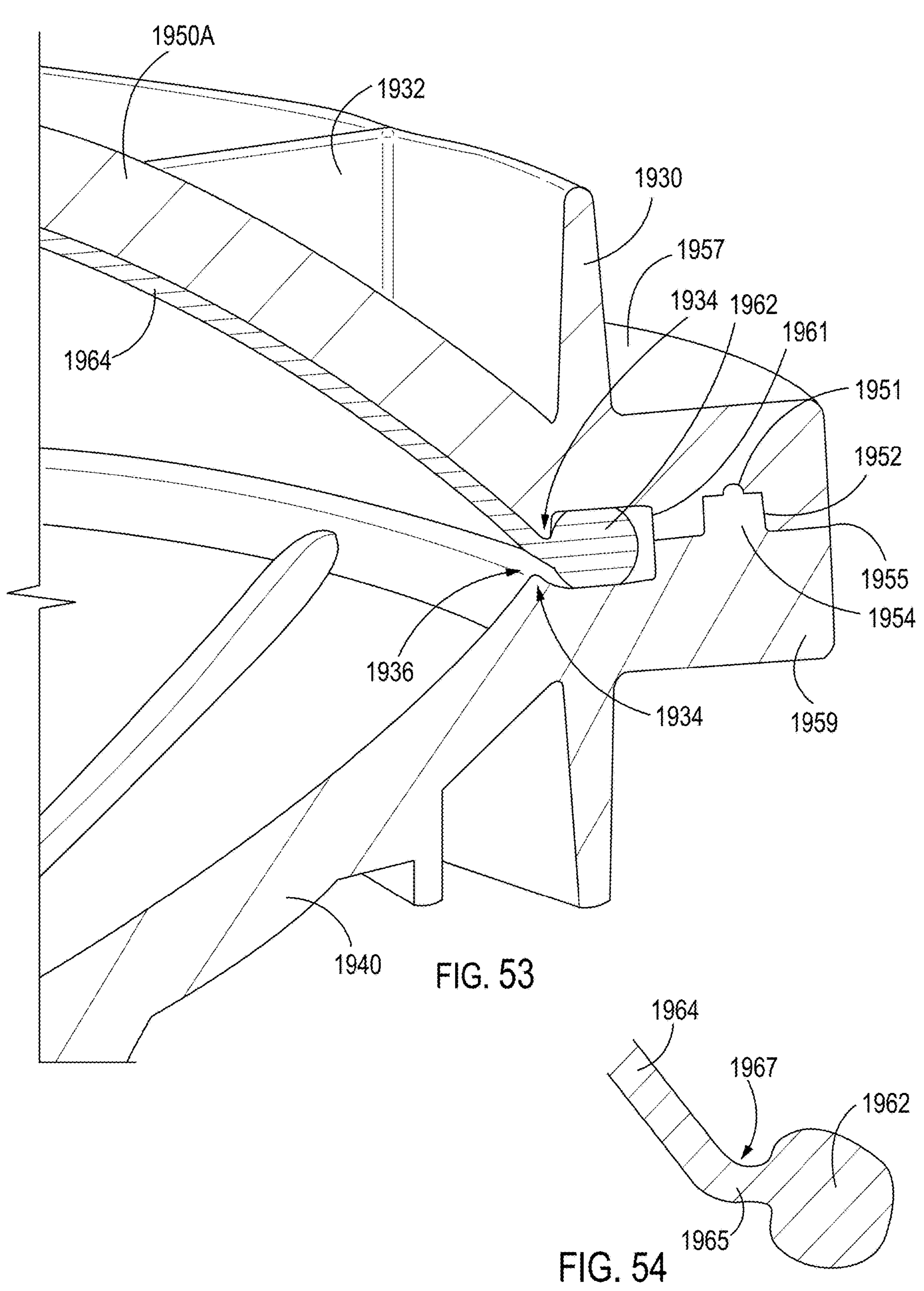
FIG. 54 is a cross-sectional detailed view of a diaphragm in the balance pod.

Referring now to FIGS. 53, 54, the diaphragm and the inner surface of the rigid domes 1940, 1950 are designed minimize the bending stress on the membrane 1964 of the diaphragm 1960. The diaphragm is molded with a thick rim 1962. The thick rim 1962 is received by the gland 1961 in the rigid domes. The membrane 1964 extends radially from the thick rim 1962 as shown in FIG. 54. The flat section 1965 extends radially before forming a curve 1967. The inner dome surface in the rigid domes 1940, 1950 extends to form a ridge 1934 that supports the membrane curve 1967 as the diaphragm 1960 changes from a flat section 1965 to a surface 1964 that contacts inner surface of one of the domes 1940A, 1950A. The design goal is to locate the maximum bending stress in the membrane away from the thick rim 1962. In one theory, among others, the bending stress on a membrane is reduced when the membrane thickness is reduced. Locating the bend 1967 away from the thick rim 1962 puts the stress on thin section of the diaphragm.

Figure 56:
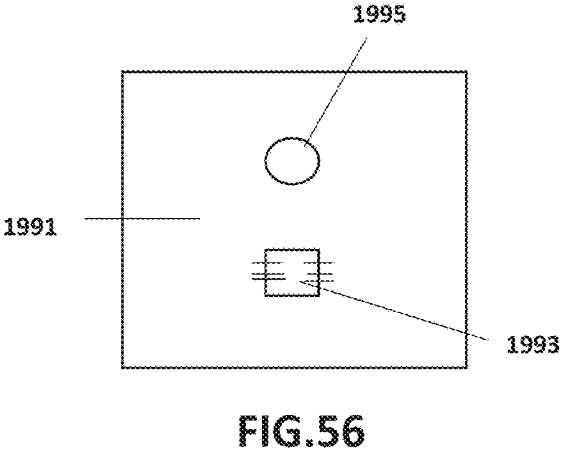
FIG. 56 is a representation of a sensor used on the balance pod.

Referring now to FIGS. 55 and 56, the dome 1950 include features to mount a blood sensor 1991 to optically measure the fluids in the balance chamber. The blood sensor 1991 comprises a PCB 1991 mounted on each dome 1940, 1950 (only one is shown). The first PCB sensor 1991 has an LED and directs visible or infrared light into the balance chambers and the second PCB sensor 1991 has an optical sensor to measure the light that passes through the balance chamber. The first PCB sensor is mounted on one of the rigid domes 1940, 1950 and the second PCB sensor is mounted on the other rigid dome. The design and use of a sensor to optically measure the amount of blood in balance chamber was disclosed in application n U.S. patent application Ser. No. 13/480,444, filed May 24, 2012 entitled "Blood treatment systems and methods," and incorporated herein by reference. Each dome includes elements molded into the dome to hold the PCB based sensors. A flat straight groove 1994 is molded into the outside surface of the dome 1950A that receives the lower edge of the sensor PCB 1991. A post 1996 extend from the outer surface of the dome 1950A with a projection 1997 that engages an opening 1995 in the PCB sensor 1991. A window 1992 is molded into the outer surface of dome 1950A that is configured to provide a surface perpendicular to the the LED light or optical sensor 1993 of the PCB. The perpendicular surface minimized reflection from the ambient and maximized the amount of light sent by an LED and received by an optical sensor.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A disposable blood cassette with a vial holder for use in a hemodialysis unit, comprising:
- a back plate;
- a front plate with an opening;
- a midplate bonded to the back plate on a first face and bonded to the front plate on an opposite face; and
- a vial holder configured to receive a vial and comprising:
  - a vial support comprising:
    - a vertically oriented spine that extends through the front plate and is fused to the mid-plate;
    - a support ring integral to the spine and with a vertically oriented center axis of the ring;
    - a support arm that extends horizontally from the spine;
    - a hollow spike with a first end that extends vertically from the support arm and a second end that extends through the support arm to a first fluid channel in the blood pump cassette; and
    - a support cylinder aligned with the support ring and comprising:
      - two pads located on opposite sides of the support cylinder and attached to the support cylinder by living hinges that bend about a vertical axis;
      - a first complete ring above the pads; and
      - a second complete ring below the pads;
    - wherein the support cylinder is mechanically attached to the support ring;
- wherein said vial holder is configured to receive a cylindrical vial; and
- wherein the two opposed pads are configured to center the vial over the hollow spike.

2. The disposable blood cassette of claim 1, where the spine is fused to a housing with ultrasonic welding, adhesives, or laser welding.

3. The disposable blood cassette of claim 1, wherein the second end of the hollow spike extends through the front plate and is sealed with an O-ring held between the spine and the mid-plate.

4. The disposable blood cassette of claim 1, wherein each pad contains a tampered surface above a contact surface that provide a ramp that makes contact with said cylindrical vial as the vial moves toward the hollow spike and facilitates the movement of the vial toward the support arm.

5. The disposable blood cassette of claim 1, wherein the support of the vial holder is reinforced by gussets for structural integrity which connect the vertically oriented support spine to the support ring.

6. The disposable blood cassette from claim 1, wherein the blood cassette comprises: a blood pump;

a blood inlet;

a blood outlet; and one or more blood channels fluidly connecting the blood inlet to the blood pump and fluidly connecting the blood pump to the blood outlet;

wherein the first fluid channel is fluidly connected to at least one of the blood channels.

7. The disposable blood cassette of claim 6, where the first fluid channel is connected one of the blood channels via a valve and a metering pump.

8. The disposable blood cassette of claim 7, where the first fluid channel is a port to a diaphragm valve.

9. The disposable blood cassette of claim 8, where the spine is fused to the housing with ultrasonic welding, adhesives, or laser welding.

10. A disposable blood cassette with a vial holder for use in a hemodialysis unit, comprising:

a blood pump comprising:

a housing;

a blood pump;

a blood inlet;

a blood outlet; and one or more fluid channels fluidly connecting the blood inlet to the blood pump and fluidly connecting the blood pump to the blood outlet; and a vial holder to receive a vial and comprising:

a vial support comprising:

a vertically oriented spine fused to the housing;

a support ring that is integral to the spine and oriented so a center axis of the ring is vertical;

a support arm that extends horizontally from the spine; a hollow spike with a first end that extends vertically from the support arm and a second end that extends through the support arm to a fluid channel; and a support cylinder aligned with the support ring and comprising:

two pads located on opposite sides of the support cylinder and attached to the support cylinder by living hinges that bend about a vertical axis;

a first complete ring above the pads;

a second complete ring below the pads; and tabs that extend vertically off the second ring that mechanically attach the support cylinder to the support ring;

wherein said vial holder is configured to receive a cylindrical vial;

wherein the two opposed pads are configured to center the vial over the hollow spike.

11. A disposable blood cassette with a vial holder for use in a hemodialysis unit, comprising: a blood pump comprising:

a housing;

a blood pump;

a blood inlet;

a blood outlet; and one or more fluid channels fluidly connecting the blood inlet to the blood pump and fluidly connecting the blood pump to the blood outlet; and a vial holder to receive a vial and comprising: a vial support comprising:

a vertically oriented spine fused to the housing;

a support ring that is integral to the spine and oriented so a center axis of the ring is vertical;

a support arm that extends horizontally from the spine; and a hollow spike with a first end that extends vertically from the support arm and a second end that extends through the support arm to a fluid channel; and a support cylinder aligned with the support ring and comprising:

two windows on opposite sides of the support cylinder; and two pads, each located in a window and attached to the support cylinder by a living hinge that bends about a vertical axis;

wherein the support cylinder is mechanically attached to the support ring;

wherein the vial holder is configured to receive a vial; and wherein the two opposed pads center the vial toward a plane defined by the first end of the hollow spike and the spine.

12. The disposable blood cassette of claim 11, wherein the two opposed pads center the cylindrical vial with first end of the hollow spike.

* * * * *